US012806277B2

(12) United States Patent
Schissel et al.

(10) Patent No.: US 12,806,277 B2
(45) Date of Patent: Nov. 24, 2026

(54) DESIGNING ANTISENSE OLIGONUCLEOTIDE DELIVERY PEPTIDES BY INTERPRETABLE MACHINE LEARNING

(71) Applicants: Sarepta Therapeutics, Inc., Cambridge, MA (US); Massachusetts Institute of Technology, Cambridge, MA (US)

(72) Inventors: Carly Schissel, Cambridge, MA (US); Somesh Mohapatra, Cambridge, MA (US); Justin Wolfe, Cambridge, MA (US); Colin Fadzen, Cambridge, MA (US); Chia-Ling Wu, Cambridge, MA (US); Annika Malmberg, Cambridge, MA (US); Gunnar Hanson, Cambridge, MA (US); Bradley Pentelute, Cambridge, MA (US); Rafael Gomez-Bombarelli, Cambridge, MA (US); Eva Maria Lopez Vidal, Cambridge, MA (US)

(73) Assignees: SAREPTA THERAPEUTICS, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 843 days.

(21) Appl. No.: 17/759,355

(22) PCT Filed: Jan. 22, 2021

(86) PCT No.: PCT/US2021/014575
§ 371 (c)(1),
(2) Date: Jul. 22, 2022

(87) PCT Pub. No.: WO2021/150867
PCT Pub. Date: Jul. 29, 2021

(65) Prior Publication Data

US 2025/0228954 A1 Jul. 17, 2025

Related U.S. Application Data

(60) Provisional application No. 63/134,405, filed on Jan. 6, 2021, provisional application No. 62/965,555, filed on Jan. 24, 2020.

(51) Int. Cl.
*A61K 47/64* (2017.01)
*A61K 47/54* (2017.01)

(52) U.S. Cl.
CPC ............ *A61K 47/64* (2017.08); *A61K 47/545* (2017.08); *A61K 47/549* (2017.08); *A61K 47/645* (2017.08)

(58) Field of Classification Search
CPC .... A61K 47/64; A61K 47/545; A61K 47/549; A61K 47/645
See application file for complete search history.

(56) References Cited

U.S. PATENT DOCUMENTS 5,034,506 A 7/1991 Summerton et al.
5,142,047 A 8/1992 Summerton et al.
(Continued)

FOREIGN PATENT DOCUMENTS

JP 2007532666 A 11/2007
JP 2015535299 A 12/2015
(Continued)

OTHER PUBLICATIONS

Kim et al., Biomedical applications of copper-free click chemistry: in vitro, in vivo, and ex vivo. Chem Sci. Aug. 16, 2019;10(34):7835-7851. doi: 10.1039/c9sc03368h. PMID: 31762967; PMCID: PMC6855312 (Year: 2019).*
(Continued)

*Primary Examiner* — Randall L Beane
(74) *Attorney, Agent, or Firm* — STERNE, KESSLER, GOLDSTEIN & FOX P.L.L.C.

(57) ABSTRACT

Provided herein are oligonucleotides, trimeric peptides, and peptide-oligonucleotide-conjugates. Also provided herein are methods of treating a muscle disease in a subject in need thereof, comprising administering to the subject oligonucleotides, trimeric peptides, and peptide-oligonucleotide-conjugates described herein. A synthetic method provides for the generation of a library of cell-penetrating peptides conjugated to an antisense oligonucleotide, and a machine learning-based generator-predictor-optimizer loop for the
(Continued)

generation of novel peptide sequences capable of enhanced delivery of oligonucleotide cargo from the library of conjugates.

18 Claims, 39 Drawing Sheets

Specification includes a Sequence Listing.

(56) References Cited

U.S. PATENT DOCUMENTS

| | | | | |
|---|---|---|---|---|
| 5,166,315 | A | 11/1992 | Summerton et al. | |
| 5,185,444 | A | 2/1993 | Summerton et al. | |
| 5,217,866 | A | 6/1993 | Summerton et al. | |
| 5,506,337 | A | 4/1996 | Summerton et al. | |
| 5,521,063 | A | 5/1996 | Summerton et al. | |
| 5,698,685 | A | 12/1997 | Summerton et al. | |
| 8,076,476 | B2 | 12/2011 | Reeves et al. | |
| 8,299,206 | B2 | 10/2012 | Fox et al. | |
| 8,969,551 | B2 | 3/2015 | Ueda | |
| 12,168,059 | B2 * | 12/2024 | Wolfe | A61K 47/645 |
| 12,370,261 | B2 * | 7/2025 | Pentelute | A61K 47/645 |
| 2009/0131624 | A1 | 5/2009 | Reeves et al. | |
| 2009/0131632 | A1 | 5/2009 | Fox et al. | |
| 2015/0238627 | A1 | 8/2015 | Leger et al. | |
| 2021/0290772 | A1 * | 9/2021 | Wolfe | C12N 15/113 |

FOREIGN PATENT DOCUMENTS

| | | | |
|---|---|---|---|
| TW | 201928056 | A | 7/2019 |
| WO | WO-2005115444 | A2 | 12/2005 |
| WO | WO-2009064471 | A1 | 5/2009 |
| WO | WO-2012043730 | A1 | 4/2012 |
| WO | WO-2014072411 | A1 | 5/2014 |
| WO | WO 2019/079386 | A1 | 4/2019 |
| WO | WO-2019154901 | A1 | 8/2019 |
| WO | WO-2019178479 | A1 | 9/2019 |
| WO | WO-2019241385 | A2 | 12/2019 |
| WO | WO-2020028254 | A1 | 2/2020 |

OTHER PUBLICATIONS

Wolfe et al., Machine Learning To Predict Cell-Penetrating Peptides for Antisense Delivery. ACS Cent Sci. Apr. 25, 2018;4(4):512-520. doi: 10.1021/acscentsci.8b00098. Epub Apr. 5, 2018. PMID: 29721534; PMCID: PMC5920612 (Year: 2018).*

Pickens et al., Practical Considerations, Challenges, and Limitations of Bioconjugation via Azide-Alkyne Cycloaddition. Bioconjug Chem. Mar. 21, 2018;29(3):686-701. doi: 10.1021/acs.bioconjchem.7b00633. Epub Feb. 1, 2018. PMID: 29287474; PMCID: PMC6310217 (Year: 2018).*

Gennaro, A.R., ed., "Table II: FDA-Approved Commercially Marketed Salts," in *Remington's Pharmaceutical Sciences*, $17^{th}$ Edition, Chapter 76, p. 1418, Mack Publishing Company, Easton, United States (1985).

Revankar, G.R., and Rao, T.S., "DNA with Altered Bases," in *Comprehensive Natural Products Chemistry*, Kool, E.T., ed., vol. 7, Chapter 9, pp. 313-339, Elsevier Science Ltd., Amsterdam, Netherlands (1999).

Benner, S.A. and Sismour, A.M., "Synthetic Biology," Nature Reviews, Genetics 6(7):533-543, Nature Publishing Group, United Kingdom (Jul. 2005).

Berge, S.M., et al., "Pharmaceutical Salts," Journal of Pharmaceutical Sciences 66(1):1-19, Elsevier, United States (Jan. 1977).

Chiu, Y.L. and Rana, T.M., "SiRNA Function in RNAi: A Chemical Modification Analysis," RNA 9(9):1034-1048, Cold Spring Harbor Laboratory Press, United States (Sep. 2003).

Greene, T.W. and Wuts, P.G.M., "Protective Groups in Organic Synthesis," 3rd Edition, John Wiley & Sons, New York, 1999.

Hames, B.D and Higgins, S.J., "Nucleic Acid Hybridization, " IRL Press, pp. 107-108, Practical Approach Series (1985).

Henry, A.A. and Romesberg, F.E., "Beyond A, C, G and T: Augmenting Nature's Alphabet," Current Opinion in Chemical Biology 7(6):727-733, Elsevier, United Kingdom (Dec. 2003).

Hirao, I., "Unnatural Base Pair Systems for DNA/RNA-based Biotechnology," Current Opinion in Chemical Biology 10(6):622-627, Elsevier, United Kingdom (Dec. 2006).

Kool, E.T., "Replacing the Nucleobases in DNA with Designer Molecules," Accounts of Chemical Research 35(11):936-943, American Chemical Society, United States (Nov. 2002).

Krueger, A.T . . . et al., Synthesis and properties of size-expanded DNAs: toward designed, functional genetic systems, Acc Chem Res 40(2): 141-150, American Chemical Society, United States (Feb. 2007).

Lehto, T., et al., "Peptides for Nucleic Acid Delivery," Advanced Drug Delivery Reviews 106(Pt A):172-182, Elsevier Science Publishers, Netherlands (Nov. 2016).

Limbach, P.A., et al., "Summary: the Modified Nucleosides of RNA," Nucleic Acids Research 22(12):2183-2196, Oxford University Press, United Kingdom (Jun. 1994).

Miyada, C.G., and Wallace, R.B., "Oligonucleotide Hybridization Techniques," Methods in Enzymology 154:94-107, Academic Press, United States (1987).

Ravin, L.J., "Preformulation," Remington's Pharmaceutical Sciences, 17th Edition, 1-17, Mack Publishing Company, Easton, PA (1985).

Remington's Pharmaceutical Sciences, 18th ed., pp. 172-174, Mack Publishing, Easton, PA, 173, (1990).

Summerton, J., and Weller, D., "Morpholino Antisense Oligomers: Design, Preparation, and Properties," Antisense & Nucleic Acid Drug Development 7(3):187-195, Mary Ann Liebert, Inc., United States (Jun. 1997).

European Supplementary Partial European Search Report for European Application No. EP 21743806, mailed on Sep. 27, 2024, 13 pages.

International Search Report and Written Opinion for PCT Application No. PCT/US2021/014575, mailed Jun. 29, 2021, 12 pages.

International Search Report and Written Opinion in related PCT Application No. PCT/US2021/014575, mailed Jun. 29, 2021, 5 pages.

* cited by examiner

Module 1

| PMO | Sequence |
|---|---|
| IVS2-654 | GCTATTACCTTAACCCAG |

Module 2

| Peptide 1 | Sequence |
|---|---|
| Penetratin | RQIKIWFQNRRMKWKK |
| pVEC | LLIILRRRIRKQAHAHSK |
| TP10 | AGYLLGKINLKALAALAKKIL |
| DPV6 | GRPRESGKKRKRKRLKP |

Module 3

| Peptide 2 | Sequence |
|---|---|
| KRVK (NLS) | KRVK |
| SV40 (NLS) | PKKKRKV |
| AAV-PHP.eB | SDGTLAVPFKA |

Module 4

| Peptide 3 | Sequence |
|---|---|
| Bpep | RXRRBRRXRRBR |
| DPV6 | GRPRESGKKRKRKRLKP |
| PPC3 | KKYRGRKRHPR |

Fig. 5

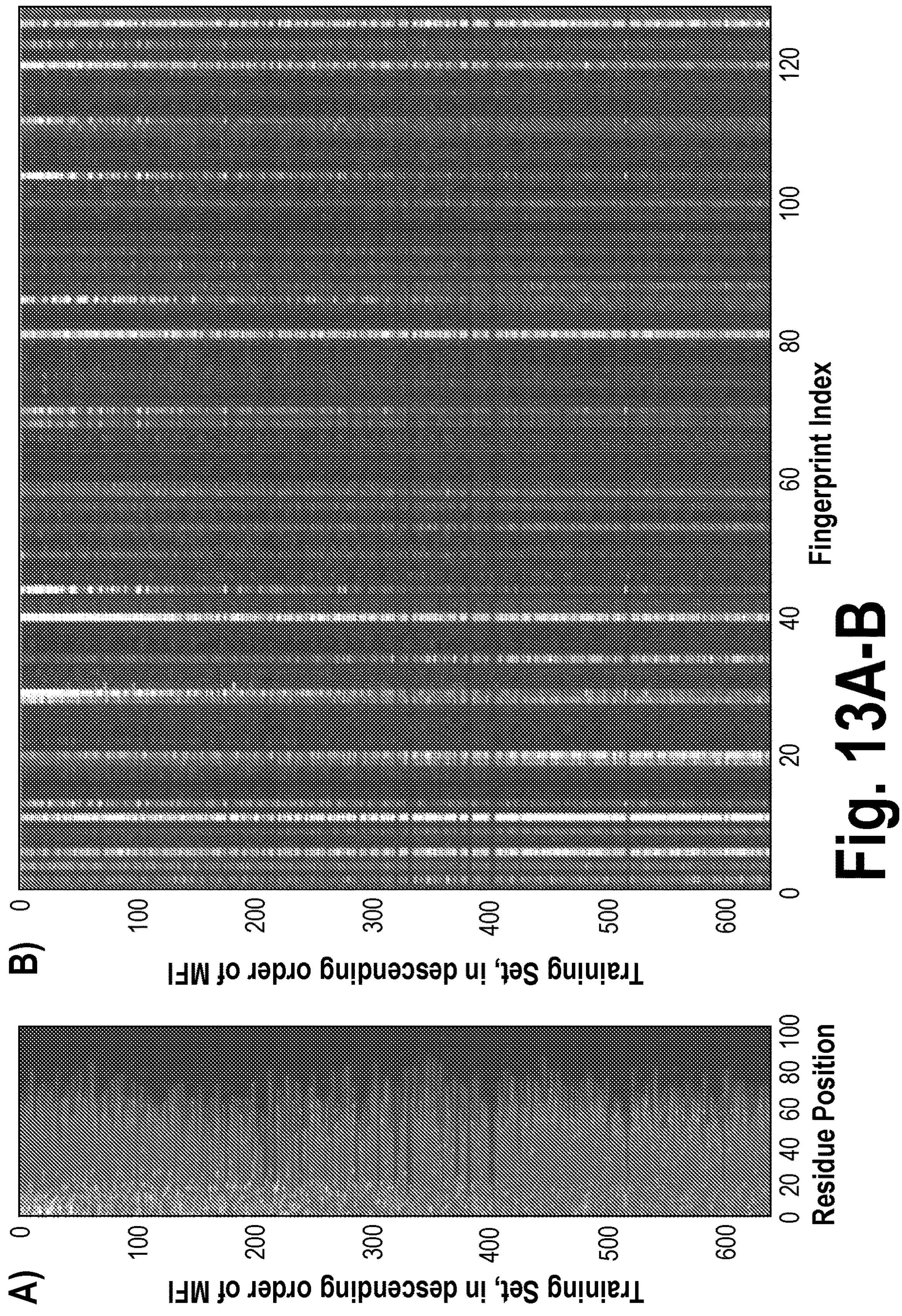
Fig. 13A-B

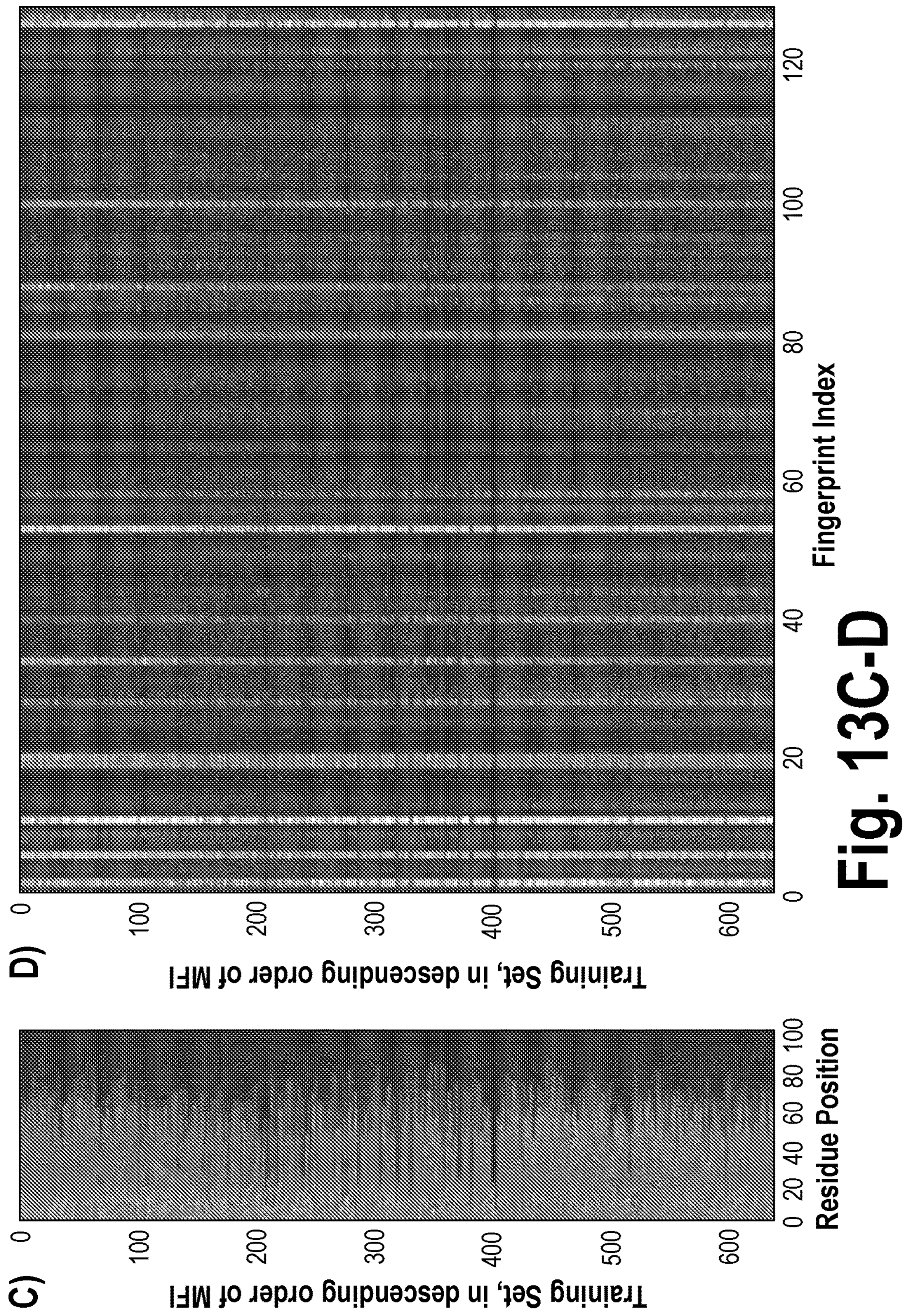
Fig. 13C-D

E)
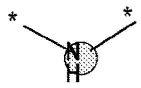
0
3
5
10
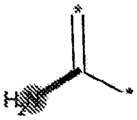
12
18
19
27
28
33
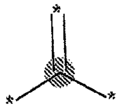
39
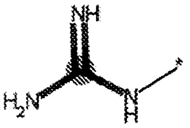
43
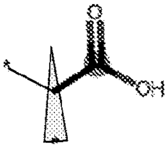
52
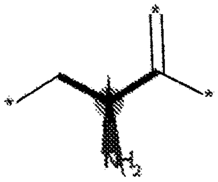
57
67
68
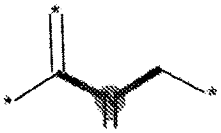
69
80
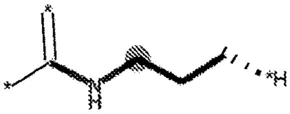
84
87
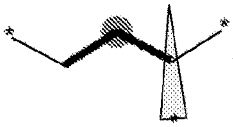
99
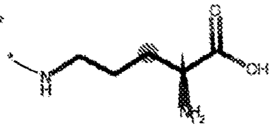
103
111
119
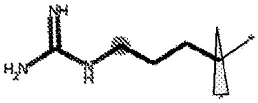
122
125
126
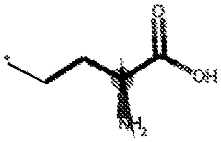
127
Fig. 13E F)
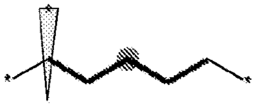
3
5
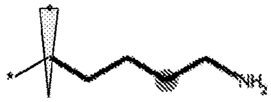
8
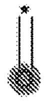
10
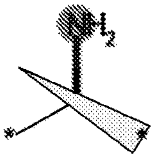
18
19
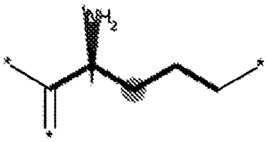
28
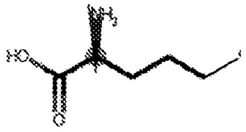
33
39
48
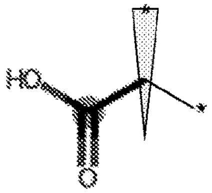
52
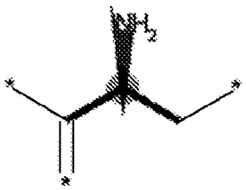
57
58
80
85
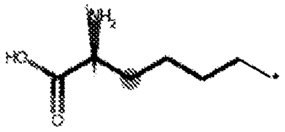
86
92
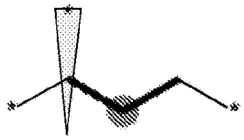
99
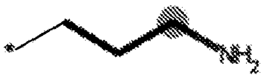
109
119
125
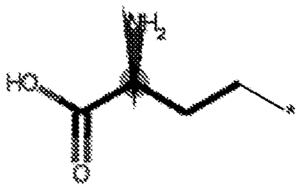
127
Fig. 13F G)
5
10
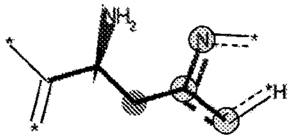
17
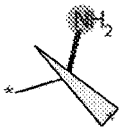
18
19
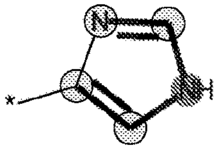
35
39
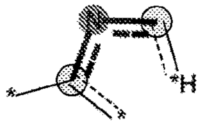
44
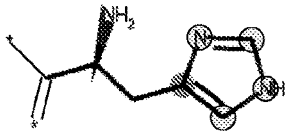
49
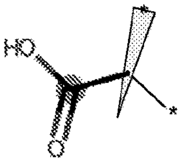
52
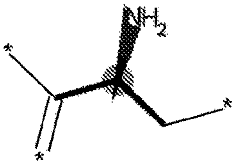
57
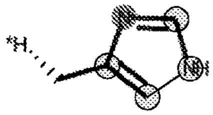
63
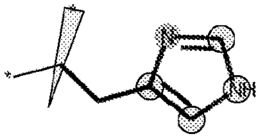
65
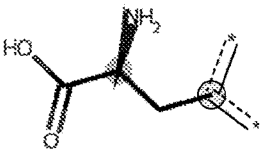
69
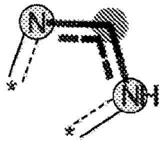
73
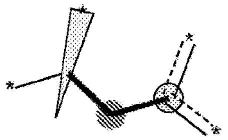
79
80
81
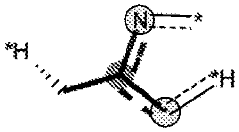
84
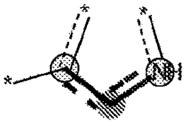
87
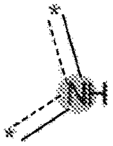
90
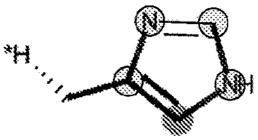
94
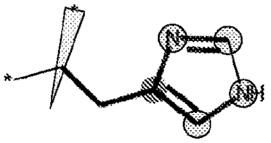
97
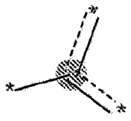
100
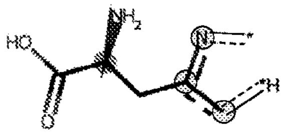
107
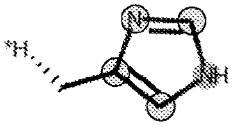
108
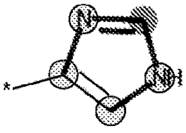
113
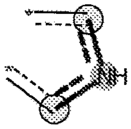
120
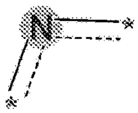
122
Fig. 13G
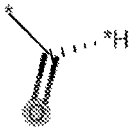
125

H)
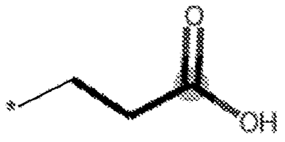
7
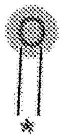
10
19
21
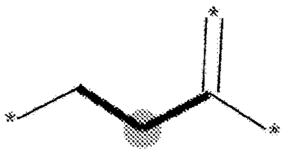
28
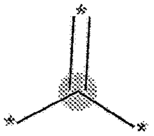
39
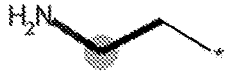
48
49
54
58
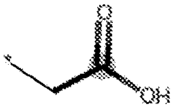
73
80
85
86
109
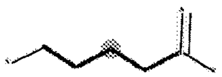
115
119
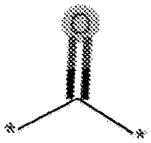
125
Fig. 13H

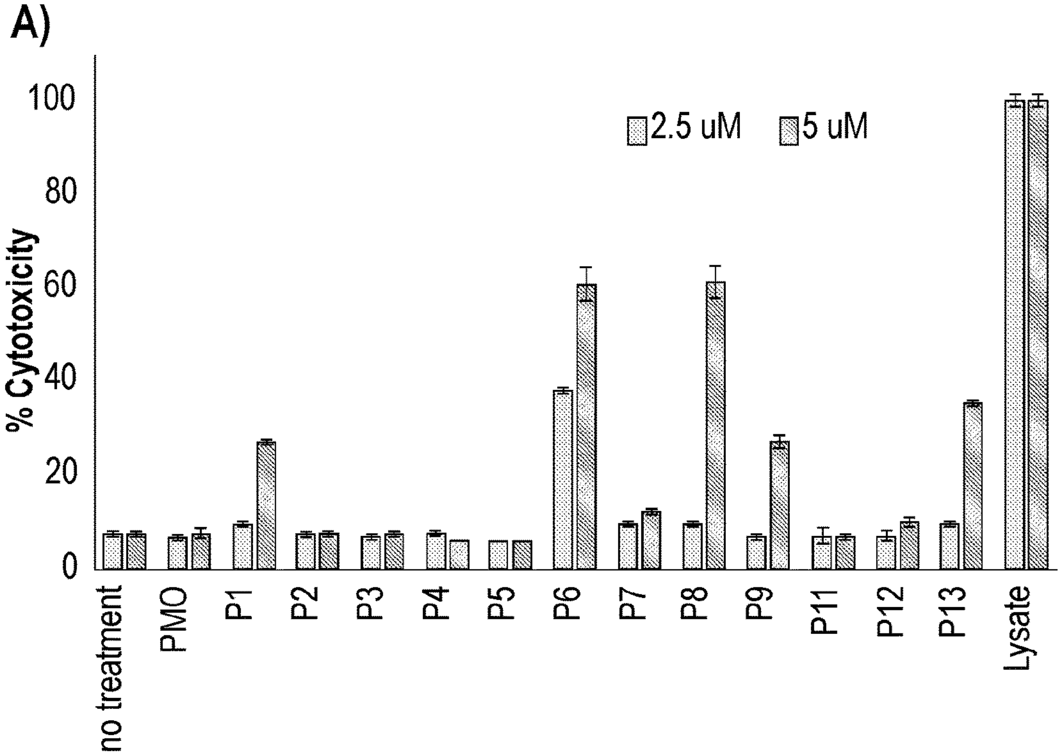
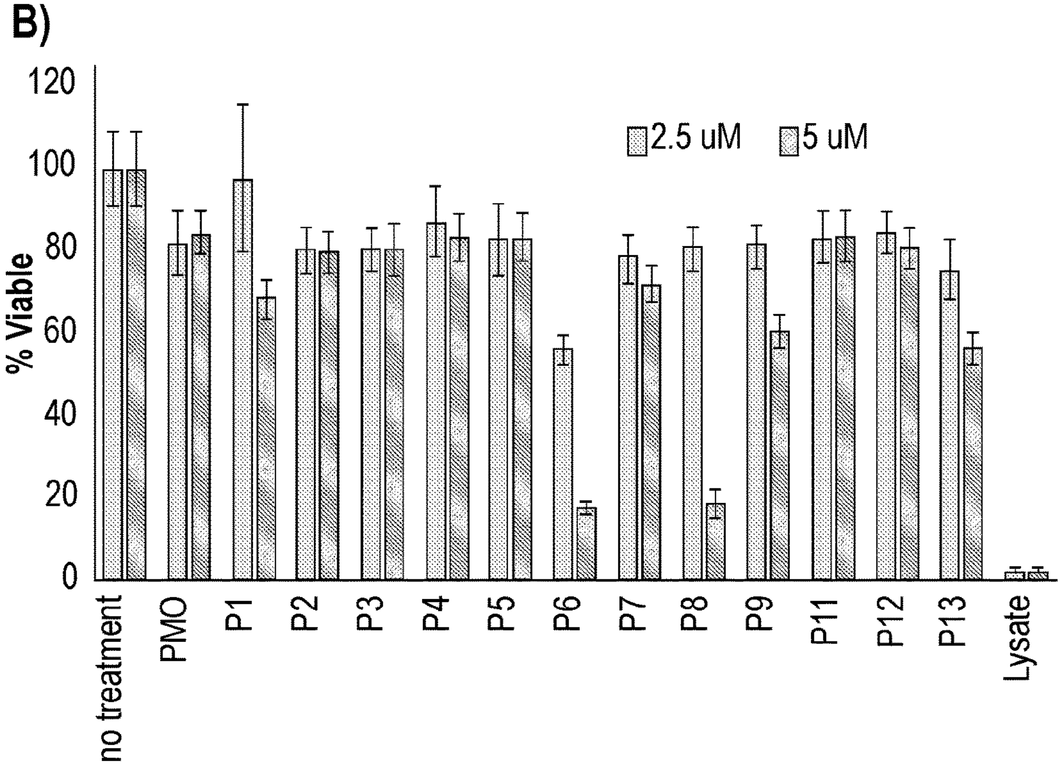
Fig. 15A-B

Fig. 22A-C

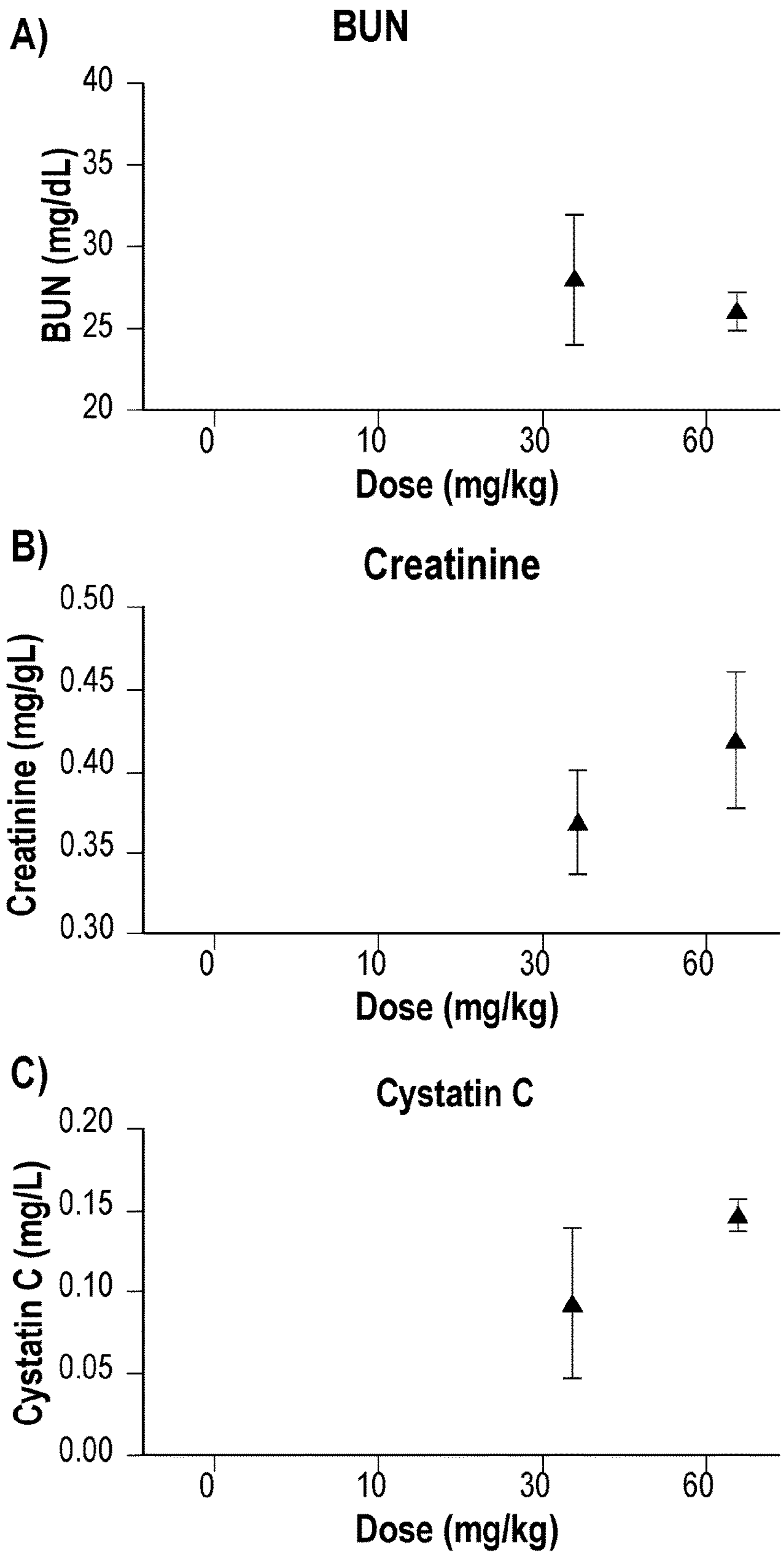
Fig. 24A-C

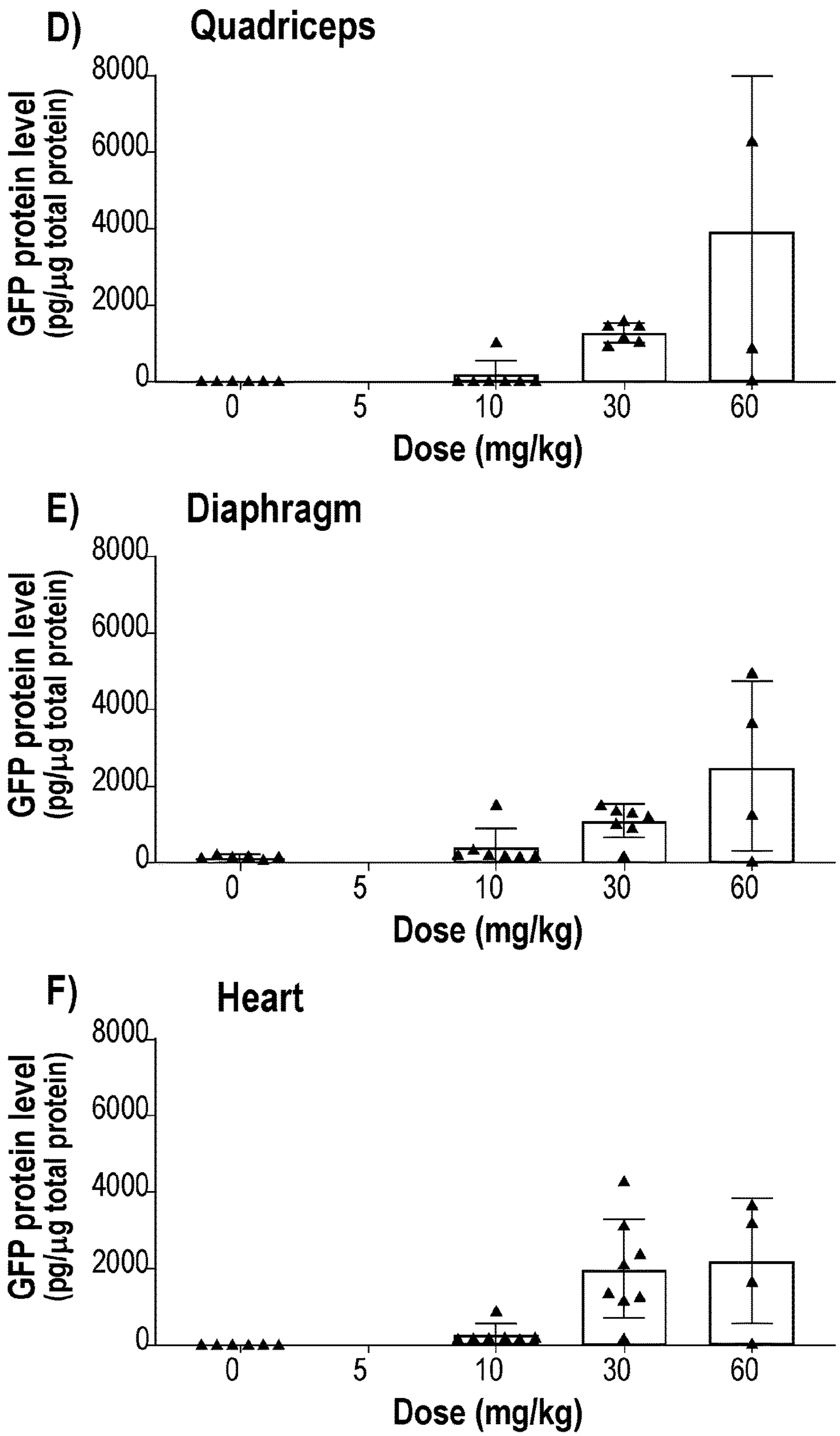
Fig. 24D-F

SEQUENCE LISTING

```
<160> NUMBER OF SEQ ID NOS: 109

<210> SEQ ID NO 1
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 1

Gly Arg Pro Arg Glu Ser Gly Lys Lys Arg Lys Arg Lys Arg Leu Lys
1               5                   10                  15

Pro

<210> SEQ ID NO 2

<400> SEQUENCE: 2

000

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Lys Ala Ala Arg Ala Pro Gly Arg Arg Lys Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg Arg Arg Arg Arg Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(14)
<223> OTHER INFORMATION: Decafluorobiphenyl linker

<400> SEQUENCE: 5

Cys Arg Arg Arg Arg Arg Arg Arg Arg Arg Arg Arg Arg Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: Decafluorobiphenyl linker

<400> SEQUENCE: 6

Cys Arg Arg Arg Arg Arg Arg Cys Arg Arg Arg Arg Arg Arg 1 5 10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (7)..(14)
<223> OTHER INFORMATION: Decafluorobiphenyl linker

<400> SEQUENCE: 7

Arg Arg Arg Arg Arg Arg Cys Arg Arg Arg Arg Arg Arg Cys
1 5 10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(8)
<223> OTHER INFORMATION: 1,3,5-trisbromomethylbenzene linker
<220> FEATURE:
<221> NAME/KEY: SITE
<222> LOCATION: (8)..(15)
<223> OTHER INFORMATION: 1,3,5-trisbromomethylbenzene linker

<400> SEQUENCE: 8

Cys Arg Arg Arg Arg Arg Arg Cys Arg Arg Arg Arg Arg Arg Cys
1 5 10 15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(8)
<223> OTHER INFORMATION: Decafluorobiphenyl linker
<220> FEATURE:
<221> NAME/KEY: SITE
<222> LOCATION: (9)..(16)
<223> OTHER INFORMATION: Decafluorobiphenyl linker

<400> SEQUENCE: 9

Cys Arg Arg Arg Arg Arg Arg Cys Cys Arg Arg Arg Arg Arg Arg Cys
1 5 10 15

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)

<223> OTHER INFORMATION: Beta-alanine
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: Beta-alanine

<400> SEQUENCE: 10

Arg Xaa Arg Arg Ala Arg Arg Xaa Arg Arg Ala Arg
1 5 10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(14)
<223> OTHER INFORMATION: Decafluorobiphenyl linker
<220> FEATURE:
<221> NAME/KEY: MOD_RES
<222> LOCATION: (3)..(3)
<223> OTHER INFORMATION: Aminohexanoic acid
<220> FEATURE:
<221> NAME/KEY: MOD_RES
<222> LOCATION: (6)..(6)
<223> OTHER INFORMATION: Beta-alanine
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (12)..(12)
<223> OTHER INFORMATION: Beta-alanine

<400> SEQUENCE: 11

Cys Arg Xaa Arg Arg Ala Arg Arg Xaa Arg Arg Ala Arg Cys
1 5 10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: Beta-alanine
<220> FEATURE:
<221> NAME/KEY: SITE
<222> LOCATION: (7)..(14)
<223> OTHER INFORMATION: Decafluorobiphenyl linker
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (12)..(12)
<223> OTHER INFORMATION: Beta-alanine

<400> SEQUENCE: 12

Arg Xaa Arg Arg Ala Arg Cys Arg Xaa Arg Arg Ala Arg Cys
1 5 10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (12)..(12)
<223> OTHER INFORMATION: Norleucine

<400> SEQUENCE: 13

Arg Gln Ile Lys Ile Trp Phe Gln Asn Arg Arg Xaa Lys Trp Lys Lys
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(8)
<223> OTHER INFORMATION: Decafluorobiphenyl linker

<400> SEQUENCE: 14

Cys Gln Ile Lys Ile Trp Phe Cys Asn Lys Arg Ala Lys Ile Lys Lys
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (9)..(16)
<223> OTHER INFORMATION: Decafluorobiphenyl linker

<400> SEQUENCE: 15

Ser Gln Ile Lys Ile Trp Phe Gln Cys Lys Arg Ala Lys Ile Lys Cys
1 5 10 15

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(18)
<223> OTHER INFORMATION: Decafluorobiphenyl linker

<400> SEQUENCE: 16

Cys Ser Gln Ile Lys Ile Trp Phe Gln Asn Lys Arg Ala Lys Ile Lys
1 5 10 15

Lys Cys

-continued

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Leu Leu Ile Ile Leu Arg Arg Arg Ile Arg Lys Gln Ala His Ala His
1 5 10 15

Ser Lys

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (20)..(20)
<223> OTHER INFORMATION: Aminohexanoic acid
<220> FEATURE:
<221> NAME/KEY: MOD_RES
<222> LOCATION: (23)..(23)
<223> OTHER INFORMATION: Beta-alanine
<220> FEATURE:
<221> NAME/KEY: MOD_RES
<222> LOCATION: (26)..(26)
<223> OTHER INFORMATION: Aminohexanoic acid
<220> FEATURE:
<221> NAME/KEY: MOD_RES
<222> LOCATION: (29)..(29)
<223> OTHER INFORMATION: Beta-alanine

<400> SEQUENCE: 18

Leu Leu Ile Ile Leu Arg Arg Arg Ile Arg Lys Gln Ala His Ala His
1 5 10 15

Ser Lys Arg Xaa Arg Arg Ala Arg Arg Xaa Arg Arg Ala Arg
20 25 30

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: SITE
<222> LOCATION: (2)..(8)
<223> OTHER INFORMATION: Decafluorobiphenyl linker

<400> SEQUENCE: 19

Glx Cys Arg Leu Arg Trp Arg Cys
1 5

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (28)..(28)
<223> OTHER INFORMATION: Aminohexanoic acid
<220> FEATURE:

<221> NAME/KEY: MOD_RES
<222> LOCATION: (31)..(31)
<223> OTHER INFORMATION: Beta-alanine
<220> FEATURE:
<221> NAME/KEY: MOD_RES
<222> LOCATION: (34)..(34)
<223> OTHER INFORMATION: Aminohexanoic acid
<220> FEATURE:
<221> NAME/KEY: MOD_RES
<222> LOCATION: (37)..(37)
<223> OTHER INFORMATION: Beta-alanine

<400> SEQUENCE: 20

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln Arg Xaa Arg Arg Ala Arg
            20                  25                  30

Arg Xaa Arg Arg Ala Arg
        35
```

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

```
Ile Trp Ile Ala Gln Glu Leu Arg Arg Ile Gly Asp Glu Phe Asn Ala
1               5                   10                  15

Tyr Tyr Ala Arg Arg
            20
```

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

```
Arg Arg Ile Arg Pro Arg Pro Pro Arg Leu Pro Arg Pro Arg Pro Arg
1               5                   10                  15

Pro Leu Pro Phe Pro Arg Pro Gly
            20
```

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

```
Thr Arg Ser Ser Arg Ala Gly Leu Gln Trp Pro Val Gly Arg Val His
1               5                   10                  15

Arg Leu Leu Arg Lys
            20
```

<210> SEQ ID NO 24
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Gly Arg Leu Ser Tyr Ser Arg Arg Arg Phe Ser Thr Ser Thr
1               5                   10                  15

Gly Arg

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Leu Trp Lys Thr Leu Leu Lys Lys Val Leu Lys Ala Pro Lys Lys
1               5                   10                  15

Lys Arg Lys Val
            20

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Leu Ser Ser Ile Phe Ser Arg Ile Gly Asp Pro
1               5                   10

<210> SEQ ID NO 29
<211> LENGTH: 17

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Lys Leu Ala Leu Lys Ala Leu Lys Ala Leu Lys Ala Ala Leu Lys Leu
1 5 10 15

Ala

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Arg Arg Trp Trp Arg Arg Trp Arg Arg
1 5

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Leu Lys Thr Leu Thr Glu Thr Leu Lys Glu Leu Thr Lys Thr Leu Thr
1 5 10 15

Glu Leu

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Val Arg Leu Pro Pro Pro Val Arg Leu Pro Pro Pro Val Arg Leu Pro
1 5 10 15

Pro Pro

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Phe Lys Ile Tyr Asp Lys Lys Val Arg Thr Arg Val Val Lys His
1 5 10 15

<210> SEQ ID NO 34
<211> LENGTH: 16
<212> TYPE: PRT
<213> ORGANISM: Artificial Sequence
<220> FEATURE:

<223> OTHER INFORMATION: Description of Artificial Sequence: Synthetic peptide

<400> SEQUENCE: 34

Lys Gly Thr Tyr Lys Lys Lys Leu Met Arg Ile Pro Leu Lys Gly Thr
1 5 10 15

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Leu Tyr Lys Lys Gly Pro Ala Lys Lys Gly Arg Pro Pro Leu Arg Gly
1 5 10 15

Trp Phe His

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ile Ala Trp Val Lys Ala Phe Ile Arg Lys Leu Arg Lys Gly Pro Leu
1 5 10 15

Gly

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Ser Pro Trp Gly Leu Gln His His Pro Pro Arg Thr
1 5 10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Arg Gln Val Thr Ile Trp Ser Gln Asn Arg Arg Val Lys Ser Lys Lys
1 5 10 15

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Val Ser Ala Leu Lys
1               5


<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Pro Arg Pro Pro Arg Pro Pro Arg
1               5


<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Pro Arg Pro Pro Arg Pro Pro Arg Pro Pro Arg
1               5                   10


<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Leu Arg Trp Arg
1               5


<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ala Tyr Asp Leu Arg Arg Arg Glu Arg Gln Ser Arg Leu Arg Arg
1               5                   10                  15

Arg Glu Arg Gln Ser Arg
            20


<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Lys Lys Arg Arg Gln Arg Arg Arg
1               5


<210> SEQ ID NO 45
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Gln Ile Lys Ile Trp Phe Gln Asn Arg Arg Met Lys Trp Lys Lys
1               5                   10                  15


<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Arg Arg Arg Arg Arg Arg Arg Arg
1               5


<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Val Thr Ile Trp Phe Gln Ser Arg Arg Val Lys Glu Lys Lys
1               5                   10                  15


<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Arg Val Lys Ala Gly Tyr Leu Leu Gly Lys Ile Asn Leu Lys Ala
1               5                   10                  15

Leu Ala Ala Leu Ala Lys Lys Ile Leu
            20                  25


<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Gly Tyr Leu Leu Gly Lys Ile Asn Leu Lys Ala Leu Ala Ala Leu
1               5                   10                  15

Ala Lys Lys Ile Leu Lys Arg Val Lys
            20                  25


<210> SEQ ID NO 50
<211> LENGTH: 4
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 50

Lys Arg Val Lys
1

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

```
Pro Lys Lys Lys Arg Lys Val Ala Gly Tyr Leu Leu Gly Lys Ile Asn
1               5                   10                  15

Leu Lys Ala Leu Ala Ala Leu Ala Lys Lys Ile Leu
            20                  25
```

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

```
Pro Lys Lys Lys Arg Lys Val
1               5
```

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

```
Ser Asp Gly Thr Leu Ala Val Pro Phe Lys Ala
1               5                   10
```

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Lys Lys Tyr Arg Gly Arg Lys Arg His Pro Arg
1 5 10

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
gctattacct taacccag 18

<210> SEQ ID NO 57
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (32)..(32)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (42)..(42)
<223> OTHER INFORMATION: Aminohexanoic acid

<400> SEQUENCE: 57

Ala Leu Lys Ala Arg Ser Ala Ala Lys Ala Val Arg Trp Pro Lys Lys
1 5 10 15

Lys Ile Lys Gln Ala Ser Lys Lys Val Ala Lys Tyr Ala Leu Xaa Xaa
20 25 30

Xaa Arg Lys Lys Lys Ala Ala Ser Lys Xaa Trp Leu Gln Leu His Trp
35 40 45

Pro Arg Trp
50

<210> SEQ ID NO 58
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (45)..(45)
<223> OTHER INFORMATION: Aminohexanoic acid

<400> SEQUENCE: 58

Pro Pro Leu Arg Asn Ala Lys Lys Lys Asn Leu Lys Asn Asn Leu Lys
1 5 10 15

```
Met Asp Pro Lys Phe Thr Lys Lys Val Lys Gln Gly Ala Leu Lys Leu
            20                  25                  30

Asn Arg Arg Lys Lys Asn Arg Gly Pro Lys Gly Pro Xaa Lys His Trp
        35                  40                  45

Thr Thr
    50


<210> SEQ ID NO 59
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (38)..(38)
<223> OTHER INFORMATION: Aminohexanoic acid

<400> SEQUENCE: 59

Gln Lys Lys Arg Lys Ser Lys Ala Asn Lys Lys Asn Trp Pro Lys Gly
1               5                   10                  15

Lys Leu Ser Ile His Ala Lys Asp Tyr Lys Gln Gly Pro Lys Ala Lys
            20                  25                  30

Xaa Arg Lys Gln Arg Xaa Arg
        35


<210> SEQ ID NO 60
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid

<400> SEQUENCE: 60

Lys Lys Gly Lys Lys Gln Asn Lys Lys Lys His Arg Trp Pro Lys Lys
1               5                   10                  15

Lys Val Pro Gln Pro Lys Lys Met Phe Lys Gln Gly Ala Ala Xaa Arg
            20                  25                  30

Xaa


<210> SEQ ID NO 61
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
```

```
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (32)..(32)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid

<400> SEQUENCE: 61

Ala Lys Lys Lys Ile Ala Lys Ala Lys Lys His Arg Gly Pro Asn Ala
1               5                   10                  15

Gly Ile His Ala Pro Val Ser Lys Ile Lys Asp Pro Leu Lys Xaa Xaa
            20                  25                  30

Xaa


<210> SEQ ID NO 62
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Beta-alanine
<220> FEATURE:
<221> NAME/KEY: MOD_RES
<222> LOCATION: (32)..(32)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (42)..(42)
<223> OTHER INFORMATION: Aminohexanoic acid

<400> SEQUENCE: 62

Ala Leu Lys Ala Arg Ser Ala Ala Lys Ala Val Arg Trp Pro Lys Lys
1               5                   10                  15

Ala Ile Lys Gln Ala Ser Lys Lys Val Ala Lys Tyr Ala Leu Lys Xaa
            20                  25                  30

Xaa Arg Lys Lys Lys Ala Ala Ser Lys Xaa Trp Leu Gln Leu His Trp
        35                  40                  45

Pro Arg Trp
    50


<210> SEQ ID NO 63
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Aminohexanoic acid
<220> FEATURE:
<221> NAME/KEY: MOD_RES
<222> LOCATION: (5)..(5)
<223> OTHER INFORMATION: Aminohexanoic acid
```

<220> FEATURE:
<221> NAME/KEY: MOD_RES
<222> LOCATION: (9)..(9)
<223> OTHER INFORMATION: Beta-alanine
<220> FEATURE:
<221> NAME/KEY: MOD_RES
<222> LOCATION: (45)..(45)
<223> OTHER INFORMATION: Aminohexanoic acid
<220> FEATURE:
<221> NAME/KEY: MOD_RES
<222> LOCATION: (48)..(48)
<223> OTHER INFORMATION: Aminohexanoic acid

<400> SEQUENCE: 63

```
Xaa Lys His Pro Xaa Ala Val Gln Ala Ala Ala Arg Ala Trp Lys Val
1               5                   10                  15

Pro Ala Ala Ala Leu Trp Lys Lys Lys Arg Leu Lys Lys Ser Ser Lys
            20                  25                  30

Gln Lys Lys Lys Trp Leu Trp Lys Ala Arg Ser Ala Xaa Lys Tyr Xaa
        35                  40                  45

Arg Leu Ile
    50
```

<210> SEQ ID NO 64
<211> LENGTH: 78
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Beta-alanine
<220> FEATURE:
<221> NAME/KEY: MOD_RES
<222> LOCATION: (19)..(19)
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (38)..(38)
<223> OTHER INFORMATION: Aminohexanoic acid
<220> FEATURE:
<221> NAME/KEY: MOD_RES
<222> LOCATION: (39)..(39)
<223> OTHER INFORMATION: Aminohexanoic acid
<220> FEATURE:
<221> NAME/KEY: MOD_RES
<222> LOCATION: (45)..(45)
<223> OTHER INFORMATION: Aminohexanoic acid
<220> FEATURE:
<221> NAME/KEY: MOD_RES
<222> LOCATION: (48)..(48)
<223> OTHER INFORMATION: Aminohexanoic acid
<220> FEATURE:
<221> NAME/KEY: MOD_RES
<222> LOCATION: (51)..(51)
<223> OTHER INFORMATION: Aminohexanoic acid
<220> FEATURE:
<221> NAME/KEY: MOD_RES
<222> LOCATION: (52)..(52)
<223> OTHER INFORMATION: Aminohexanoic acid
<220> FEATURE:
<221> NAME/KEY: MOD_RES
<222> LOCATION: (54)..(54)
<223> OTHER INFORMATION: Aminohexanoic acid -continued
<220> FEATURE:
<221> NAME/KEY: MOD_RES
<222> LOCATION: (58)..(58)
<223> OTHER INFORMATION: Aminohexanoic acid
<220> FEATURE:
<221> NAME/KEY: MOD_RES
<222> LOCATION: (64)..(64)
<223> OTHER INFORMATION: Aminohexanoic acid
<220> FEATURE:
<221> NAME/KEY: MOD_RES
<222> LOCATION: (70)..(70)
<223> OTHER INFORMATION: Aminohexanoic acid

<400> SEQUENCE: 64

```
Ala Lys Gly Lys Asn Leu Leu Ala Lys Ile Arg Arg Gly Pro Asn Gly
1               5                   10                  15

Gly Asn Ala Gln Gly Ser Gln Gly Tyr Leu Leu Tyr Leu Leu Xaa Arg
            20                  25                  30

Xaa Arg Arg Gln Arg Xaa Xaa Tyr Pro Trp Trp Arg Xaa Lys His Xaa
        35                  40                  45

Arg Trp Xaa Xaa Arg Xaa Arg Gly His Xaa Arg Arg Arg Arg Gln Xaa
    50                  55                  60

Leu Lys Pro Asp Arg Xaa Arg Gly Gly Lys Gly Ser Val Ser
65                  70                  75
```

<210> SEQ ID NO 65
<211> LENGTH: 66
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (8)..(8)
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (38)..(38)
<223> OTHER INFORMATION: Aminohexanoic acid
<220> FEATURE:
<221> NAME/KEY: MOD_RES
<222> LOCATION: (39)..(39)
<223> OTHER INFORMATION: Aminohexanoic acid
<220> FEATURE:
<221> NAME/KEY: MOD_RES
<222> LOCATION: (45)..(45)
<223> OTHER INFORMATION: Aminohexanoic acid
<220> FEATURE:
<221> NAME/KEY: MOD_RES
<222> LOCATION: (48)..(48)
<223> OTHER INFORMATION: Aminohexanoic acid
<220> FEATURE:
<221> NAME/KEY: MOD_RES
<222> LOCATION: (52)..(52)
<223> OTHER INFORMATION: Aminohexanoic acid
<220> FEATURE:
<221> NAME/KEY: MOD_RES
<222> LOCATION: (56)..(56)
<223> OTHER INFORMATION: Aminohexanoic acid
<220> FEATURE:
<221> NAME/KEY: MOD_RES
<222> LOCATION: (62)..(62)
<223> OTHER INFORMATION: Aminohexanoic acid

<400> SEQUENCE: 65

```
Lys Lys Lys Lys Asn Leu Asn Ala Lys Ser Arg Arg Gly Pro Asn Gly
1               5                   10                  15

Gly Ala Leu Gln Pro Ser Gln Gly Tyr Leu Gln Pro Leu Asn Xaa Arg
            20                  25                  30

Xaa Arg Arg Gln Arg Xaa Xaa Tyr Pro Trp Trp Arg Xaa Lys His Xaa
        35                  40                  45

Arg Trp Arg Xaa Arg Tyr His Xaa Arg Arg Arg Arg Gln Xaa Leu Lys
    50                  55                  60

Pro Gly
65
```

<210> SEQ ID NO 66
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (36)..(36)
<223> OTHER INFORMATION: Aminohexanoic acid

<400> SEQUENCE: 66

```
Thr Ser Asn Leu Lys Leu His Leu Ala Pro Pro Val Lys Lys Lys Ala
1               5                   10                  15

Leu Lys Lys Pro Leu Tyr Lys Ala Lys Lys Lys Lys Lys Val Val Ser
            20                  25                  30

Pro Thr Trp Xaa Thr Asp Gln Glu Trp
        35                  40
```

<210> SEQ ID NO 67
<211> LENGTH: 80
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (30)..(30)
<223> OTHER INFORMATION: Beta-alanine
<220> FEATURE:
<221> NAME/KEY: MOD_RES
<222> LOCATION: (31)..(31)
<223> OTHER INFORMATION: Aminohexanoic acid
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (38)..(38)
<223> OTHER INFORMATION: Aminohexanoic acid
<220> FEATURE:
<221> NAME/KEY: MOD_RES
<222> LOCATION: (39)..(39)
<223> OTHER INFORMATION: Aminohexanoic acid
<220> FEATURE:
<221> NAME/KEY: MOD_RES
<222> LOCATION: (42)..(42)
<223> OTHER INFORMATION: Aminohexanoic acid
<220> FEATURE:
<221> NAME/KEY: MOD_RES
<222> LOCATION: (45)..(45)
<223> OTHER INFORMATION: Aminohexanoic acid
<220> FEATURE:
<221> NAME/KEY: MOD_RES
<222> LOCATION: (48)..(48)
<223> OTHER INFORMATION: Aminohexanoic acid
<220> FEATURE:
<221> NAME/KEY: MOD_RES
<222> LOCATION: (51)..(51)
<223> OTHER INFORMATION: Aminohexanoic acid
<220> FEATURE:
<221> NAME/KEY: MOD_RES
<222> LOCATION: (52)..(52)
<223> OTHER INFORMATION: Aminohexanoic acid
<220> FEATURE:
<221> NAME/KEY: MOD_RES
<222> LOCATION: (53)..(53)
<223> OTHER INFORMATION: Aminohexanoic acid
<220> FEATURE:
<221> NAME/KEY: MOD_RES
<222> LOCATION: (54)..(54)
<223> OTHER INFORMATION: Aminohexanoic acid
<220> FEATURE:
<221> NAME/KEY: MOD_RES
<222> LOCATION: (55)..(55)
<223> OTHER INFORMATION: Aminohexanoic acid
<220> FEATURE:
<221> NAME/KEY: MOD_RES
<222> LOCATION: (60)..(60)
<223> OTHER INFORMATION: Aminohexanoic acid
<220> FEATURE:
<221> NAME/KEY: MOD_RES
<222> LOCATION: (66)..(66)
<223> OTHER INFORMATION: Aminohexanoic acid
<220> FEATURE:
<221> NAME/KEY: SITE
<222> LOCATION: (68)..(75)
<223> OTHER INFORMATION: Decafluorobiphenyl linker
<220> FEATURE:
<221> NAME/KEY: MOD_RES
<222> LOCATION: (72)..(72)
<223> OTHER INFORMATION: Aminohexanoic acid

<400> SEQUENCE: 67

```
Lys Gly Gly Lys Asn Leu Ala Lys Lys Ile Arg Arg Gly Pro Asn Gly
1               5                   10                  15

Gly Ala Leu Gln Pro Ser Gln Gly Tyr Leu Leu Tyr Leu Ala Xaa Arg
            20                  25                  30

Xaa Arg Arg Gln Arg Xaa Xaa Gly Pro Xaa Trp Arg Xaa Lys His Xaa
        35                  40                  45

Arg Trp Xaa Xaa Xaa Xaa Xaa Arg Pro Thr His Xaa Arg Arg Arg Arg
    50                  55                  60

Gln Xaa Leu Cys Pro Gly Arg Xaa Arg Pro Cys Arg Gly Ser Val Ser
65                  70                  75                  80
```

<210> SEQ ID NO 68
<211> LENGTH: 50
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (8)..(8)
<223> OTHER INFORMATION: Beta-alanine
<220> FEATURE:
<221> NAME/KEY: SITE
<222> LOCATION: (18)..(25)
<223> OTHER INFORMATION: Decafluorobiphenyl linker
<220> FEATURE:
<221> NAME/KEY: MOD_RES
<222> LOCATION: (33)..(33)
<223> OTHER INFORMATION: Aminohexanoic acid
<220> FEATURE:
<221> NAME/KEY: MOD_RES
<222> LOCATION: (38)..(38)

```
<223> OTHER INFORMATION: Aminohexanoic acid
<220> FEATURE:
<221> NAME/KEY: MOD_RES
<222> LOCATION: (45)..(45)
<223> OTHER INFORMATION: Aminohexanoic acid

<400> SEQUENCE: 68

Ala Lys Lys Lys Lys Leu Gly Ala Lys Ala Leu Arg Trp Pro Asn Gly
1               5                   10                  15

Lys Cys Pro Gln Pro Lys Glu Lys Cys Pro Lys Tyr Leu Leu Gly Arg
            20                  25                  30

Xaa Arg Arg Lys Arg Xaa Arg Tyr Pro Trp Trp Arg Xaa Lys His Arg
        35                  40                  45

Arg Trp
    50


<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid

<400> SEQUENCE: 69

Lys Xaa Lys Lys Gln Gln Gly Lys Lys Lys His Arg
1               5                   10


<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine

<400> SEQUENCE: 70

Lys Lys Lys Lys Lys Gln Ala Lys Lys Lys His Arg Trp Pro Met Gly
1               5                   10                  15


<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (17)..(17)
<223> OTHER INFORMATION: Aminohexanoic acid

<400> SEQUENCE: 71

Lys Lys Lys Lys Asn Gln Ala Lys Lys Lys His Arg Trp Pro Met Lys
1               5                   10                  15

Xaa Cys Pro Gln
```

20

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine

<400> SEQUENCE: 72

His Lys Lys Lys Lys Gln Ala Lys Lys Lys His Arg Trp Pro
1 5 10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (8)..(8)
<223> OTHER INFORMATION: Aminohexanoic acid

<400> SEQUENCE: 73

Lys Xaa Lys His Gln Gln Gln Xaa Lys
1 5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (4)..(4)
<223> OTHER INFORMATION: Aminohexanoic acid

<400> SEQUENCE: 74

Lys Xaa Lys Xaa Thr
1 5

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)

<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 75

Lys Lys Lys Lys Lys Gln Ala Lys Lys Lys His Arg Trp Pro Lys Xaa
1 5 10 15

Xaa Cys

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 76

Lys Lys Lys Lys Lys Cys Ala Lys Lys Lys His Arg Trp Pro Lys Xaa
1 5 10 15

Xaa Gln

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Aminohexanoic acid
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (17)..(17)
<223> OTHER INFORMATION: Aminohexanoic acid

<400> SEQUENCE: 77

Lys Lys Lys Xaa Lys Gln Ala Lys Lys Lys His Arg Trp Pro Lys Lys
1 5 10 15

Xaa Cys

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Aminohexanoic acid
<220> FEATURE:
<221> NAME/KEY: MOD_RES
<222> LOCATION: (13)..(13)
<223> OTHER INFORMATION: Aminohexanoic acid
<220> FEATURE:
<221> NAME/KEY: MOD_RES
<222> LOCATION: (17)..(17)
<223> OTHER INFORMATION: Beta-alanine

<400> SEQUENCE: 78

Lys Cys His Lys Xaa Lys Trp Lys Lys Pro Lys Arg Xaa Lys Gln Lys
1 5 10 15

Ala Lys

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 79

Lys Lys Lys Lys Lys Gln Cys Lys Lys Lys His Arg Trp Pro Lys Xaa
1 5 10 15

Xaa Cys

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 80

Lys Lys Lys Lys Lys Gln Ala Lys Lys Lys His Arg Trp Pro Lys Xaa
1 5 10 15

Xaa Gly

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:

<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (18)..(18)
<223> OTHER INFORMATION: Aminohexanoic acid
<220> FEATURE:
<221> NAME/KEY: MOD_RES
<222> LOCATION: (19)..(19)
<223> OTHER INFORMATION: Aminohexanoic acid

<400> SEQUENCE: 81

Lys Lys Lys Lys Lys Gln Ala Lys Lys Lys His Arg Trp Pro Met Gly
1 5 10 15

Lys Xaa Xaa Cys
20

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 82

His Lys Lys Lys Lys Gln Ala Lys Lys Lys His Arg Trp Pro Lys Xaa
1 5 10 15

Xaa Cys

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: Aminohexanoic acid
<220> FEATURE:
<221> NAME/KEY: MOD_RES
<222> LOCATION: (12)..(12)
<223> OTHER INFORMATION: Aminohexanoic acid

<400> SEQUENCE: 83

Lys Xaa Lys His Gln Gln Gln Xaa Lys Lys Xaa Xaa Cys
1 5 10

```
<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (4)..(4)
<223> OTHER INFORMATION: Aminohexanoic acid
<220> FEATURE:
<221> NAME/KEY: MOD_RES
<222> LOCATION: (7)..(7)
<223> OTHER INFORMATION: Aminohexanoic acid
<220> FEATURE:
<221> NAME/KEY: MOD_RES
<222> LOCATION: (8)..(8)
<223> OTHER INFORMATION: Aminohexanoic acid

<400> SEQUENCE: 84

Lys Xaa Lys Xaa Thr Lys Xaa Xaa Cys
1               5


<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Aminohexanoic acid
<220> FEATURE:
<221> NAME/KEY: MOD_RES
<222> LOCATION: (23)..(23)
<223> OTHER INFORMATION: Aminohexanoic acid

<400> SEQUENCE: 85

Ala Leu Trp Lys Thr Leu Leu Lys Lys Val Leu Lys Ala Pro Lys Lys
1               5                   10                  15

Lys Arg Lys Val Lys Xaa Xaa Cys
            20


<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aminohexanoic acid
<220> FEATURE:
<221> NAME/KEY: MOD_RES
<222> LOCATION: (19)..(19)
<223> OTHER INFORMATION: Aminohexanoic acid

<400> SEQUENCE: 86

Arg Gln Ile Lys Ile Trp Phe Gln Asn Arg Arg Met Lys Trp Lys Lys
1               5                   10                  15

Lys Xaa Xaa Cys
            20
```

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine

<400> SEQUENCE: 87

Lys Lys Lys Lys Lys Gln Ala Lys Lys Lys His Arg Trp Pro
1               5                   10

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 88

Lys Lys Lys Lys Lys Gln Ala Lys Lys Lys His Arg Trp Pro Lys Xaa
1               5                   10                  15

Xaa Cys Cys Cys
            20

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 89

Lys Lys Lys Lys Lys Gln Ala Lys Lys Lys His Arg Trp Ala Lys Xaa
1               5                   10                  15

Xaa Cys

<210> SEQ ID NO 90
<211> LENGTH: 8
<212> TYPE: PRT

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid

<400> SEQUENCE: 90

Lys Xaa Lys His Gln Gln Gly Pro
1 5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Aminohexanoic acid

<400> SEQUENCE: 91

Lys Xaa Lys His Gln Gln Gly Lys Lys Thr
1 5 10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

His Lys Lys Lys Gln Gln Gly Lys Lys Lys His Arg Trp
1 5 10

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine

<400> SEQUENCE: 93

Lys Lys Lys Lys Lys Gln Ala Lys Lys Lys His Arg Trp Pro Met
1 5 10 15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Lys Lys Lys Lys Lys Gln Gly Lys Lys His Arg Trp Pro Met Gly Gly
1 5 10 15

```
<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (17)..(17)
<223> OTHER INFORMATION: Aminohexanoic acid

<400> SEQUENCE: 95

Lys Lys Lys Lys Asn Gln Ala Lys Lys Lys His Arg Trp Pro Met Lys
1               5                   10                  15

Xaa Cys Pro


<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 96

Lys Lys Lys Lys Lys Gln Ala Lys Lys Lys His Arg Trp Pro Lys Xaa
1               5                   10                  15

Xaa Ala


<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid

<400> SEQUENCE: 97

Lys Lys Lys Lys Lys Gln Ala Lys Lys Lys His Arg Trp Pro Lys Xaa
1               5                   10                  15

Ala Cys


<210> SEQ ID NO 98
<211> LENGTH: 18
<212> TYPE: PRT
```

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (17)..(17)
<223> OTHER INFORMATION: Aminohexanoic acid

<400> SEQUENCE: 98

Lys Lys Lys Lys Lys Gln Ala Lys Lys Lys His Arg Trp Pro Lys Ala
1 5 10 15

Xaa Cys

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 99

Lys Lys Lys Lys Lys Gln Ala Lys Lys Lys His Arg Trp Pro Ala Xaa
1 5 10 15

Xaa Cys

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 100

Lys Ala Lys Lys Lys Gln Ala Lys Lys Lys His Arg Trp Pro Lys Xaa
1 5 10 15

Xaa Cys

<210> SEQ ID NO 101
<211> LENGTH: 18

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 101

Lys Lys Lys Lys Lys Gln Ala Lys Ala Lys His Arg Trp Pro Lys Xaa
1               5                   10                  15

Xaa Cys

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 102

Lys Lys Lys Ala Lys Gln Ala Lys Lys Lys His Arg Trp Pro Lys Xaa
1               5                   10                  15

Xaa Cys

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 103

Lys Lys Lys Ala Lys Gln Ala Lys Ala Lys His Arg Trp Pro Lys Xaa
1               5                   10                  15

Xaa Cys

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 104

Lys Ala Lys Ala Lys Gln Ala Lys Lys Lys His Arg Trp Pro Lys Xaa
1 5 10 15

Xaa Cys

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Beta-alanine
<220> FEATURE:
<221> NAME/KEY: MOD_RES
<222> LOCATION: (16)..(16)
<223> OTHER INFORMATION: Aminohexanoic acid
<220> FEATURE:
<221> NAME/KEY: MOD_RES
<222> LOCATION: (17)..(17)
<223> OTHER INFORMATION: Aminohexanoic acid

<400> SEQUENCE: 105

Lys Ala Lys Ala Lys Gln Ala Lys Ala Lys His Arg Trp Pro Lys Xaa
1 5 10 15

Xaa Cys

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Beta-alanine

<400> SEQUENCE: 106

Ala Cys Ala Ala Cys Ala
1 5

<210> SEQ ID NO 107
<211> LENGTH: 6

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Pro Ser Thr Gly Gly
1               5


<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Gly Gly
1               5


<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 109

His His His His His His
1               5
```

DESIGNING ANTISENSE OLIGONUCLEOTIDE DELIVERY PEPTIDES BY INTERPRETABLE MACHINE LEARNING

RELATED APPLICATIONS

This application claims priority to U.S. Provisional Patent Application No. 62/965,555, filed Jan. 24, 2020, and U.S. Provisional Patent Application 63/134,405, filed Jan. 6, 2021, the contents of which is incorporated herein by reference in its entirety.

REFERENCE TO ELECTRONICALLY FILED SEQUENCE LISTING

The Sequence Listing associated with this application is provided in text format, and is hereby incorporated by reference into the specification. The name of the text file containing the Sequence Listing is 4140_1040002_SequenceListing_ST25.txt. The text file is 48,421 bytes, was created on Mar. 25, 2025, and is being submitted electronically.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing, or translation through any one of a number of antisense mechanisms. The sequence specificity of antisense compounds makes them attractive as tools for target validation and gene functionalization, as well as therapeutics to selectively modulate the expression of genes involved in disease.

Although significant progress has been made in the field of antisense technology, there remains a need in the art for oligonucleotides and peptide-oligonucleotide-conjugates having improved antisense or antigene performance.

SUMMARY

Provided herein are peptide-oligonucleotide-conjugates comprising an oligonucleotide covalently bound to a peptide. Also provided herein are methods of treating a disease in a subject in need thereof, comprising administering to the subject a peptide-oligonucleotide-conjugate described herein. Also provided herein is a method for identifying one or more cell-penetrating peptides having optimal activity using machine learning.

Accordingly, in one aspect, provided herein is a peptide-oligonucleotide conjugate of Formula I:

(I)

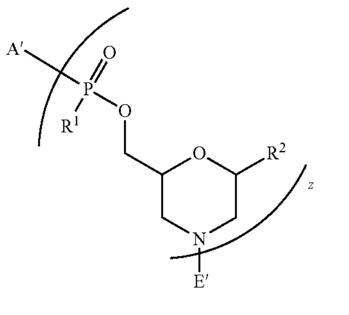

or a pharmaceutically acceptable salt thereof, wherein:

A' is selected from —N(H)$CH_2C(O)NH_2$, —N($C_{1-6}$-alkyl)$CH_2C(O)NH_2$,

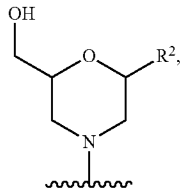 and 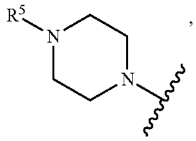, wherein $R^5$ is —C(O)(O-alkyl)$_x$-OH, wherein x is 3-10 and each alkyl group is, independently at each occurrence, $C_{2-6}$-alkyl, or $R^5$ is selected from —C(O)$C_{1-6}$-alkyl, trityl, monomethoxytrityl, —($C_{1-6}$-alkyl)-$R^6$, —($C_{1-6}$-heteroalkyl)-$R^6$, aryl-$R^6$, heteroaryl-$R^6$, —C(O)O—($C_{1-6}$-alkyl)-$R^6$, —C(O)O-aryl-$R^6$, —C(O)O— heteroaryl-$R^6$, and

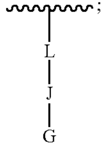;

wherein $R^6$ is selected from OH, SH, and $NH_2$, or $R^6$ is O, S, or NH, each of which are covalently-linked to a solid support;

each $R^1$ is independently selected from OH and —N($R^3$)($R^4$), wherein each $R^3$ and $R^4$ are, independently at each occurrence, —$C_{1-6}$-alkyl;

each $R^2$ is independently, at each occurrence, selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, —$C_{1-6}$-alkyl, —C(O)$C_{1-6}$-alkyl, benzoyl, stearoyl, trityl, monomethoxytrityl, dimethoxytrityl, trimethoxytrityl,

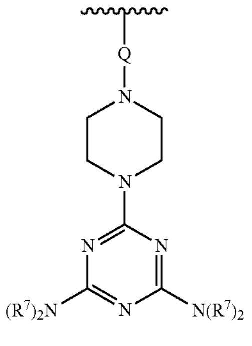 and 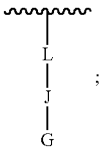;

wherein

Q is —C(O)$(CH_2)_6$C(O)— or —C(O)$(CH_2)_2S_2(CH_2)_2$C(O)—;

$R^7$ is $—(CH_2)_2OC(O)N(R^8)_2$, wherein $R^3$ is $—(CH_2)_6NHC(═NH)NH_2$;

L is $—C(O)(CH_2)_{1-6}—C_{7-15}$-heteroaromatic-$(CH_2)_{1-6}C(O)—$, wherein L is covalently-linked by an amide bond to J;

J is a carrier peptide;

G is selected from H, $—C(O)C_{1-6}$-alkyl, benzoyl, and stearoyl, wherein G is covalently-linked to J;

wherein at least one of the following conditions is true:

1) A' is

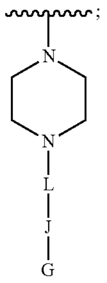

or 2) E' is

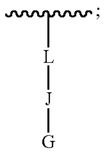

and wherein the carrier peptide J is selected from the following sequences:

| | |
|---|---|
| MACH 1 (SEQ ID NO: 57) | ALKBRSAAKAVRWPKKKIKQASKKVAKYALXXXRKKKAASKXWLQLHWPRW |
| MACH 2 (SEQ ID NO: 58) | PPLRNAKKKNLKNNLKMDPKFTKKVKQGALKLNRRKKNRGPKGPXKHWTT |
| MACH 3 (SEQ ID NO: 59) | QKKRKSKANKKNWPKGKLSIHAKDYKQGPKAKXRKQRXR |
| MACH 4 (SEQ ID NO: 60) | KKGKKQNKKKHRWPKKKVPQPKKMFKQGABXRX |
| MACH 5 (SEQ ID NO: 61) | AKKKIAKAKKHRGPNBGIHAPVSKIKDPLKXXX |
| MACH 6 (SEQ ID NO: 62) | ALKBRSAAKAVRWPKKAIKQASKKVAKYALKXXRKKKAASKXWLQLHWPRW |
| MACH 7 (SEQ ID NO: 63) | XKHPXAVQBAARAWKVPAAALWKKKRLKKSSKQKKKWLWKARSAXKYXRLI |
| MACH 8 (SEQ ID NO: 64) | BKGKNLLAKIRRGPNGGNBQGSQGYLLYLLXRXRRQRXXYPWWRXKHXRWXXRXRGHXRRRRQXLKPDRXRGGKGSVS |

-continued

| | |
|---|---|
| MACH 9 (SEQ ID NO: 65) | KKKKNLNBKSRRGPNGGALQPSQGYLQPLNXRXRRQRXXYPWWRXKHXRWRXRYHXRRRRQXLKPG |
| MACH 11 (SEQ ID NO: 66) | TSNLKLHLAPPVKKKALKKPLYKAKKKKKVVSPTWXTDQEW |
| MACH 12 (SEQ ID NO: 67) | KGGKNLAKKIRRGPNGGALQPSQGYLLYLBXRXRRQRXXGPXWRXKHXRWXXXXXRPTHXRRRRQXLCPGRXRPCRGSVS |
| MACH 13 (SEQ ID NO: 68) | AKKKKLGBKALRWPNGKCPQPKEKCPKYLLGRXRRKRXRYPWWRXKHRRW |
| P1 (MACH 14) (SEQ ID NO: 69) | KXKKQQGKKKHR |
| P2 (MACH 15) (SEQ ID NO: 70) | KKKKKQBKKKHRWPMG |
| P3 (MACH 16) (SEQ ID NO: 71) | KKKKNQBKKKHRWPMKXCPQ |
| P4 (MACH 17) (SEQ ID NO: 72) | HKKKKQBKKKHRWP |
| P5 (MACH 18) (SEQ ID NO: 73) | KXKHQQQXK |
| P6 (MACH 19) (SEQ ID NO: 74) | KXKXT |
| P7 (MACH 20) (SEQ ID NO: 75) | KKKKKQBKKKHRWPKXXC |
| P8 (SEQ ID NO: 76) | KKKKKCBKKKHRWPKXXQ |
| P9 (SEQ ID NO: 77) | KKKXKQBKKKHRWPKKXC |
| P10 (SEQ ID NO: 78) | KCHKXKWKKPKRXKQKBK |
| P11 (SEQ ID NO: 79) | KKKKKQCKKKHRWPKXXC |
| P12 (SEQ ID NO: 80) | KKKKKQBKKKHRWPKXXG |
| P13 (SEQ ID NO: 81) | KKKKKQBKKKHRWPMGKXXC |

-continued

| | |
|---|---|
| P14 (SEQ ID NO: 82) | HKKKKQBKKKHRWPKXXC |
| P15 (SEQ ID NO: 83) | KXKHQQQXKKXXC |
| P16 (SEQ ID NO: 84) | KXKXTKXXC |
| P17 (SEQ ID NO: 26) | ALWKTLLKKVLKAPKKKRKV |
| P18 (SEQ ID NO: 85) | ALWKTLLKKVLKAPKKKRKVKXXC |
| P19 (SEQ ID NO: 45) | RQIKIWFQNRRMKWKK |
| P20 (SEQ ID NO: 86) | RQIKIWFQNRRMKWKKKXXC |
| P21 (SEQ ID NO: 87) | KKKKKQBKKKHRWP |
| P22 (SEQ ID NO: 88) | KKKKKQBKKKHRWPKXXCCC |
| P23 (SEQ ID NO: 89) | KKKKKQBKKKHRWAKXXC |

wherein X is 6-amino hexanoic acid, B is β-alanine, and C is covalently bound to another C by $L^1$;

wherein $L^1$ is

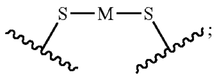

M is

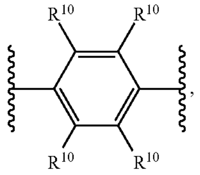

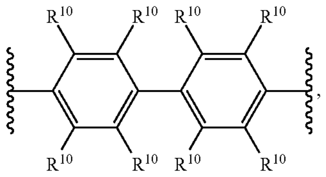

or

-continued

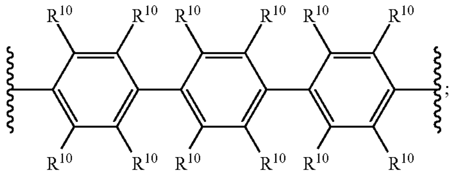

$R^{10}$ is independently at each occurrence H or a halogen.

In another aspect, also provided herein is a compound of Formula II having the definitions provided above and wherein the carrier peptide J is selected from the following sequences:

| | |
|---|---|
| P24 (SEQ ID NO: 90) | KXKHQQGP |
| P25 (SEQ ID NO: 91) | KXKHQQGKKT |
| P26 (SEQ ID NO: 92) | HKKKQQGKKKHRW |
| P27 (SEQ ID NO: 93) | KKKKKQBKKKHRWPM |
| P28 (SEQ ID NO: 94) | KKKKKQGKKHRWPMGG |
| P29 (SEQ ID NO: 95) | KKKKNQBKKKHRWPMKXCP |
| P30 (SEQ ID NO: 96) | KKKKKQBKKKHRWPKXXA |
| P31 (SEQ ID NO: 97) | KKKKKQBKKKHRWPKXAC |
| P32 (SEQ ID NO: 98) | KKKKKQBKKKHRWPKAXC |
| P33 (SEQ ID NO: 99) | KKKKKQBKKKHRWPAXXC |
| P34 (SEQ ID NO: 100) | KAKKKQBKKKHRWPKXXC |
| P35 (SEQ ID NO: 101) | KKKKKQBKAKHRWPKXXC |
| P36 (SEQ ID NO: 102) | KKKAKQBKKKHRWPKXXC |
| P37 (SEQ ID NO: 103) | KKKAKQBKAKHRWPKXXC |
| P38 (SEQ ID NO: 104) | KAKAKQBKKKHRWPKXXC |

-continued

| | |
|---|---|
| P39 (SEQ ID NO: 105) | KAKAKQBKAKHRWPKXXC |
| P40 (SEQ ID NO: 87) | KKKKKQBKKKHRWP |

In one embodiment, the peptide-oligonucleotide-conjugate of Formula I is a peptide-oligonucleotide-conjugate of Formula Ia:

(Ia)

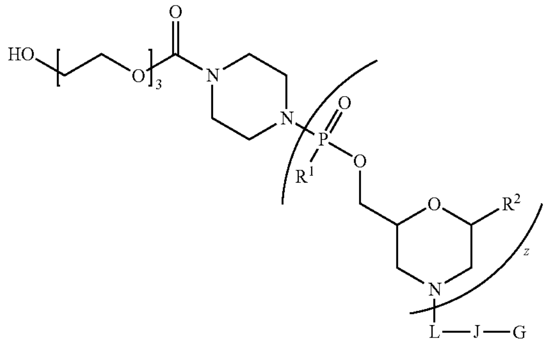

or a pharmaceutically acceptable salt thereof.

In another embodiment, the peptide-oligonucleotide-conjugate of Formula I is a peptide-oligonucleotide-conjugate of Formula Ib:

(Ib)

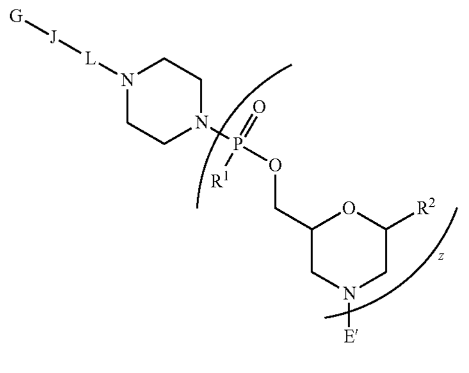

or a pharmaceutically acceptable salt thereof,

In still another aspect, provided herein is a method of treating a neuromuscular disease, comprising administering to the subject a peptide-oligonucleotide-conjugate of the present disclosure.

In another aspect, provided herein is a method for identifying one or more cell-penetrating peptides having optimal activity using machine learning, the method comprising:

a.) synthesizing a library of training oligonucleotide-cell-penetrating peptide conjugates;

b.) generating seed peptide sequences by training a nested long short-term memory (LSTM) recurrent neural network model using the synthesized library;

c.) predicting which peptide sequences from the generated seed peptide sequences have predetermined structure-activity relationships of amino acid residues; and identifying one or more optimal ones of the predicted peptide sequences using an activity predictor-genetic algorithm optimizer loop.

BRIEF DESCRIPTION OF THE FIGURES

FIG. 5 shows particular peptide sequences and names for the proof-of-concept experiments.

Shows heat maps disclosing the cell count multiplied by the mean fluorescence (FxC) which gives a single metric that captures the two most important parameters for a modular construct.

Figure 7:
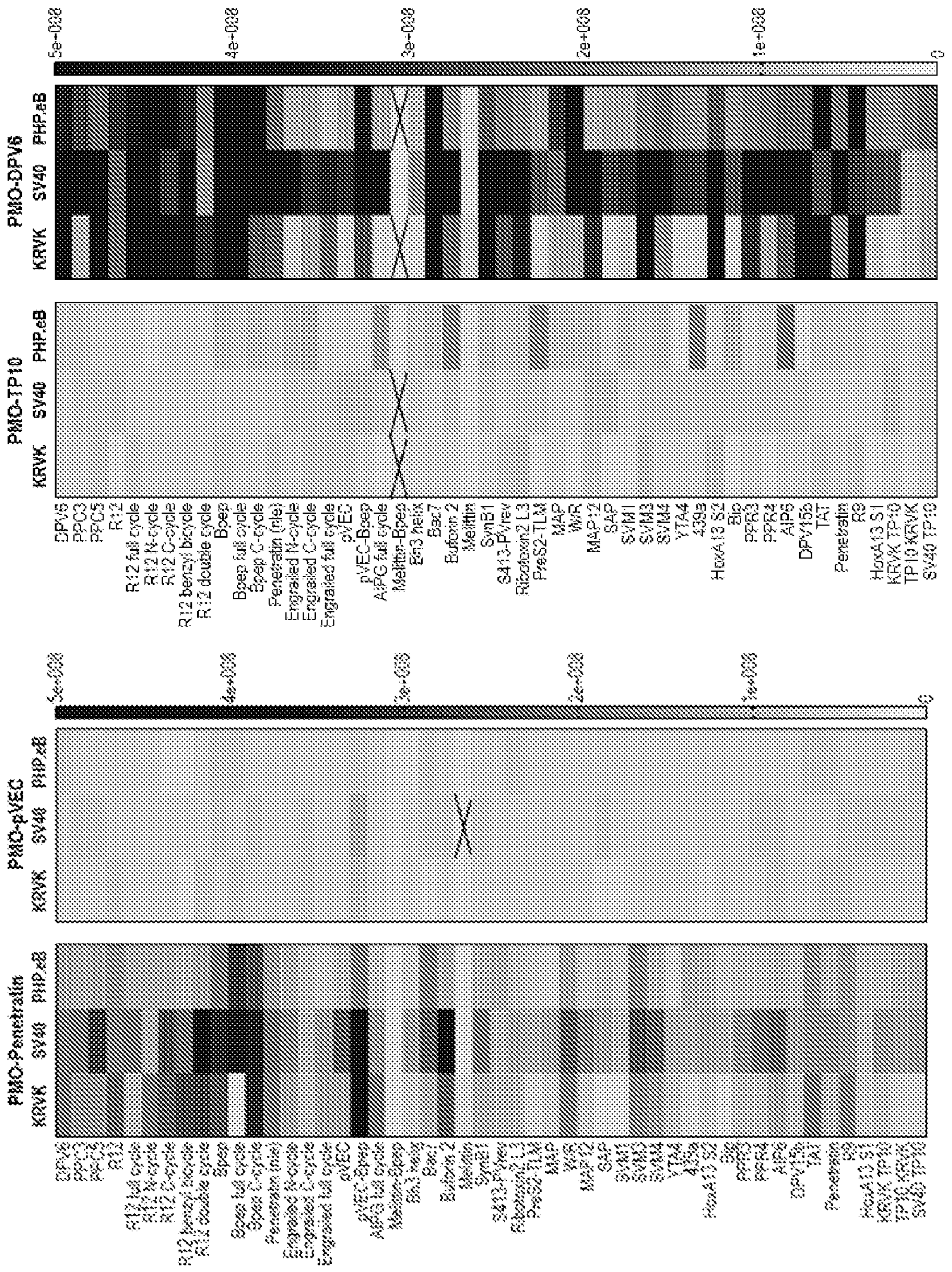

FIG. 7 shows heat maps disclosing the FxC of the 600 constructs tested in the HeLa-654 assay (n=1 replicate well). The most potent compound was PMO-DPV6-SV40-W/R, a combination of peptides that, prior to testing, would not have been predicted to be particularly notable. Boxes marked with an "X" are constructs in which the gated cell count was zero.

Figure 8:
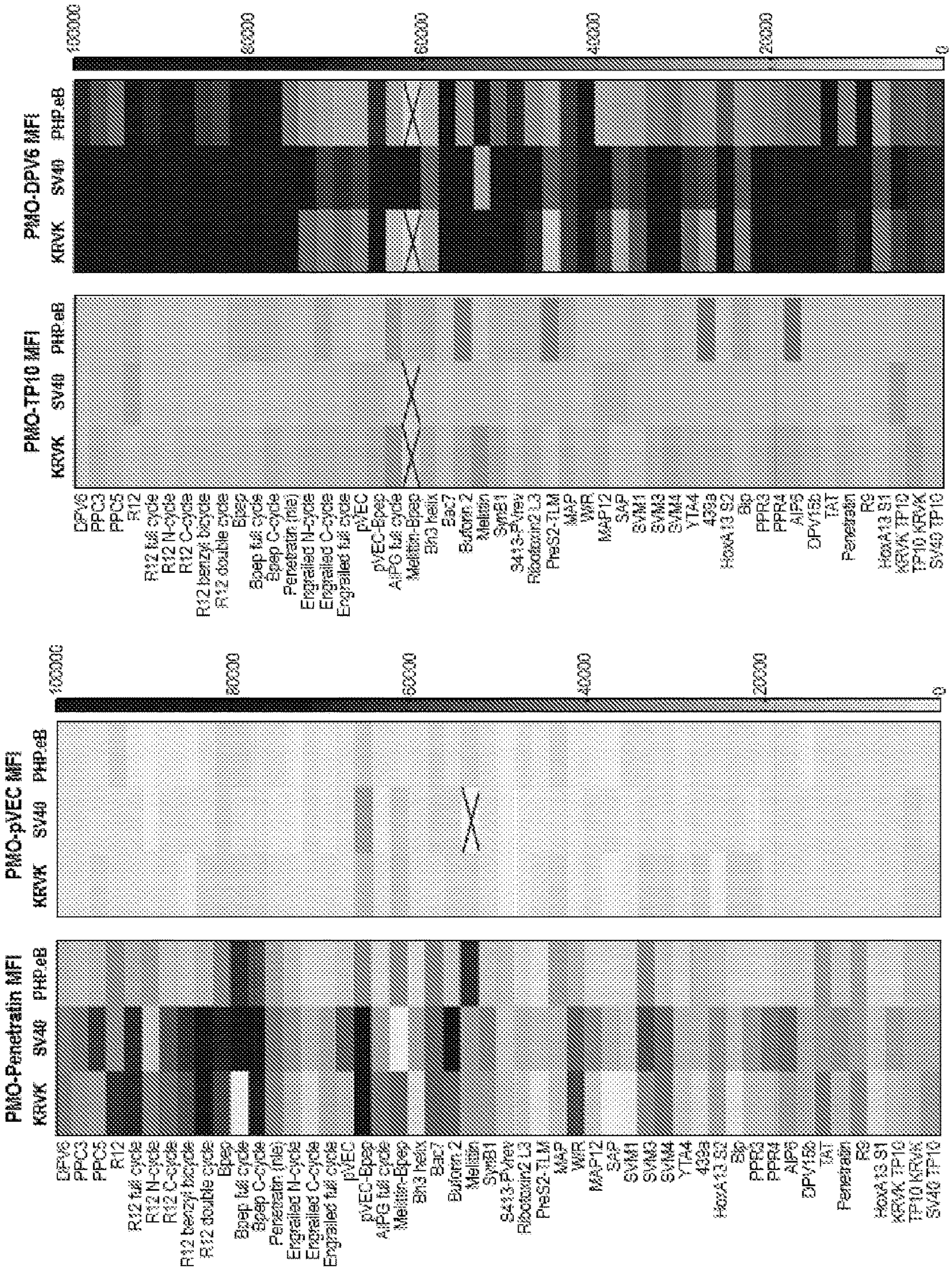

FIG. 8 shows heat maps disclosing the mean fluorescence intensity of the 600 constructs tested in the HeLa-654 assay (n=1 replicate well). Boxes marked with an "X" are constructs in which the gated cell count was zero.

Figure 9:
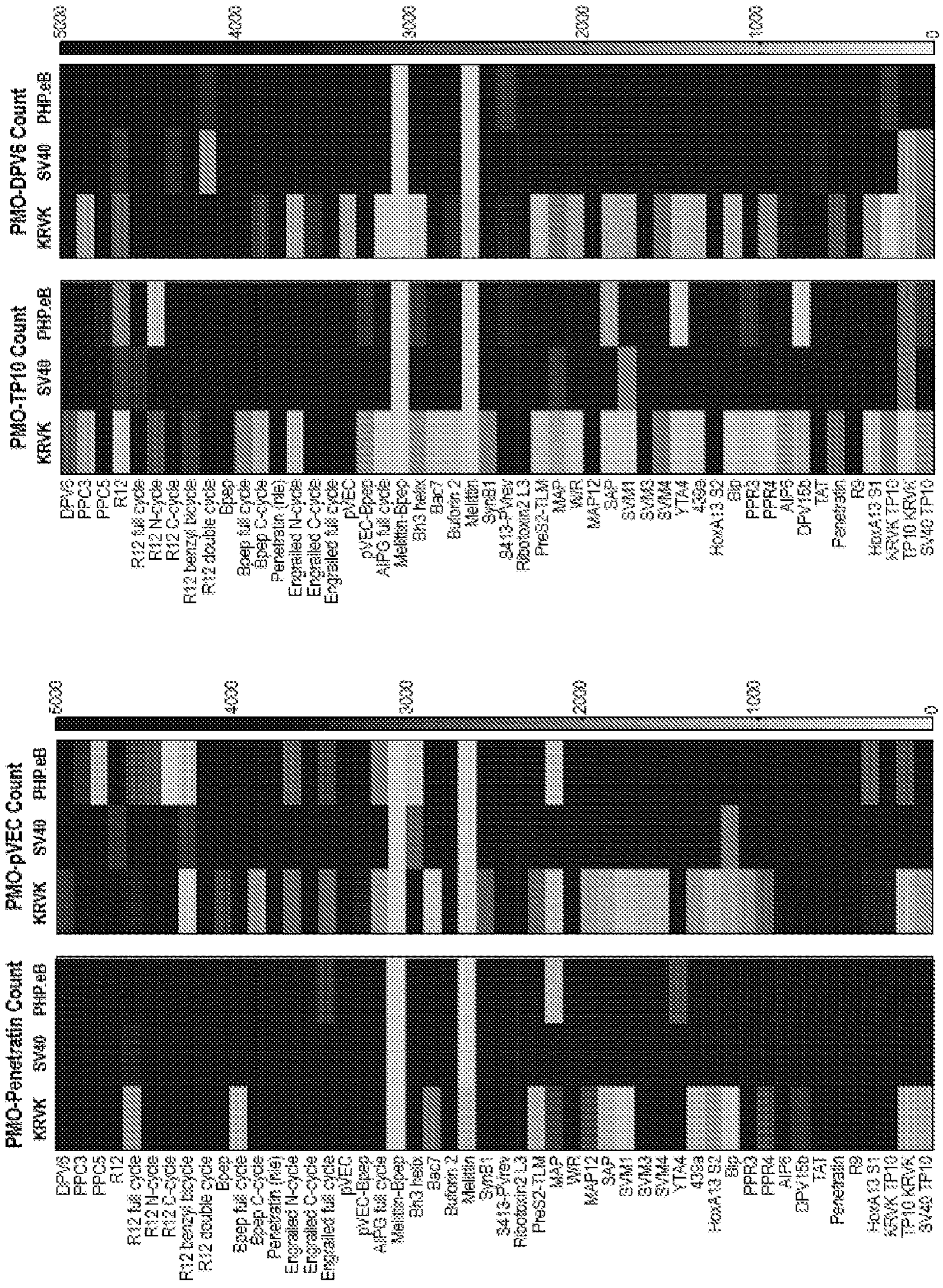

FIG. 9 shows heat maps disclosing the total cell count after treatment with 600 constructs (n=1 replicate well). The number of gated cells was capped at 5,000.

Figure 10:
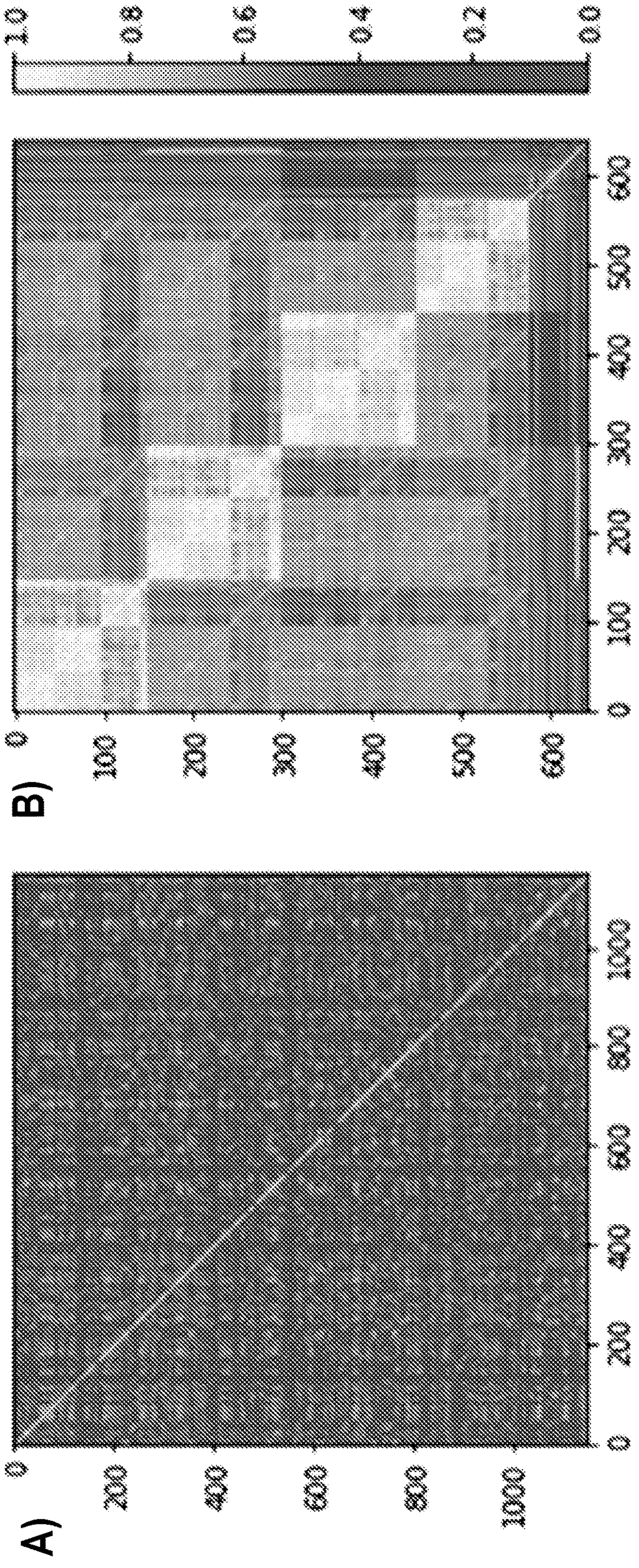

FIG. 10 shows Jaro-Winkler self-similarity of training sequences. A) shows sequences used in training of generator (Nested LSTM). B) shows sequences used in training of predictor (Convolutional Neural Network based models).

Figure 11:
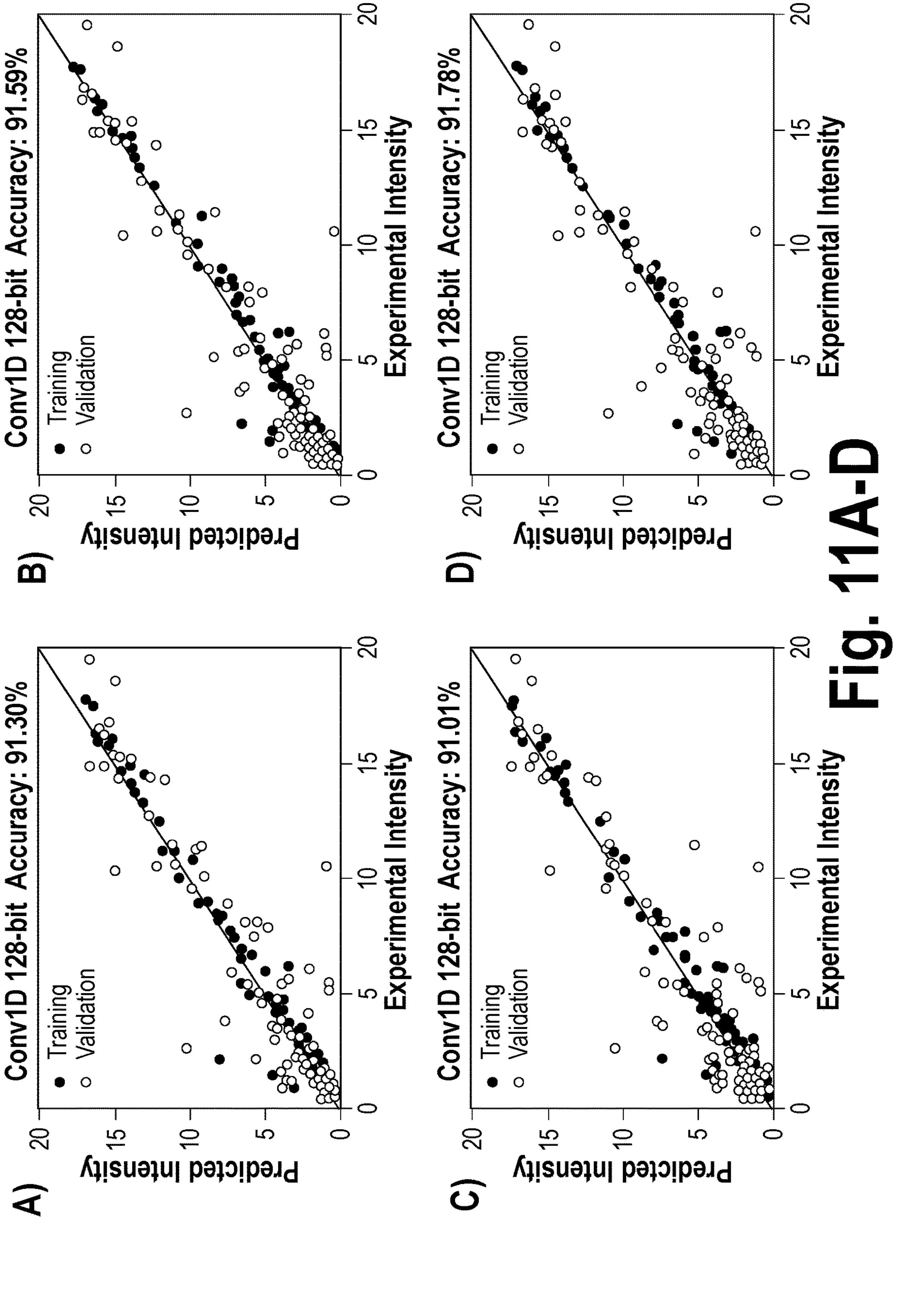

FIG. 11 shows predicted and experimental absolute intensity plots for training (80% of dataset), validation (20% of dataset), with percentage accuracy of the model within range of training values mentioned on the title. Models obtained after hyperparameter optimization for different representations with 128-bit fingerprints, A) Conv1D, B) Conv2D, C) Conv2D Macrocycles and D) DeConv2D.

Figure 12:
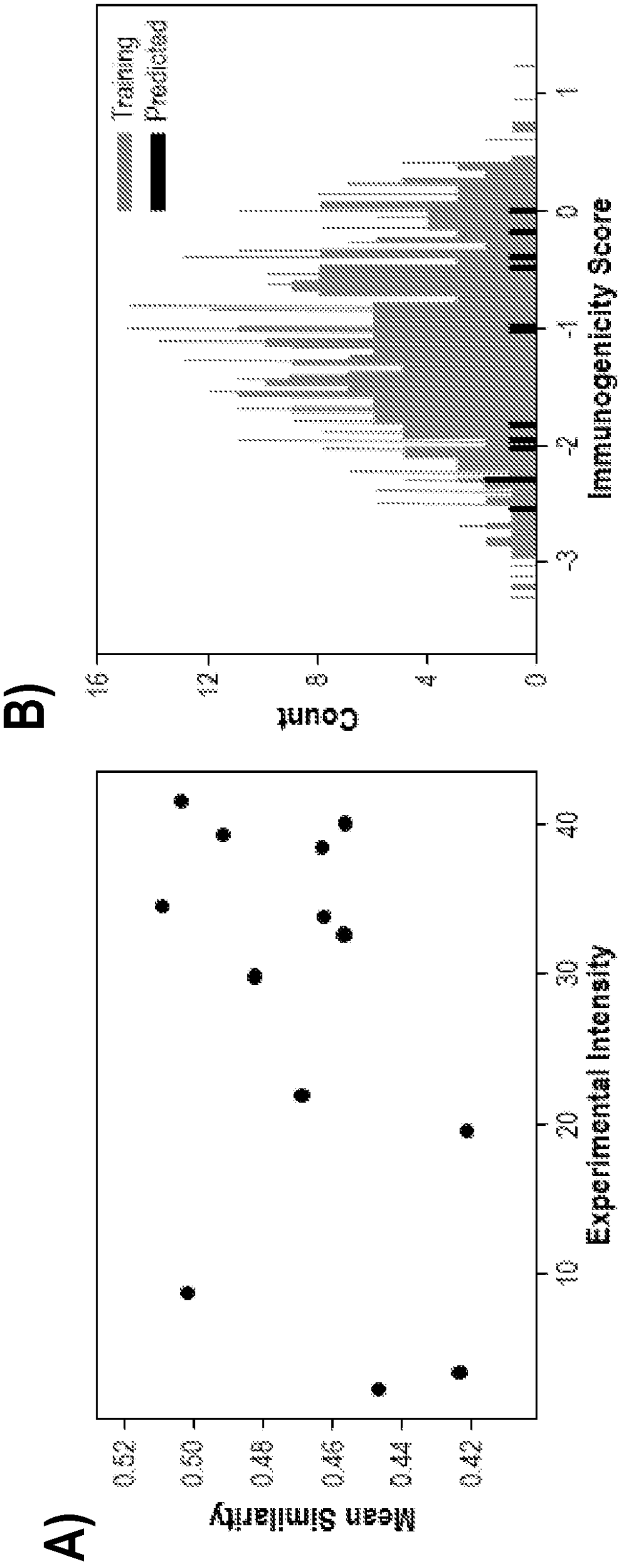

FIG. 12 shows A) Novelty of the predicted sequences against experimental intensity. B) Immunogenicity scores based on an online tool for predicting T cell epitopes (IEDB).

FIG. 13 shows gradient activations for sequences in training set, arranged in descending order of MFI—positive activation averaged over A) residue position from C-terminus, and B) fingerprint index; and negative activation averaged over C) residue position from C-terminus, and D) fingerprint index. Chemical substructures of pristine amino acids with fingerprint indices for E) Arginine, F) Lysine, G) Histidine and H) Aminohexanoic acid.

Figure 14:
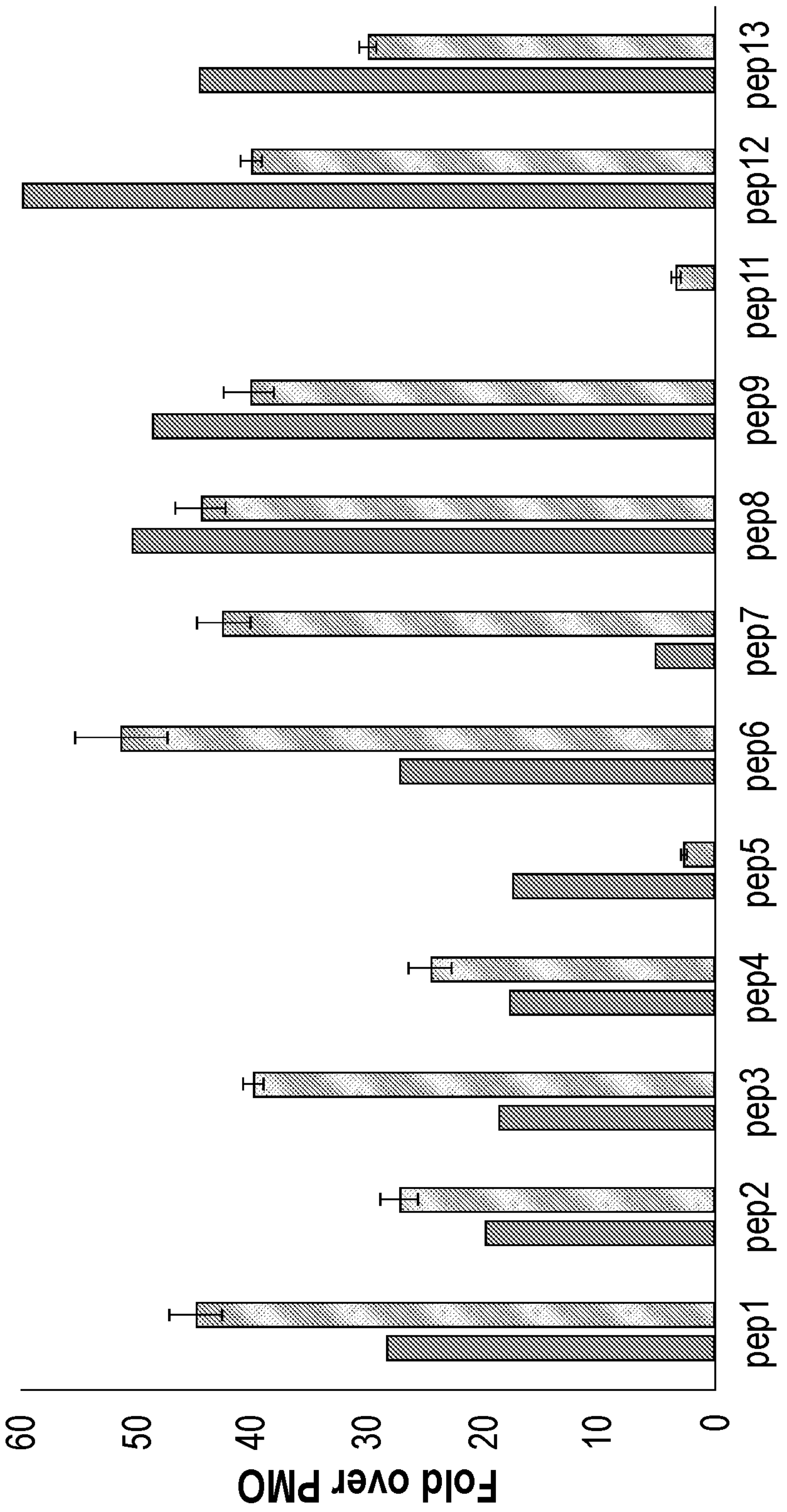
Figure 16A:
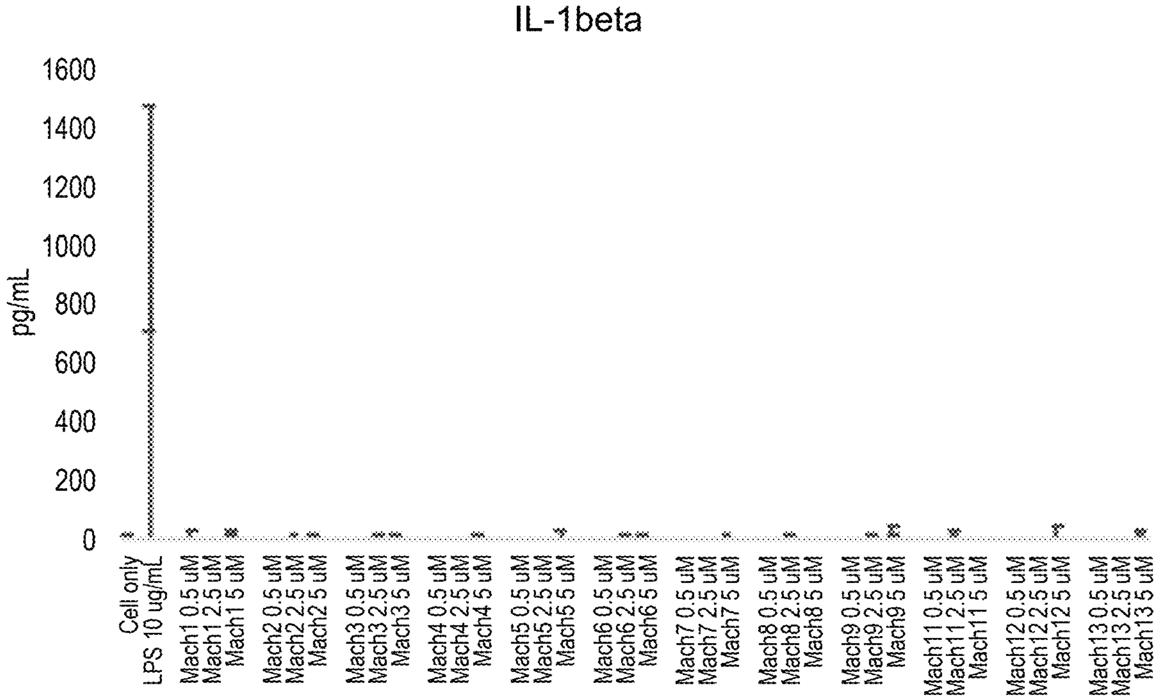
Figure 16B:
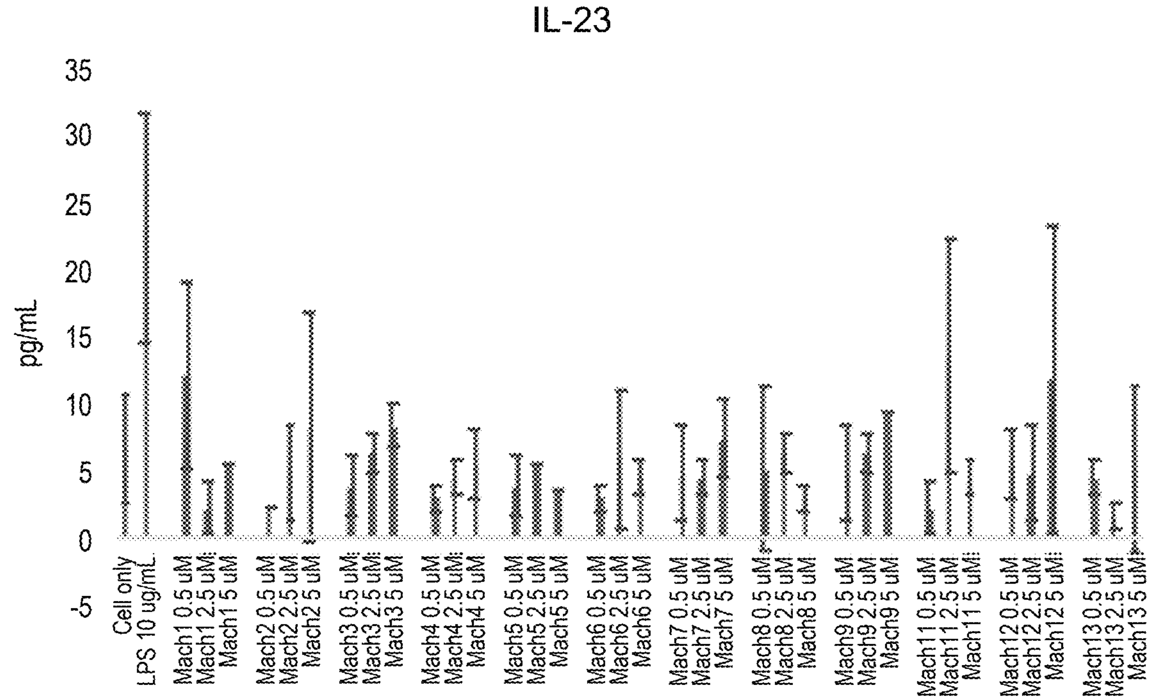
Figure 16C:
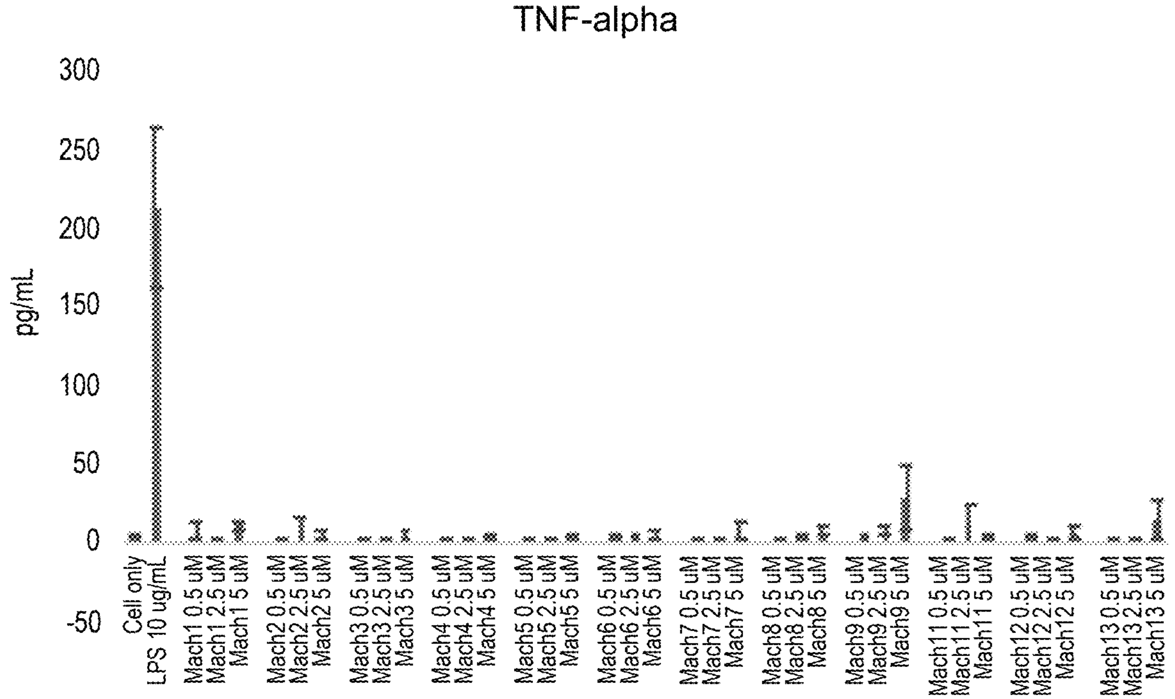
Figure 16D:
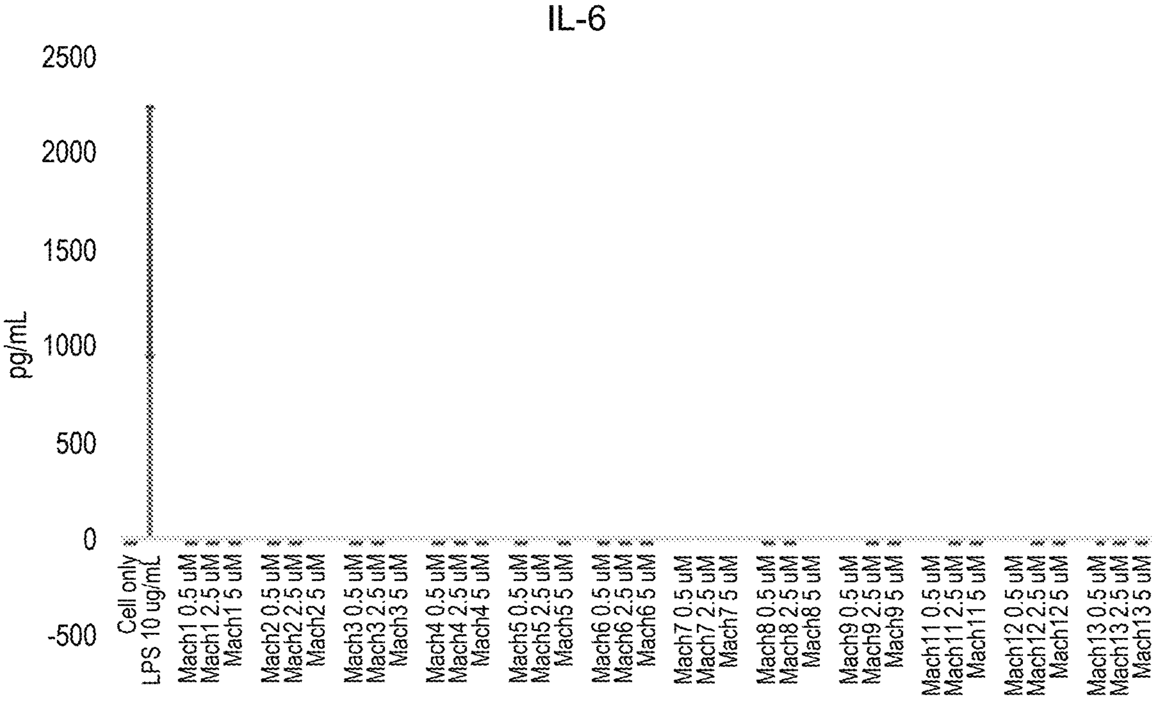
Figure 16E:
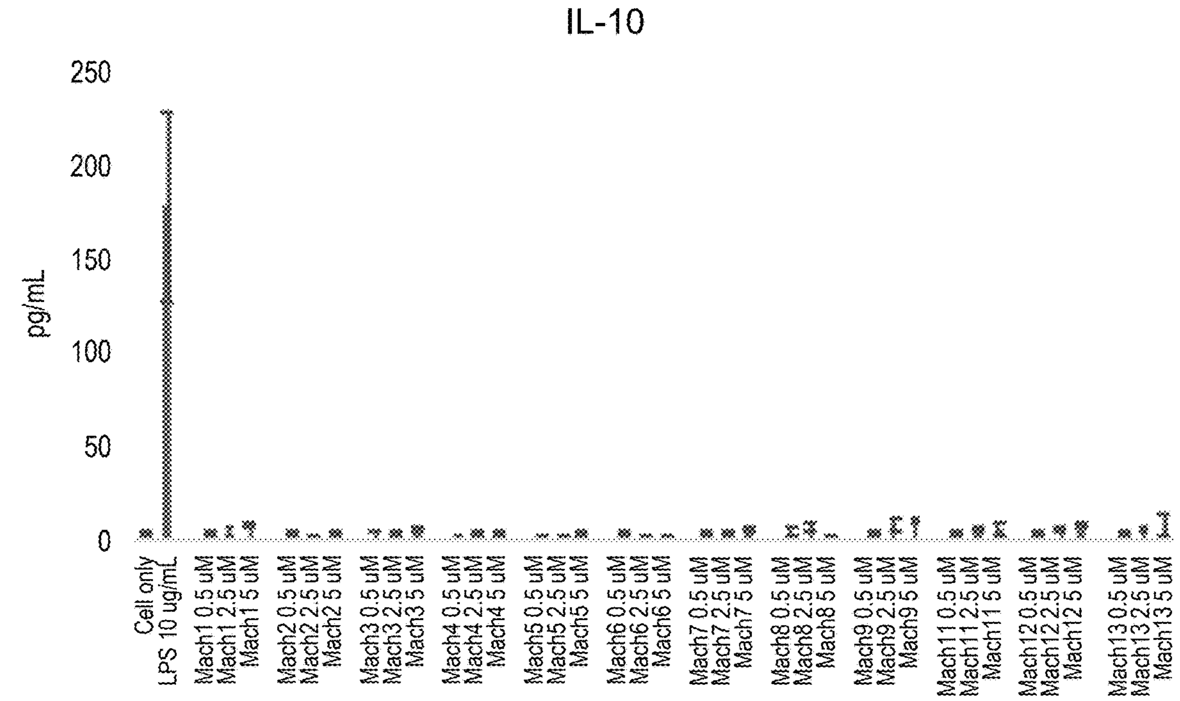
Figure 16F:
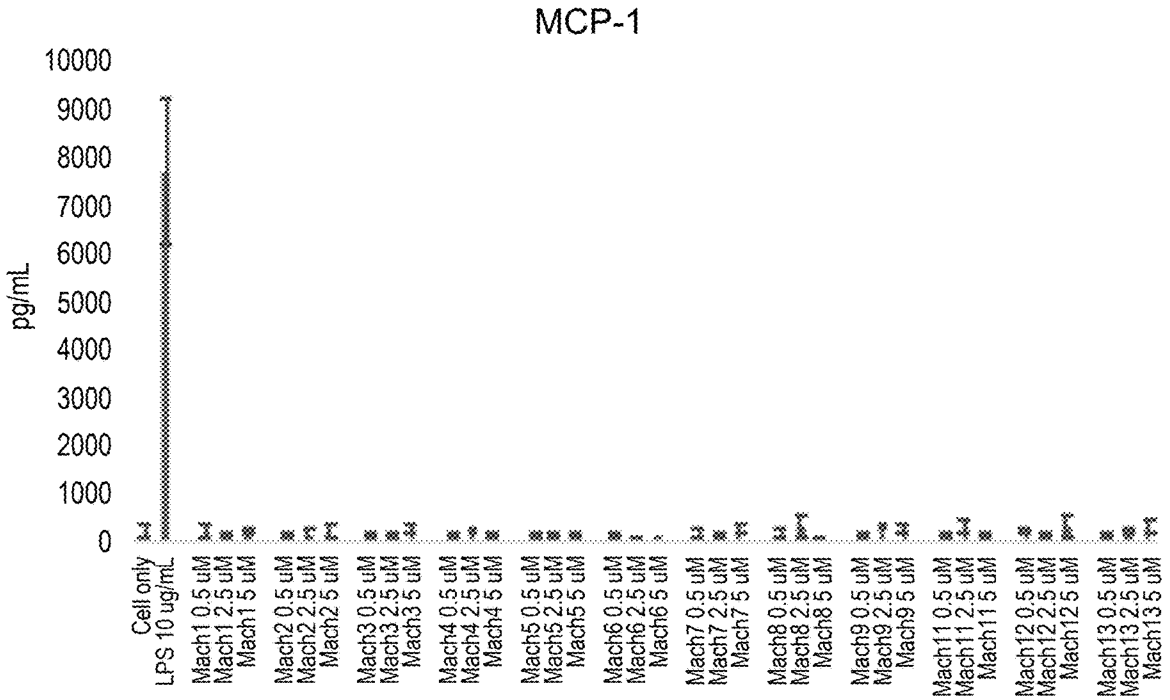
Figure 16G:
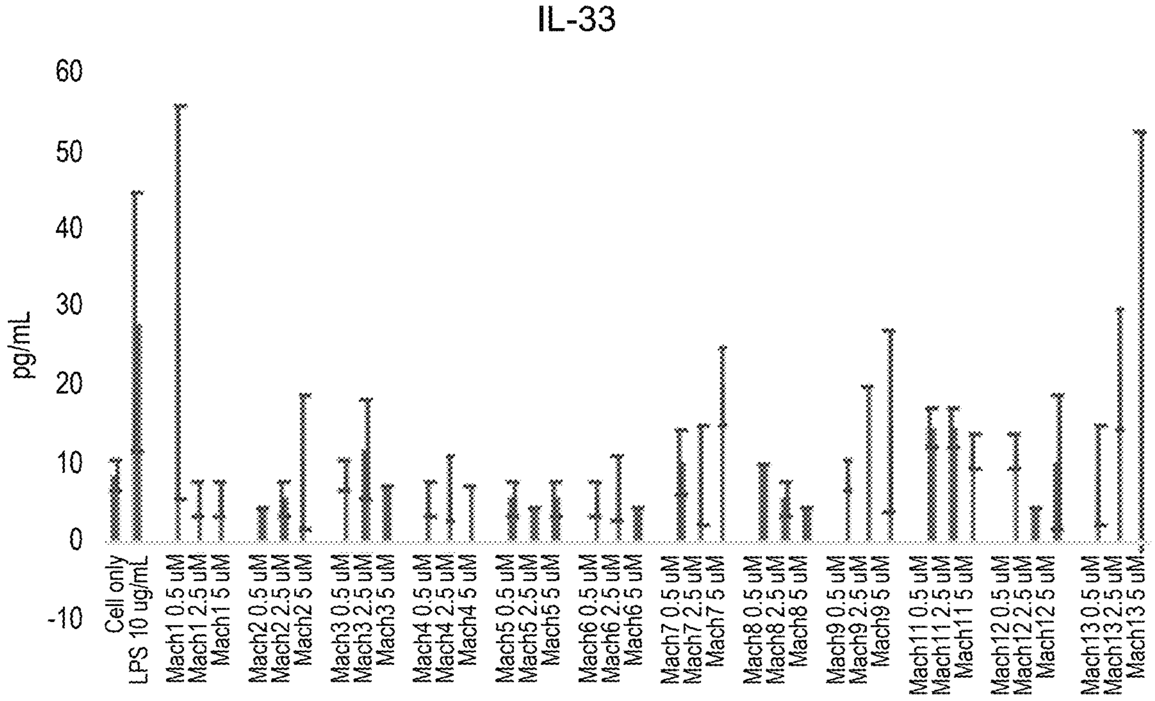
Figure 16H:
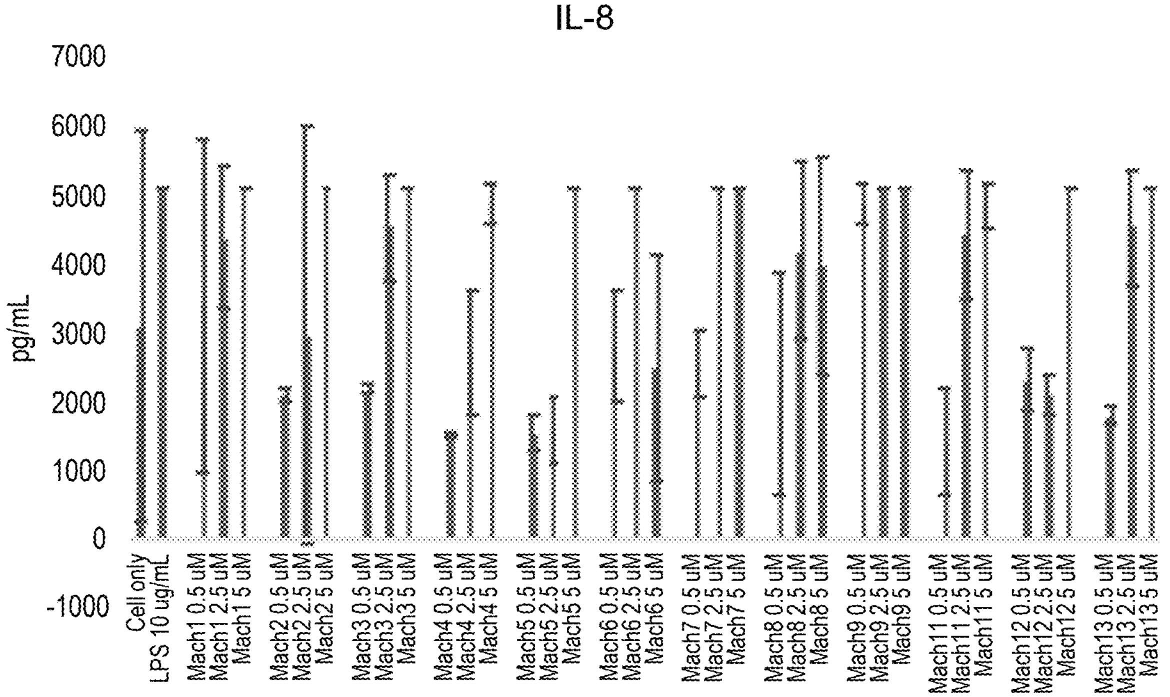
Figure 16I:
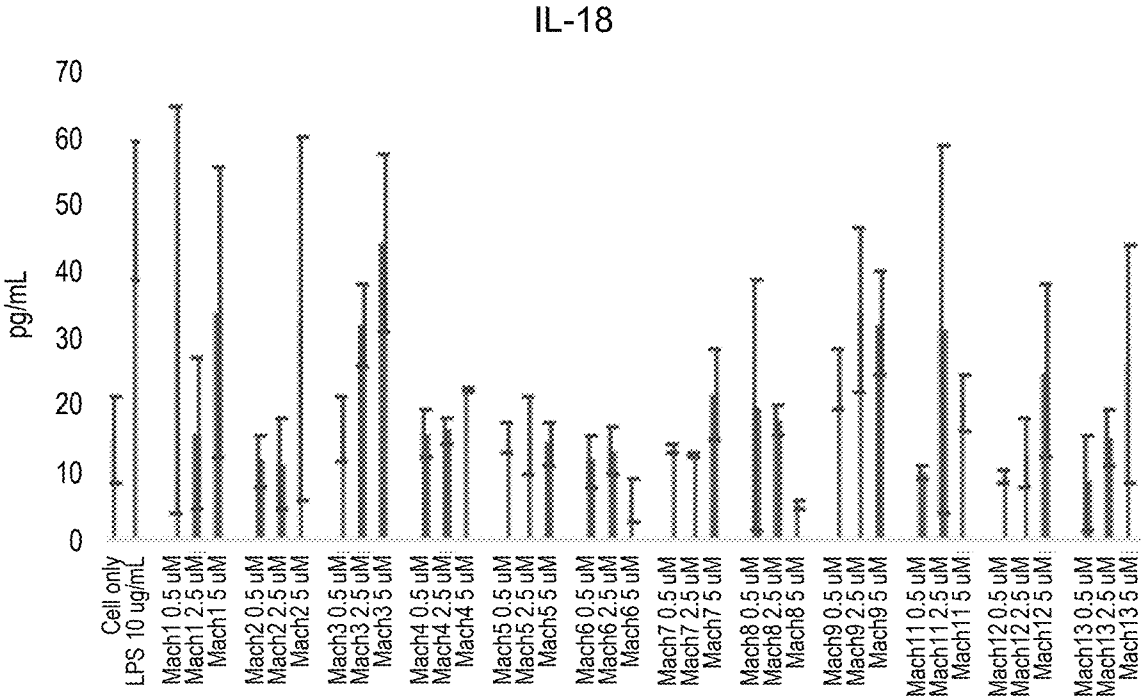

FIG. 14 shows Mach peptides enhance delivery of PMO by 40-50 fold as determined by an in vitro exon skipping assay. Experimental activity is comparable to predicted activity.

FIG. 15 shows that half of Mach CPPs are not toxic at 5 uM as determined by A) LDH release assay and B) MTT assay. Cytotoxicity is reported as a percentage of LDH release compared to cell lysate, and viability is reported as a percentage relative to no treatment.

FIG. 16 shows inflammation panel results of cytokines that were detected in human monocyte-derived macrophages.

Figure 17:
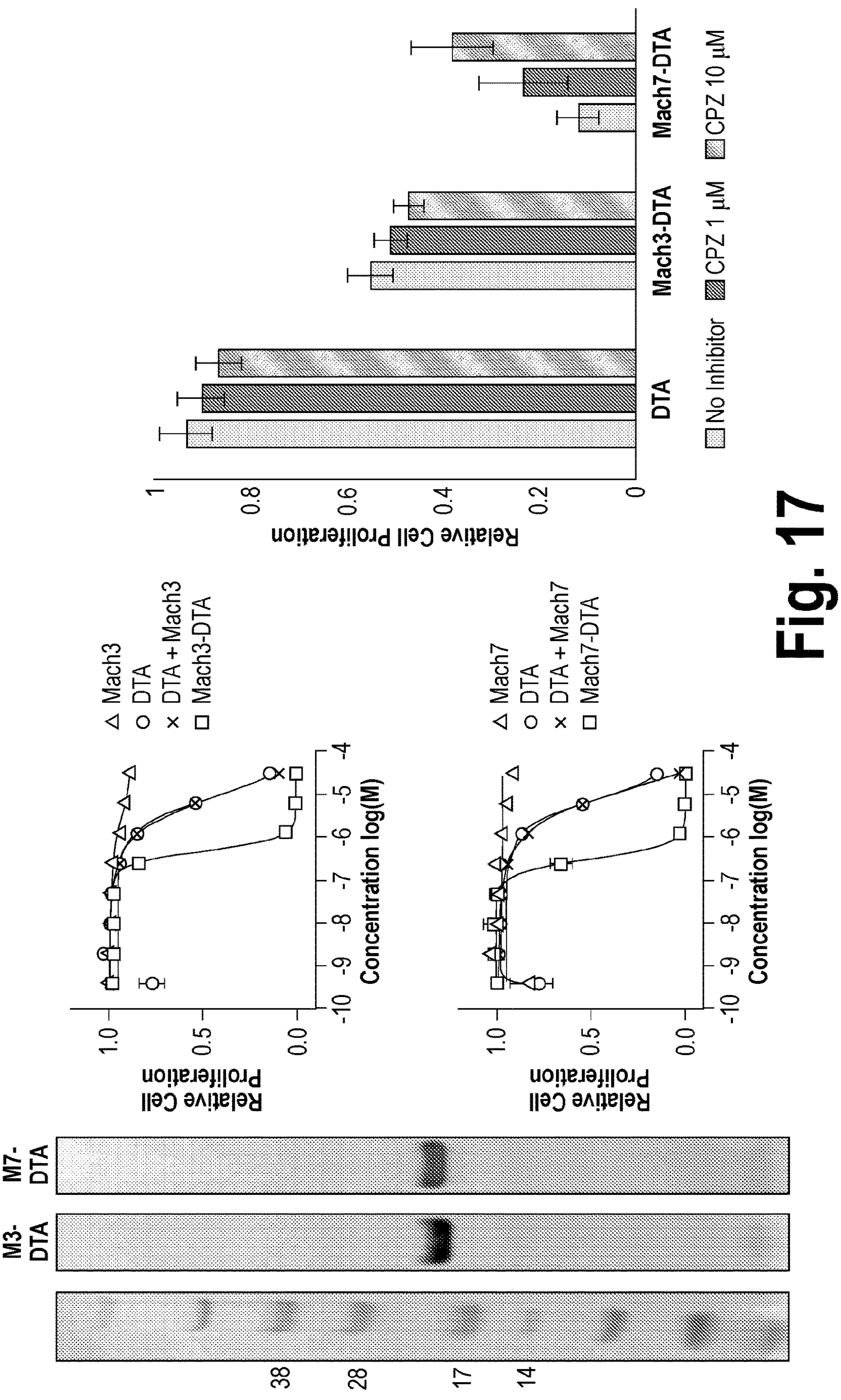

FIG. 17 shows coomassie stained SDS page gel of ligation of Mach-LPSTGG peptides to $G_5$-DTA.

Figure 18:
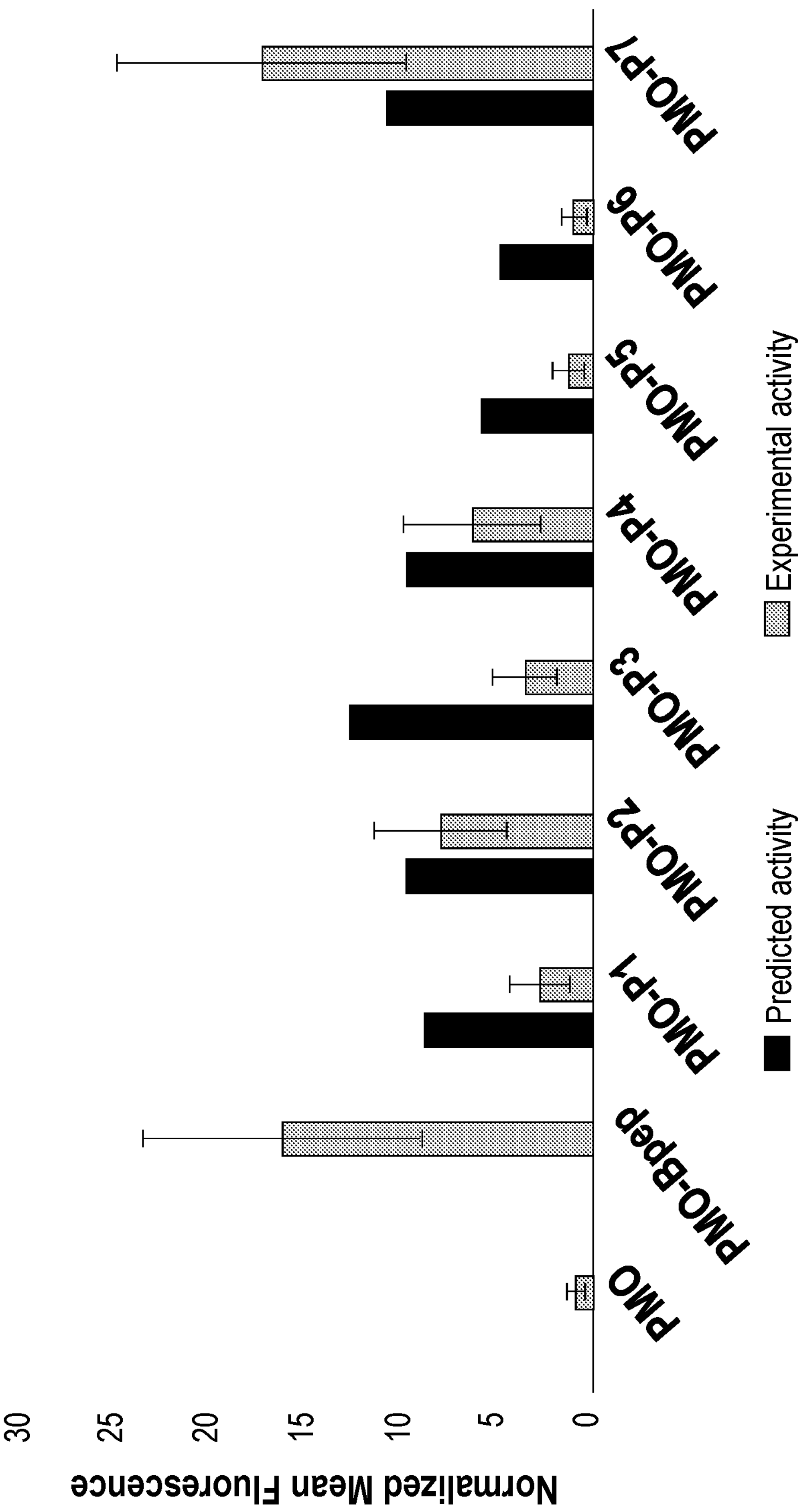

FIG. 18 shows activity (eGFP assay) of the PMO-peptide conjugates measured in three different biological replicates at a concentration of 5 μM for each PMO-peptide conjugate. The eGFP fluorescence was normalized with respect to the cells treated with unconjugated PMO.

Figure 19:
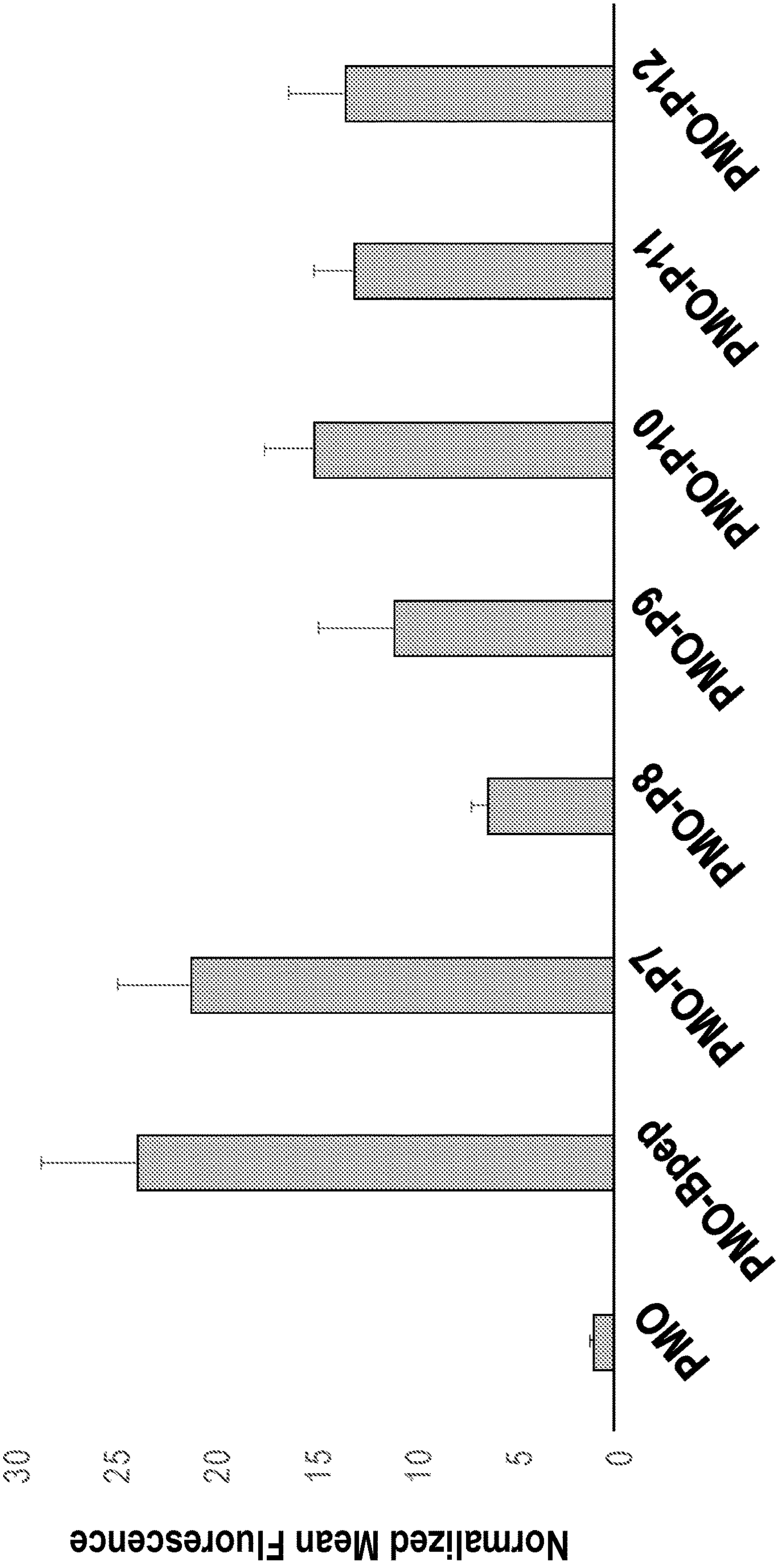

FIG. 19 shows superior activity of PMO-P7 with respect to its analogues (PMO-P8 to PMO-P12).

Figure 20:
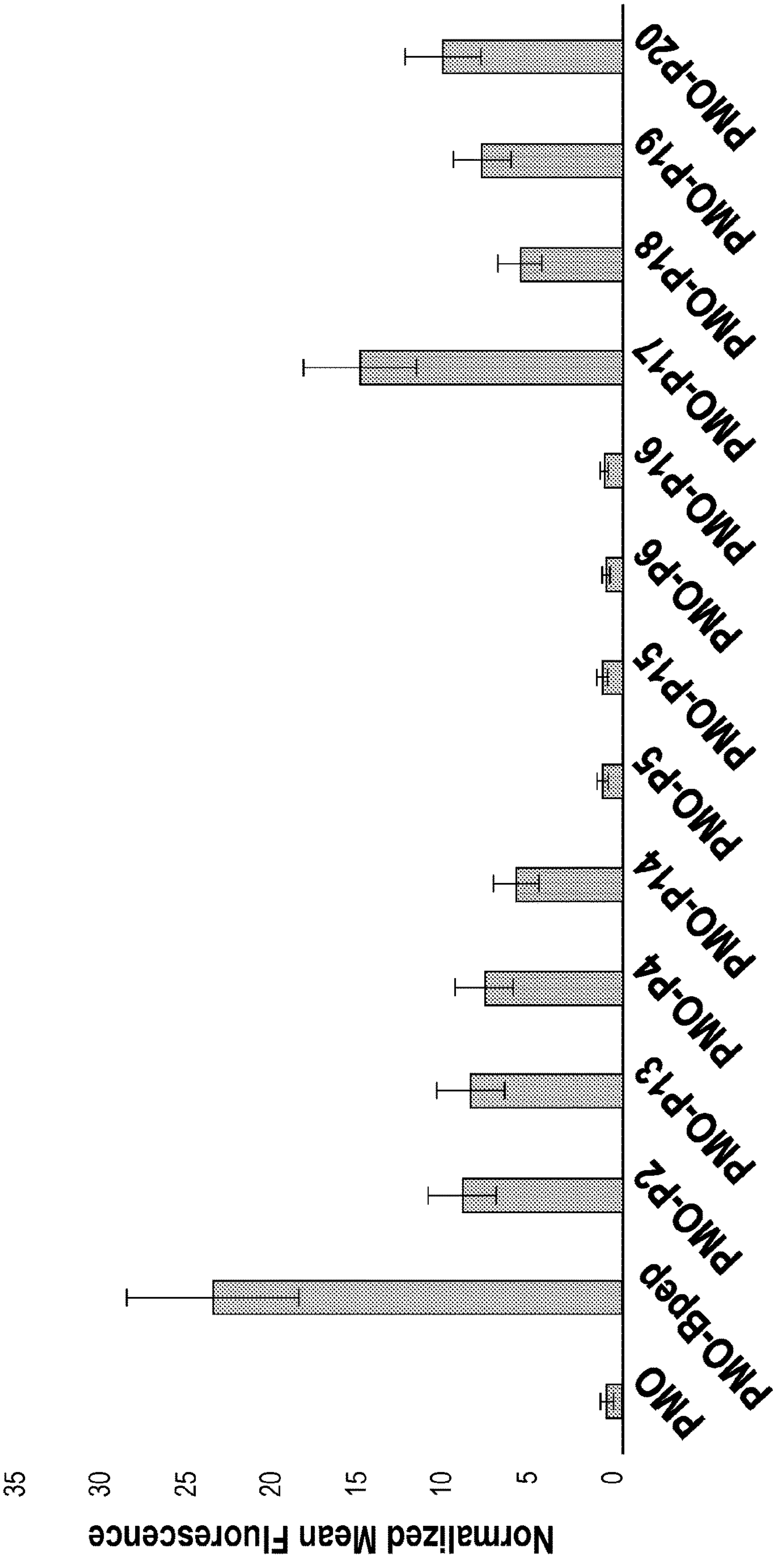

FIG. 20 shows the KXXC motif at the C-terminus of a peptide doesn't lead to an increase in PMO delivery with respect to the analog PMO-peptide conjugate in the absence of KXXC. Activity (eGFP assay) of pairs of PMO-peptide conjugates in the absence and in the presence of the KXXC motif at the C-terminus of the peptide.

Figure 21:
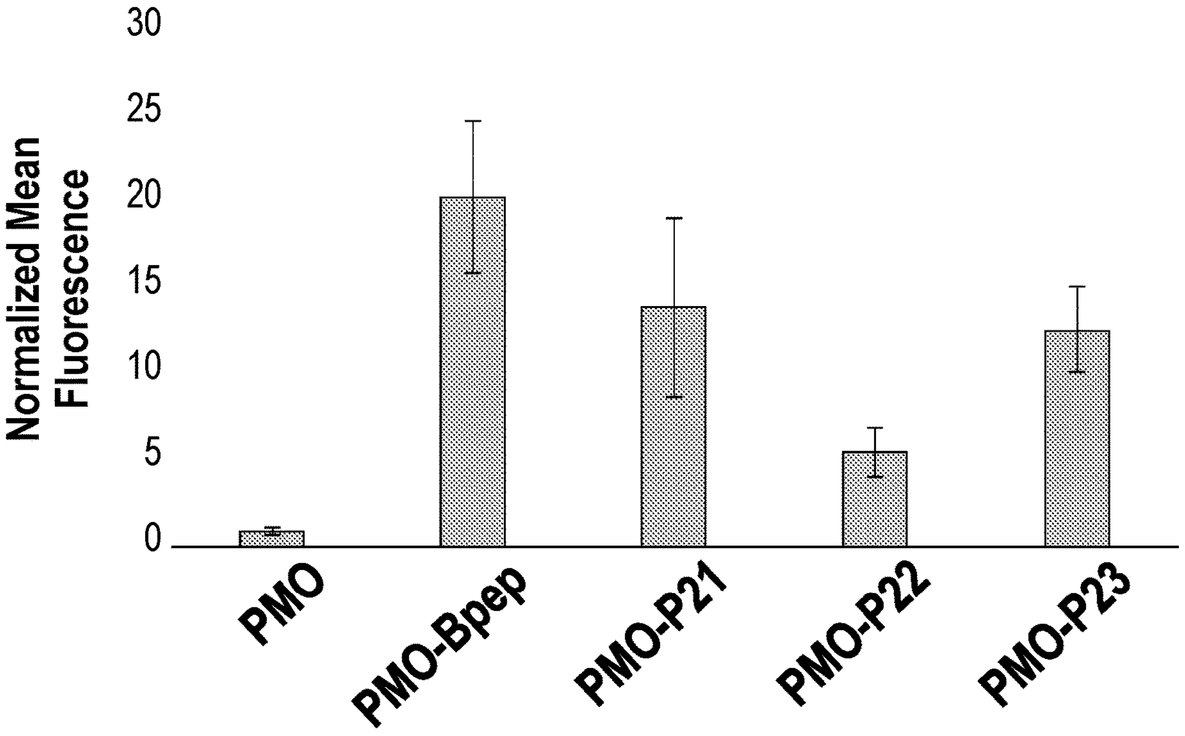

FIG. 21 shows activity of the PMO-P7 derivatives, PMO-P21, PMO-P22 and PMO-P23 at 5 μM.

Figure 22:
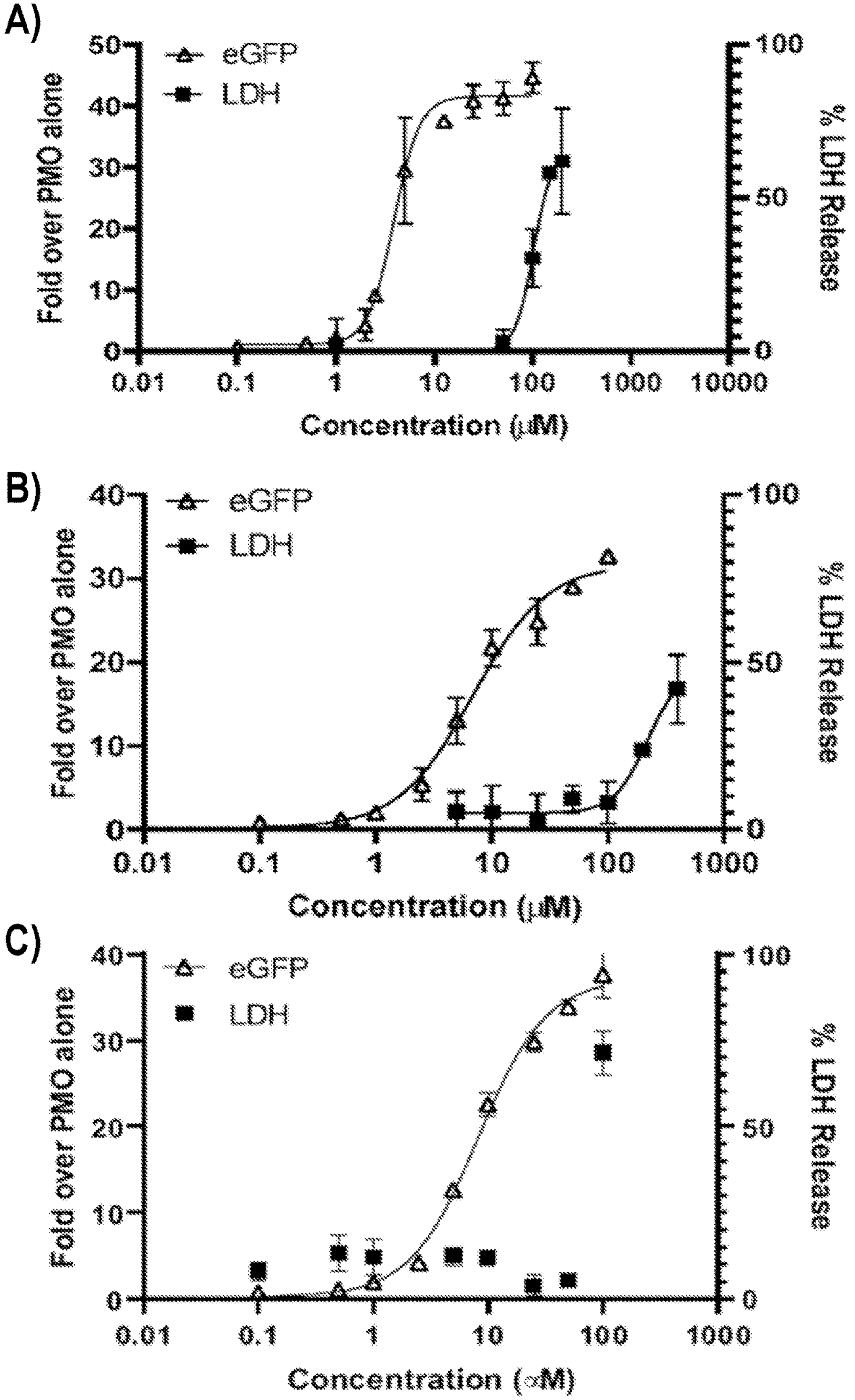

FIG. 22 A) shows representation of the dose-response curves (eGFP and LDH) for PMO-P7 (acetate salt). B) shows representation of the dose-response curves (eGFP and LDH) for PMO-P21 (acetate salt). C) shows representation of the dose-response curves (eGFP and LDH) for PMO-P23 (acetate salt).

Figure 23:
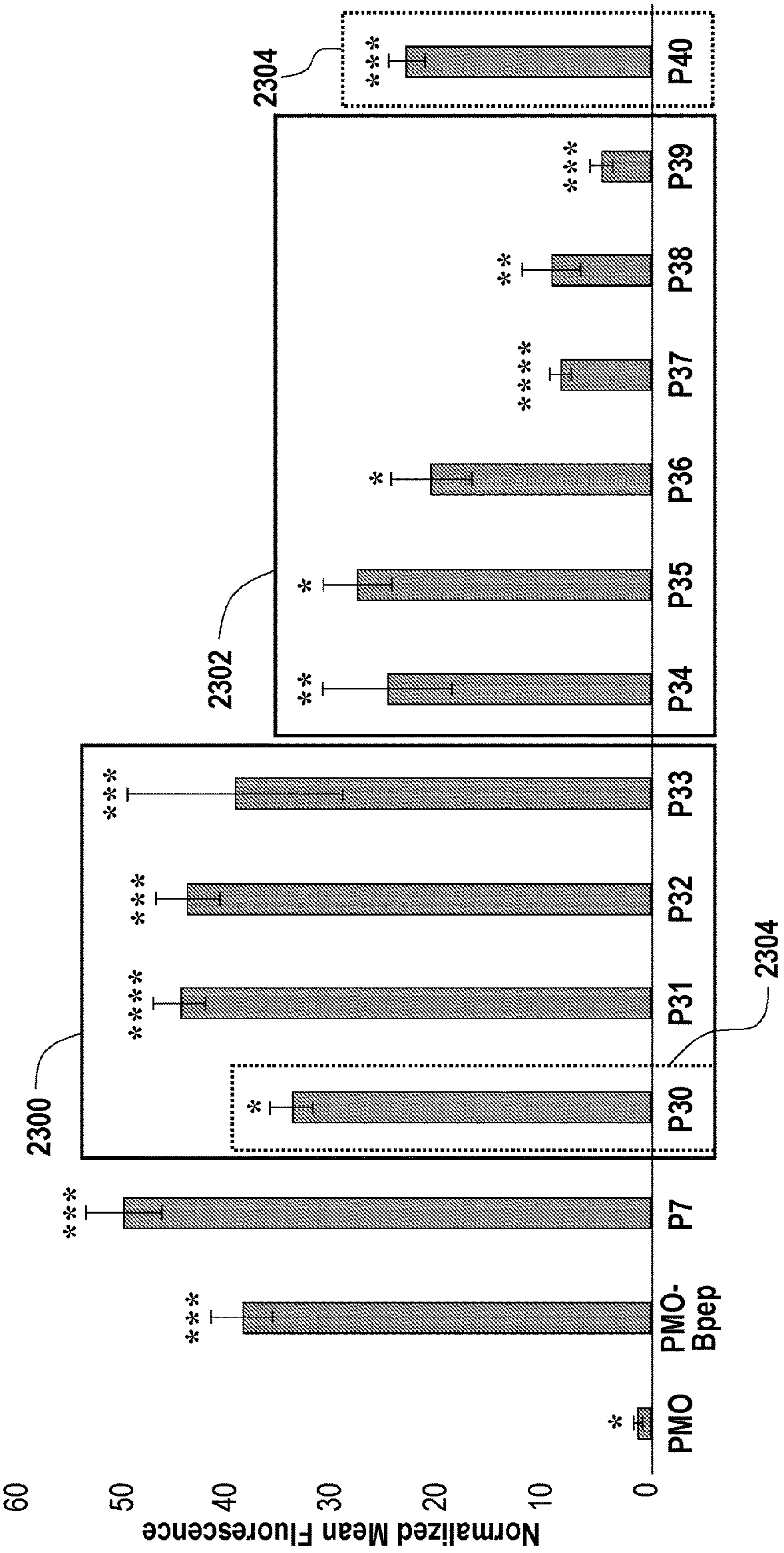

FIG. 23 shows that the polylysine backbone in peptide 6 is the primary cause for its improved activity in PMO delivery. Inside rectangle 2300 are the activities of the PMO-peptide conjugates containing Ala substitutions in the KXXC motif (PMO-8 to PMO-11). Inside rectangle 2302 are the activities of the PMO-peptides conjugates containing Ala substitutions in the polylysine backbone (PMO-12 to PMO-17). Inside dashed lines 2304 are the activities of the two PMO-peptide conjugates without the Cys residue at the C-terminus (PMO-8 and PMO-18). One asterisk (*) indicates p value smaller than 0.005 ($p<0.005$). Two asterisks () indicate p value smaller than 0.0005 ($p<0.0005$). Three asterisks (*) indicate p value smaller than 0.00005 ($p<0.00005$). Four asterisks (****) indicate p value smaller than 0.000005 ($p<0.000005$).

FIG. 24 shows that P7 doesn't show kidney toxicity while enhancing GFP protein levels in quadriceps, diaphragm and heart. A) shows no significant changes in BUN (blood urea nitrogen) levels after seven days, B) shows no significant changes in creatinine levels after seven days and C) shows no significant changes in cystatin C levels after seven days. D) shows levels of GFP protein in the Quadriceps (1300 pg of GFP/μg protein at 30 mg/kg and 4000 μg of GFP/μg protein at 60 mg/kg); saline N=6, 10 mg/kg N=6, 30 mg/kg N=7, 60 mg/kg N=4. E) shows levels of GFP protein in the Diaphragm (1100 pg of GFP/μg protein at 30 mg/kg and 2500 μg of GFP/μg protein at 60 mg/kg); saline N=6, 10 mg/kg N=6, 30 mg/kg N=6, 60 mg/kg N=4. F) shows levels of GFP protein in the Heart (2000 pg of GFP/μg protein at 30 mg/kg and 2200 μg of GFP/μg protein at 60 mg/kg); saline N=6, 10 mg/kg N=7, 30 mg/kg N=8, 60 mg/kg N=4. (N makes reference to the number of mice used).

Figure 25:
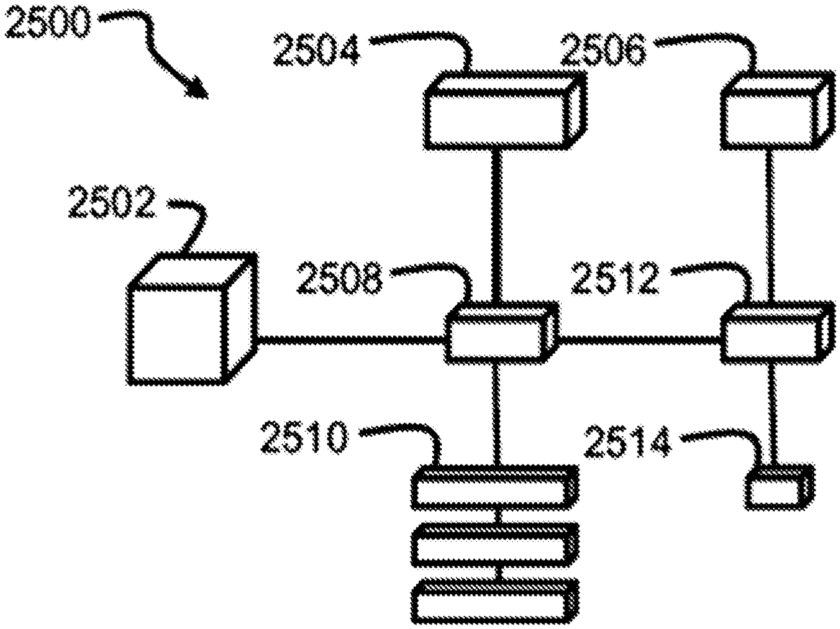

FIG. 25 shows an example of a computing device that can be used to implement the techniques described herein.

Figure 26:
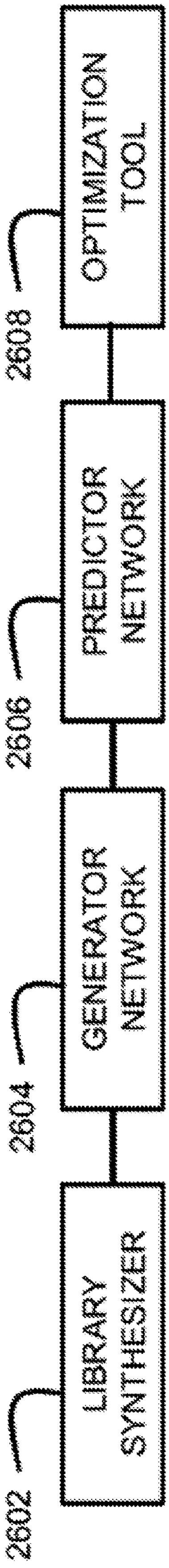

FIG. 26 shows a block diagram of a library synthesizer-generator-predictor-identifier modularized system as used according to the methods described herein for identifying one or more cell-penetrating peptides having optimal activity using machine learning.

Figure 27A:
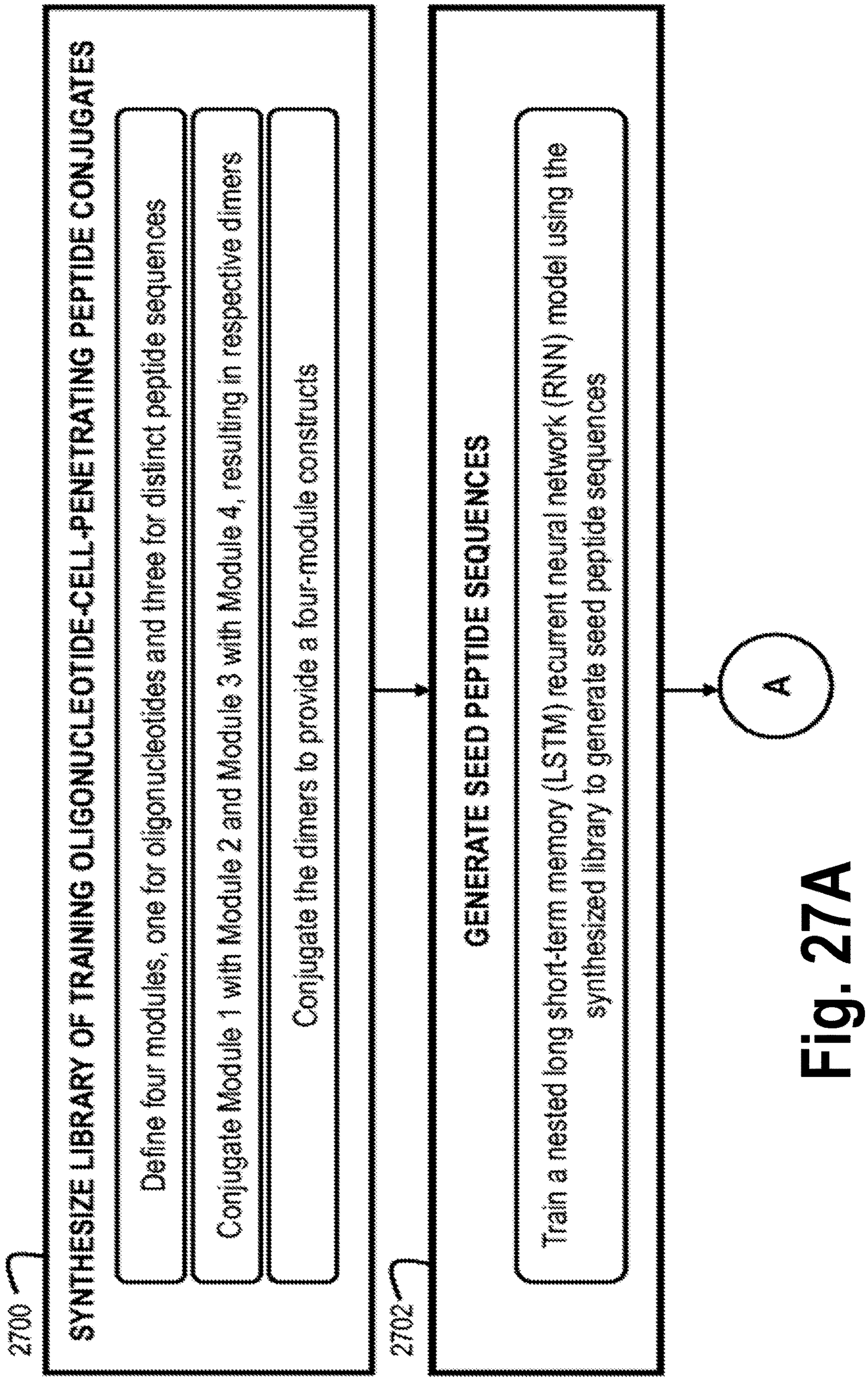
Figure 27B:
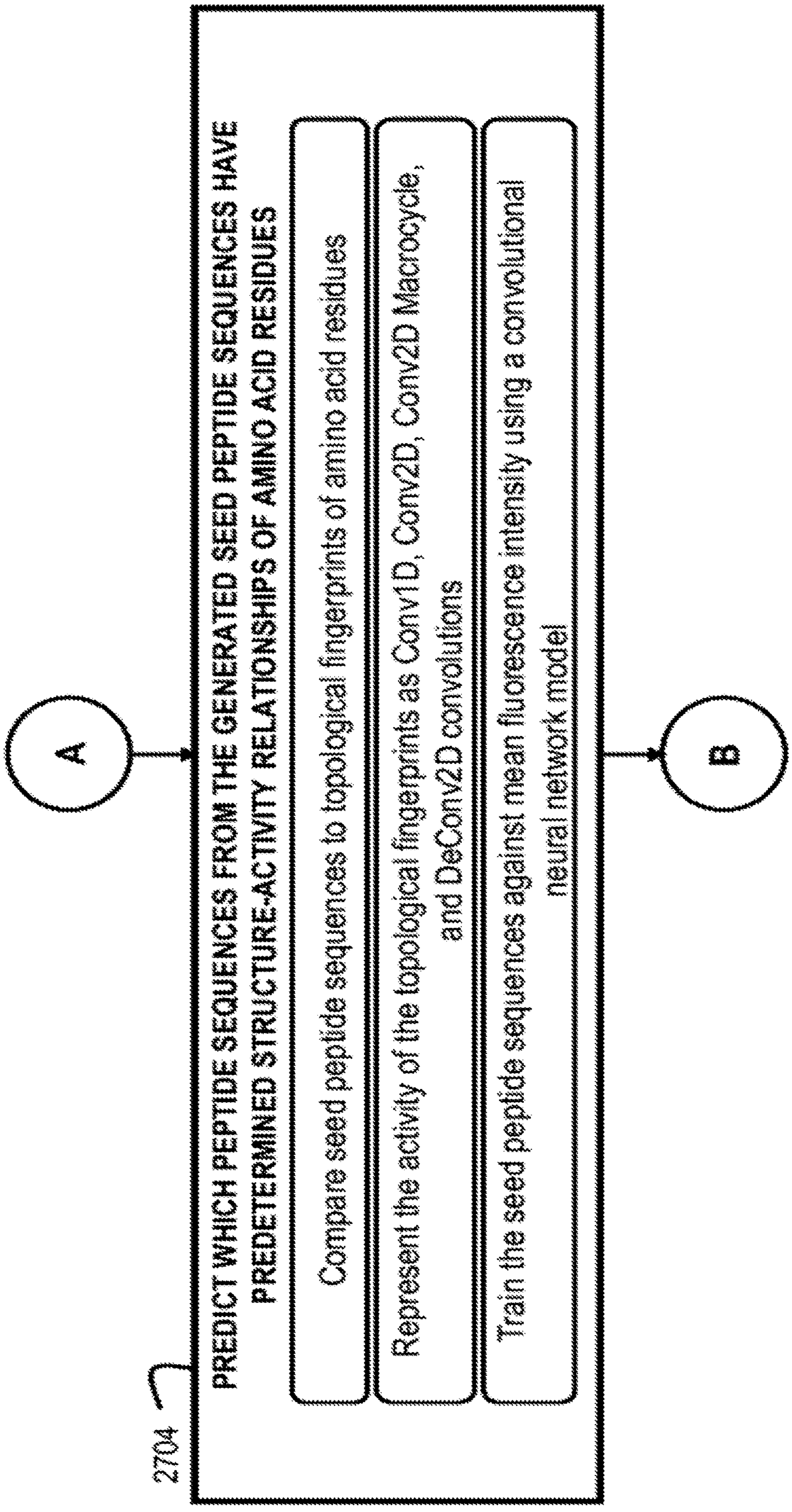
Figure 27C:
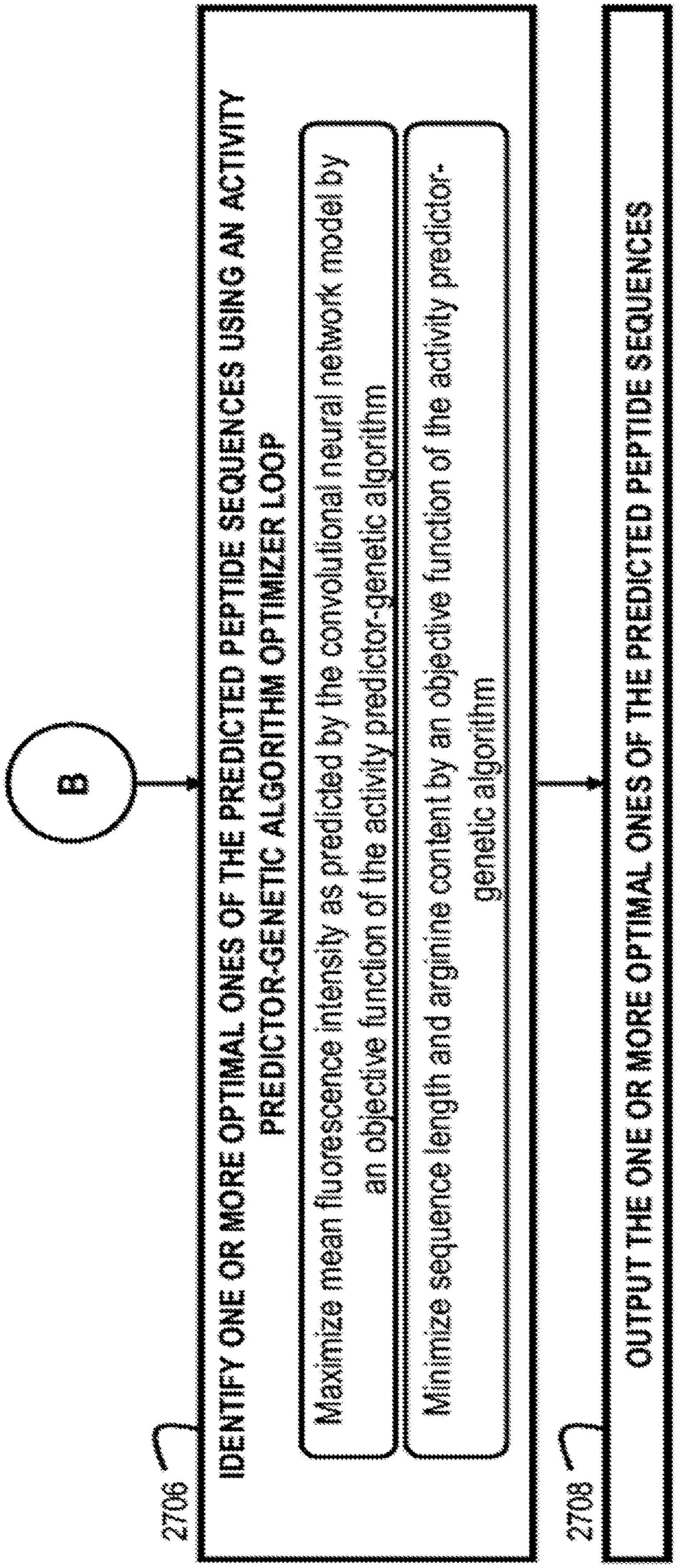

FIGS. 27A, 27B and 27C are collectively a flow chart showing a method of use of the library synthesizer-generator-predictor-identifier module of FIG. 26.

DETAILED DESCRIPTION

Phosphorodiamidate morpholino oligonucleotides (PMOs) are attractive therapeutic molecules for genetic diseases. PMOs are designed to recognize targets by Watson-Crick base pairing and exhibit a high level of specificity for their complimentary nucleotide sequence. Depending on the type of sequence targeted, PMOs can mediate a variety of effects, including blocking protein translation or modifying gene splicing. Eteplirsen, a PMO approved by the FDA to treat Duchenne muscular dystrophy, causes a mutation-containing exon in the pre-mRNA encoding for dystrophin to be excluded from the final protein transcript, restoring protein functionality.

In terms of structure, PMOs are neutral oligonucleotide analogs in which the ribosyl ring has been replaced with a morpholino ring and the negatively-charged phosphodiester backbone has been replaced with the uncharged phosphorodiamidate. The altered backbone structure prevents degradation in both serum and by intracellular nucleases.

However, the relatively large size and neutral charge of PMOs can lead to inefficient delivery to the cytosol and nucleus.

Cell-penetrating peptides (CPPs) are a promising strategy to improve the delivery of PMO to the nucleus. CPPs are relatively short sequences of 5-40 amino acids that ideally access the cytosol and can promote the intracellular delivery of cargo. CPPs can be classified into different groups based on their physicochemical properties. One common CPP class consists of repetitive, arginine-based peptides such as $R_{12}$ and Bpep (RXRRβRRXRRβR (SEQ ID NO: 10), in which X is aminohexanoic acid and β is β-alanine). These oligoarginine peptides are often random coils. When conjugated to PMO, the oligoarginine peptides have been some of the most effective peptides in promoting PMO delivery. Other CPPs, such as Penetratin, pVEC, and melittin, are more amphipathic in nature. While these sequences do contain cationic residues, the defined separation of charged and hydrophobic residues can promote amphipathic helix formation. However, amphipathic CPPs have not been demonstrated to significantly improve PMO efficacy.

No universal mechanism of cell entry exists for CPPs or CPP-PMO conjugates. The mechanism is often highly dependent on the treatment concentrations and the type of cargo attached. Above a certain threshold concentration (generally low micromolar), energy-independent cytosolic uptake can be observed faster than the time scale of endocytosis and cell surface recycling. The fast uptake rate provides evidence for a direct translocation mechanism similar to what is observed for a small molecule. However, at low, physiologically-relevant concentrations, uptake is primarily endocytic. Even within the category of endocytosis, CPPs and CPP-PMO conjugates can enter cells using one or multiple endocytic mechanisms. These endocytic mechanisms include micropinocytosis, clathrin-mediated endocytosis, caveolae-mediated endocytosis and clathrin/caveloae-independent endocytosis. CPP-PMO conjugates are primarily endocytosed at low concentrations, and the CPPs that are poor for PMO delivery are likely trapped in endosomes or excluded from the nuclear compartment.

Provided herein are peptide-PMO conjugates for improving PMO delivery. An increase in cellular uptake of the oligonucleotide, especially when compared to unconjugated PMOs and single CPP-PMO conjugates, is described herein. Also provided herein is a method for identifying one or more cell-penetrating peptides having optimal activity using machine learning.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, 1%, and ±0.1% from the specified value, as such variations are appropriate to perform the disclosed methods.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $-O-CH_2-CH_2-CH_3$, $-CH_2-CH_2-CH_2-OH$, $-CH_2-CH_2-NH-CH_3$, $-CH_2-S-CH_2-CH_3$, and $-CH_2-CH_2-S(=O)-CH_3$. Up to two heteroatoms may be consecutive, such as, for example, $-CH_2-NH-OCH_3$, or $-CH_2-CH_2-S-S-CH_3$.

The term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. In various embodiments, examples of an aryl group may include phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_{6-12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_{1-15}$-heteroaryl indicates the number of carbon atoms contained in the heteroaryl group without including the number of heteroatoms. For example, a $C_{1-9}$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the acronym DBCO refers to 8,9-dihydro-3H-dibenzo[b,f][1,2,3]triazolo[4,5-d]azocine.

The term "protecting group" or "chemical protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, monomethoxytrityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while coexisting amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "nucleobase," "base pairing moiety," "nucleobase-pairing moiety," or "base" refers to the heterocyclic ring portion of a nucleoside, nucleotide, and/or morpholino subunit.

Nucleobases may be naturally occurring, or may be modified or analogs of these naturally occurring nucleobases, e.g., one or more nitrogen atoms of the nucleobase may be independently at each occurrence replaced by carbon. Exemplary analogs include hypoxanthine (the base component of the nucleoside inosine); 2, 6-diaminopurine; 5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glenresearch.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

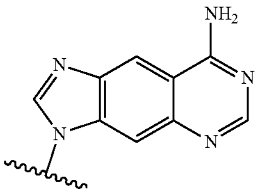

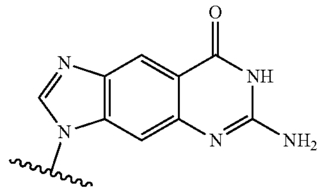

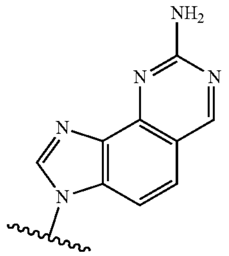

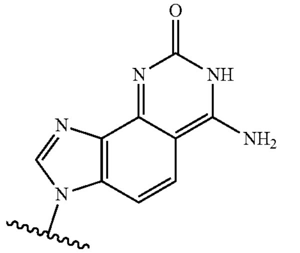

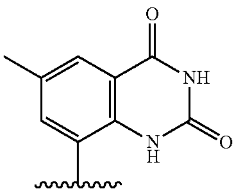

-continued

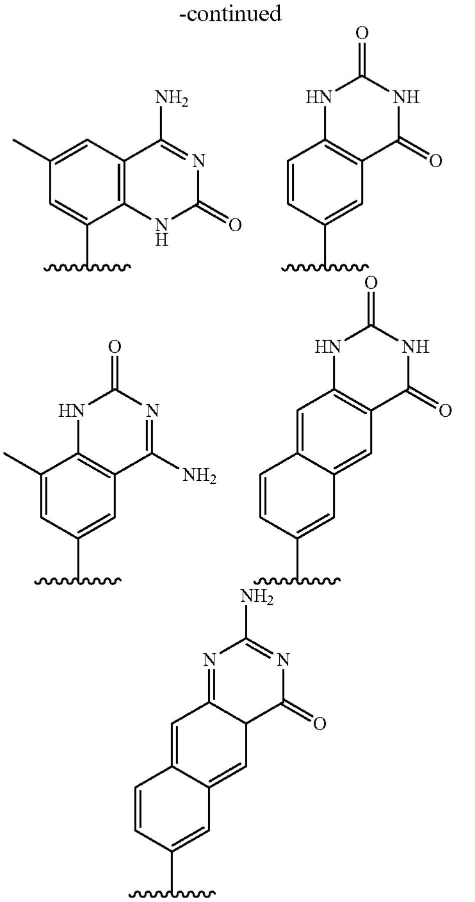

The terms "oligonucleotide" or "oligomer" refer to a compound comprising a plurality of linked nucleosides, nucleotides, or a combination of both nucleosides and nucleotides. In specific embodiments provided herein, an oligonucleotide is a morpholino oligonucleotide.

The phrase "morpholino oligonucleotide" or "PMO" refers to a modified oligonucleotide having morpholino subunits linked together by phosphoramidate or phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The terms "antisense oligomer," "antisense compound" and "antisense oligonucleotide" are used interchangeably and refer to a sequence of subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The oligomer may have exact (perfect) or near (sufficient) sequence complementarity to the target sequence; variations in sequence near the termini of an oligomer are generally preferable to variations in the interior.

Such an antisense oligomer can be designed to block or inhibit translation of mRNA or to inhibit/alter natural or abnormal pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. In various embodiments, a target sequence may be any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The antisense oligonucleotide and the target RNA are complementary to each other when a sufficient number of corresponding positions in each molecule are occupied by nucleotides which can hydrogen bond with each other, such that stable and specific binding occurs between the oligonucleotide and the target. Thus, "specifically hybridizable" and "complementary" are terms which are used to indicate a sufficient degree of complementarity or precise pairing such that stable and specific binding occurs between the oligonucleotide and the target. It is understood in the art that the sequence of an oligonucleotide need not be 100% complementary to that of its target sequence to be specifically hybridizable. An oligonucleotide is specifically hybridizable when binding of the oligonucleotide to the target molecule interferes with the normal function of the target RNA, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases. In some embodiments, the nucleobase is covalently linked at the N9 atom of the purine base, or at the N1 atom of the pyrimidine base, to the morpholine ring of a nucleotide or nucleoside.

Purine bases comprise a pyrimidine ring fused to an imidazole ring, as described by the general formula:

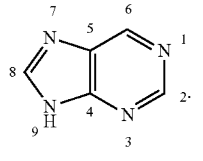

Purine

Adenine and guanine are the two purine nucleobases most commonly found in nucleic acids. These may be substituted with other naturally-occurring purines, including but not limited to N6-methyladenine, N2-methylguanine, hypoxanthine, and 7-methylguanine.

Pyrimidine bases comprise a six-membered pyrimidine ring as described by the general formula:

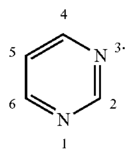

Pyrimidine

Cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), pseudouracil or derivatives thereof; and degenerate or universal bases, like 2,6-difluorotoluene or absent bases like abasic sites (e.g. 1-deoxyribose, 1,2-dideoxyribose, I-deoxy-2-O-methylribose; or pyrrolidine derivatives in which the ring oxygen has been replaced with nitrogen (azaribose)). Pseudouracil is a naturally occurring isomerized version of uracil, with a C-glycoside rather than the regular N-glycoside as in uridine.

Certain modified or substituted nucleobases are particularly useful for increasing the binding affinity of the antisense oligonucleotides of the disclosure. These include 5-substituted pyrimidines, 6-azapyrimidines and N-2, N-6 and 0-6 substituted purines, including 2-aminopropyladenine, 5-propynyluracil and 5-propynylcytosine. In various embodiments, nucleobases may include 5-methylcytosine substitutions, which have been shown to increase nucleic acid duplex stability by 0.6-1.2° C.

In some embodiments, modified or substituted nucleobases are useful for facilitating purification of antisense oligonucleotides. For example, in certain embodiments, antisense oligonucleotides may contain three or more (e.g., 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with hypoxanthine. The substitution of hypoxanthine for one or more guanines in a string of three or more consecutive guanine bases can reduce aggregation of the antisense oligonucleotide, thereby facilitating purification.

The oligonucleotides provided herein are synthesized and do not include antisense compositions of biological origin. The molecules of the disclosure may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution, or absorption, or a combination thereof.

The terms "complementary" and "complementarity" refer to oligonucleotides (i.e., a sequence of nucleotides) related by base-pairing rules. For example, the sequence "T-G-A (5-3')," is complementary to the sequence "T-C-A (5-3')." Complementarity may be "partial," in which only some of the nucleic acids' bases are matched according to base pairing rules. Or, there may be "complete," "total," or "perfect" (100%) complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100% complementarity. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5-terminus, 3'-terminus, or both termini.

The term "peptide" refers to a compound comprising a plurality of linked amino acids. The peptides provided herein can be considered to be cell penetrating peptides.

The terms "cell penetrating peptide" and "CPP" are used interchangeably and refer to cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. In various embodiments, a CPP embodiment of the disclosure may include an arginine-rich peptide as described further below.

As used herein, the term "chimeric peptide" refers to a polypeptide that comprises a first portion that is a first peptide or a fragment thereof, fused to a second portion that is a different peptide or fragment thereof. The chimeric peptide can comprise 2 or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond.

As used herein, the term "trimeric peptide" refers to a polypeptide that comprises a first portion that is a first peptide or a fragment thereof, fused to a second portion that is a different peptide or fragment thereof, fused to a third portion that is a different peptide or fragment thereof. The trimeric peptide can comprise 3 or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond.

As used herein, the term "MACH peptide" refers to a polypeptide that comprises cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. The MACH peptide can comprise 3 or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond. In a particular embodiment, the MACH peptide is comprised of peptides that have been optimized for cell delivery using a machine learning method. Examples of MACH peptides can be found in Table 4 provided herein.

As used herein, the term "amphipathic peptide" refers to a peptide with separated regions of essentially charged amino acids and essentially uncharged amino acids. These regions are known as the hydrophilic peptidyl segment and the hydrophobic peptidyl segment, respectively.

As used herein, the term "oligoarginine peptide" refers to a peptide where the peptide is comprised of all arginine or mostly arginine amino acid residues. In certain embodiments, the peptide is comprised entirely of arginine amino acid residues. In certain embodiments, the peptide is comprised of 50-99% arginine amino acid residues interspaced with amino acid linkers, such as, but not limited to, aminohexanoic acid or beta-alanine. In certain embodiments, the peptide is comprised of 75% arginine amino acid residues interspaced with amino acid linkers, such as, but not limited to, aminohexanoic acid or beta-alanine.

As used herein, the term "nuclear targeting peptide" refers to a peptide where the peptide contains a nuclear localization sequence that allows for the protein to import into the cell nucleus by nuclear transport. In a certain embodiment, this sequence consists of one or more positively charged amino acids exposed on the protein surface.

As used herein, the term "endosomal disrupting peptide" refers to a peptide where the peptide may help release of agents into the cytoplasm of cells. In a certain embodiment, this sequence consists of one or more positively charged amino acids.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

As used herein, "pharmaceutically acceptable salts" refers to derivatives of the disclosed oligonucleotides wherein the parent oligonucleotide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Peptide-Oligonucleotide-Conjugates

Provided herein are oligonucleotides chemically linked to a cell-penetrating peptide. The cell-penetrating peptide enhances activity, cellular distribution, or cellular uptake of the oligonucleotide.

In an embodiment, the cell-penetrating peptide is comprised of a MACH peptide.

In an embodiment, the cell-penetrating peptide is a MACH peptide which has been optimized using a machine learning method.

The oligonucleotides can additionally be chemically-linked to one or more heteroalkyl moieties (e.g., polyethylene glycol) that further enhance the activity, cellular distribution, or cellular uptake of the oligonucleotide. In one exemplary embodiment, the cell-penetrating peptide is covalently coupled at its N-terminal or C-terminal residue to either end, or both ends, of the oligonucleotide.

Thus, in one aspect, provided herein is a peptide-oligonucleotide conjugate of Formula I:

(I)

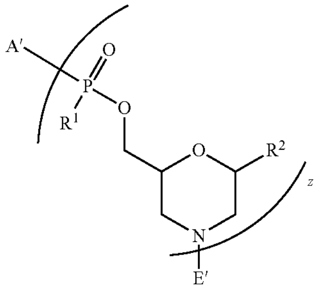

or a pharmaceutically acceptable salt thereof, wherein:

A' is selected from —N(H)$CH_2C(O)NH_2$, —N($C_{1-6}$-alkyl)$CH_2C(O)NH_2$,

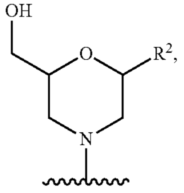

and

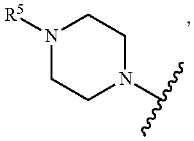

, and wherein $R^5$ is —C(O)(O-alkyl)$_x$-OH, wherein x is 3-10 and each alkyl group is, independently at each occurrence, $C_{2-6}$-alkyl, or $R^5$ is selected from —$C(O)C_{1-6}$-alkyl, trityl, monomethoxytrityl, —($C_{1-6}$-alkyl)-$R^6$, —($C_{1-6}$-heteroalkyl)-$R^6$, aryl-$R^6$, heteroaryl-$R^6$, —C(O)O—($C_{1-6}$-alkyl)-$R^6$, —C(O)O-aryl-$R^6$, —C(O)O— heteroaryl-$R^6$, and

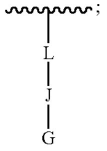

wherein $R^6$ is selected from OH, SH, and $NH_2$, or $R^6$ is O, S, or NH, each of which are covalently-linked to a solid support;

each $R^1$ is independently selected from OH and —$N(R^3)(R^4)$, wherein each $R^3$ and $R^4$ are, independently at each occurrence, —$C_{1-6}$-alkyl;

each $R^2$ is independently, at each occurrence, selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, —$C_{1-6}$-alkyl, —$C(O)C_{1-6}$-alkyl, benzoyl, stearoyl, trityl, monomethoxytrityl, dimethoxytrityl, trimethoxytrityl,

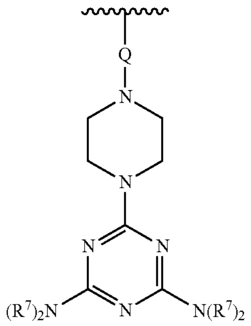

and

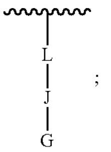

wherein

Q is —$C(O)(CH_2)_6C(O)$— or —$C(O)(CH_2)_2S_2(CH_2)_2C(O)$—;

$R^7$ is —$(CH_2)_2OC(O)N(R^8)_2$, wherein $R^3$ is —$(CH_2)_6NHC(=NH)NH_2$;

L is —$C(O)(OH_2)_{1-6}$—$C_{7-15}$-heteroaromatic-$(CH_2)_{1-6}C(O)$—, wherein L is covalently-linked by an amide bond to J;

J is a carrier peptide;

G is selected from H, —$C(O)C_{1-6}$-alkyl, benzoyl, and stearoyl, wherein G is covalently-linked to J;

wherein at least one of the following conditions is true:

1) A' is

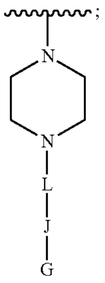

or 2) E' is

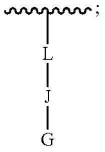

and wherein the carrier peptide J is selected from the following sequences:

| | |
|---|---|
| MACH 1 (SEQ ID NO: 57) | ALKBRSAAKAVRWPKKKIKQASKKVAKYALXXXRKKKAASKXWLQLHW PRW |
| MACH 2 (SEQ ID NO: 58) | PPLRNAKKKNLKNNLKMDPKFTKKVKQGALKLNRRKKNRGPKGPXKH WTT |
| MACH 3 (SEQ ID NO: 59) | QKKRKSKANKKNWPKGKLSIHAKDYKQGPKAKXRKQRXR |
| MACH 4 (SEQ ID NO: 59) | KKGKKQNKKKHRWPKKKVPQPKKMFKQGABXRX |
| MACH 5 (SEQ ID NO: 61) | AKKKIAKAKKHRGPNBGIHAPVSKIKDPLKXXX |
| MACH 6 (SEQ ID NO: 62) | ALKBRSAAKAVRWPKKAIKQASKKVAKYALKXXRKKKAASKXWLQLHW PRW |

-continued

| | |
|---|---|
| MACH 7<br>(SEQ ID<br>NO: 63) | XKHPXAVQBAARAWKVPAAALWKKKRLKKSSKQKKKWLWKARSAXK<br>YXRLI |
| MACH 8<br>(SEQ ID<br>NO: 64) | BKGKNLLAKIRRGPNGGNBQGSQGYLLYLLXRXRRQRXXYPWWRXKH<br>XRWXXRXRGHXRRRRQXLKPDRXRGGKGSVS |
| MACH 9<br>(SEQ ID<br>NO: 65) | KKKKNLNBKSRRGPNGGALQPSQGYLQPLNXRXRRQRXXYPWWRXK<br>HXRWRXRYHXRRRRQXLKPG |
| MACH 11<br>(SEQ ID<br>NO: 66) | TSNLKLHLAPPVKKKALKKPLYKAKKKKKVVSPTWXTDQEW |
| MACH 12<br>(SEQ ID<br>NO: 67) | KGGKNLAKKIRRGPNGGALQPSQGYLLYLBXRXRRQRXXGPXWRXKH<br>XRWXXXXXRPTHXRRRRQXL**C**PGRXRP**C**RGSVS |
| MACH 13<br>(SEQ ID<br>NO: 68) | AKKKKLGBKALRWPNGK**C**PQPKEK**C**PKYLLGRXRRKRXRYPWWRXK<br>HRRW |
| P1<br>(MACH 14)<br>(SEQ ID<br>NO: 69) | KXKKQQGKKKHR |
| P2<br>(MACH 15)<br>(SEQ ID<br>NO: 70) | KKKKKQBKKKHRWPMG |
| P3<br>(MACH 16)<br>(SEQ ID<br>NO: 71) | KKKKNQBKKKHRWPMKXCPQ |
| P4<br>(MACH 17)<br>(SEQ ID<br>NO: 72) | HKKKKQBKKKHRWP |
| P5<br>(MACH 18)<br>(SEQ ID<br>NO: 73) | KXKHQQQXK |
| P6<br>(MACH 19)<br>(SEQ ID<br>NO: 74) | KXKXT |
| P7<br>(MACH 20)<br>(SEQ ID<br>NO: 75) | KKKKKQBKKKHRWPKXXC |
| P8<br>(SEQ ID<br>NO: 76) | KKKKKCBKKKHRWPKXXQ |
| P9<br>(SEQ ID<br>NO: 77) | KKKXKQBKKKHRWPKKXC |
| P10<br>(SEQ ID<br>NO: 78) | KCHKXKWKKPKRXKQKBK |
| P11<br>(SEQ ID<br>NO: 79) | KKKKKQCKKKHRWPKXXC |
| P12<br>(SEQ ID<br>NO: 80) | KKKKKQBKKKHRWPKXXG |

-continued

| | |
|---|---|
| P13 (SEQ ID NO: 81) | KKKKKQBKKKHRWPMGKXXC |
| P14 (SEQ ID NO: 82) | HKKKKQBKKKHRWPKXXC |
| P15 (SEQ ID NO: 83) | KXKHQQQXKKXXC |
| P16 (SEQ ID NO: 84) | KXKXTKXXC |
| P17 (SEQ ID NO: 26) | ALWKTLLKKVLKAPKKKRKV |
| P18 (SEQ ID NO: 85) | ALWKTLLKKVLKAPKKKRKVKXXC |
| P19 (SEQ ID NO: 45) | RQIKIWFQNRRMKWKK |
| P20 (SEQ ID NO: 86) | RQIKIWFQNRRMKWKKKXXC |
| P21 (SEQ ID NO: 87) | KKKKKQBKKKHRWP |
| P22 (SEQ ID NO: 88) | KKKKKQBKKKHRWPKXXCCC |
| P23 (SEQ ID NO: 89) | KKKKKQBKKKHRWAKXXC |

wherein X is 6-amino hexanoic acid, B is R-alanine, and C is covalently bound to another C by $L^1$;

wherein $L^1$ is

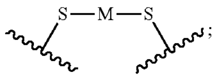;

M is

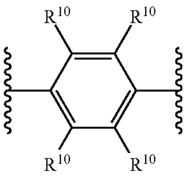,

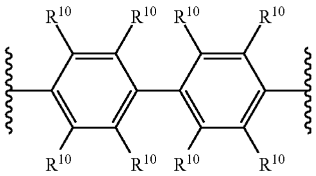, or

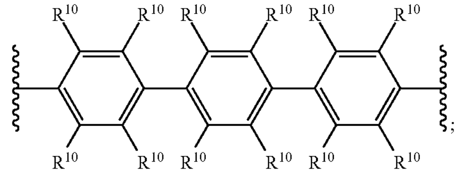;

and $R^{10}$ is independently at each occurrence H or a halogen.

In one embodiment, z is 8-30. In another embodiment, z is 10-30. In a further embodiment, z is 15-25. In another embodiment, z is 20-25. In an embodiment, z is 8, 9, 10, 11, 12, 13, 14, 15, 16, 17, 18, 19, 20, 21, 22, 23, 24, 25, 26, 27, 28, 29, or 30.

In yet another embodiment, E' is selected from H, —$C_{1-6}$-alkyl, —C(O)$C_{1-6}$-alkyl, benzoyl, stearoyl, trityl, monomethoxytrityl, dimethoxytrityl, trimethoxytrityl, and

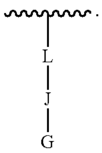

In another embodiment, A' is selected from —N($C_{1-6}$-alkyl)$CH_2C(O)NH_2$,

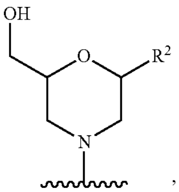

,

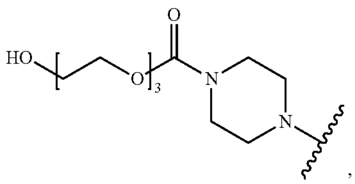

, and

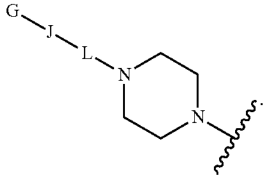

In still another embodiment, E' is selected from H, —$C(O)CH_3$, benzoyl, stearoyl, trityl, 4-methoxytrityl, and

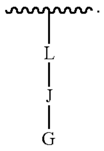

In yet another embodiment, A' is selected from —$N(C_{1-6}\text{-alkyl})CH_2C(O)NH_2$,

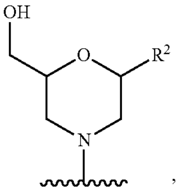

, and

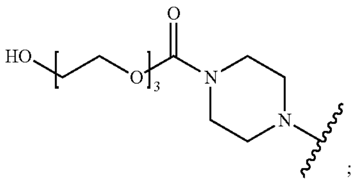

;

and

E' is

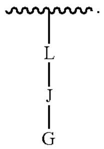

In another embodiment, A' is

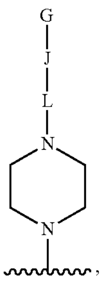

, and

E' is selected from H, —$C(O)CH_3$, trityl, 4-methoxytrityl, benzoyl, and stearoyl.

In an embodiment, the peptide-oligonucleotide conjugate of Formula I is a peptide-oligonucleotide conjugate of Formula Ia:

(Ia)

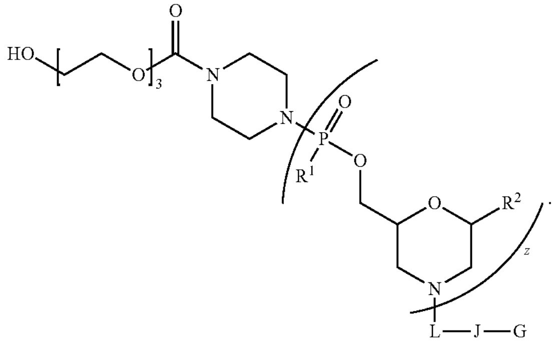

In an embodiment, the peptide-oligonucleotide conjugate of Formula I is a peptide-oligonucleotide conjugate of Formula Ib:

(Ib)

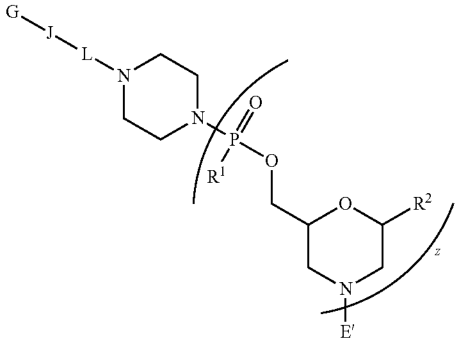

wherein E' is selected from H, $C_{1-6}$-alkyl, —$C(O)CH_3$, benzoyl, and stearoyl.

In an embodiment of Formula I, Ia, and Ib, each $R^1$ is $N(CH_3)_2$.

In yet another embodiment of Formula I, Ia, and Ib, each $R^2$ is a nucleobase, wherein the nucleobase independently at each occurrence comprises a $C_{4-6}$-heterocyclic ring selected from pyridine, pyrimidine, triazinane, purine, and deaza-purine.

In another embodiment of Formula I, Ia, and Ib, each $R^2$ is a nucleobase, wherein the nucleobase independently at each occurrence comprises a $C_{4-6}$-heterocyclic ring selected from pyrimidine, purine, and deaza-purine.

In still another embodiment of Formula I, Ia, and Ib, each $R^2$ is a nucleobase independently at each occurrence selected from adenine, 2,6-diaminopurine, 7-deaza-adenine, guanine, 7-deaza-guanine, hypoxanthine, cytosine, 5-methyl-cytosine, thymine, uracil, and hypoxanthine.

In yet another embodiment of Formula I, Ia, and Ib, each $R^2$ is a nucleobase independently at each occurrence selected from adenine, guanine, cytosine, 5-methyl-cytosine, thymine, uracil, and hypoxanthine.

In another embodiment of Formula I, Ia, and Ib, L is —$C(O)(CH_2)_{1-6}$-DBCO—$(CH_2)_{1-6}C(O)$—.

In another embodiment of Formula I, Ia, and Ib, L is

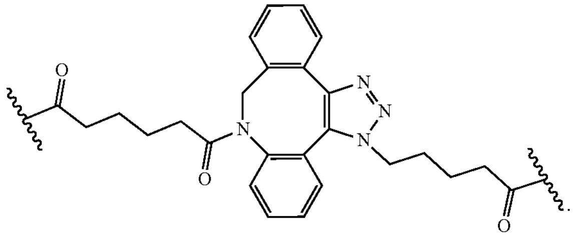 [SMILES: *C(=O)CCCCC(=O)N1Cc2ccccc2-c2nnn(CCCCC(*)=O)c2-c2ccccc21]

In another embodiment of Formula I, Ia, and Ib, M is

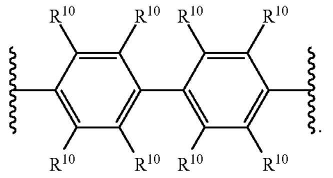

In yet another embodiment of Formula I, Ia, and Ib, M is

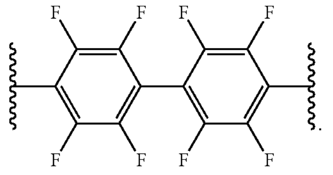 [SMILES: *c1c(F)c(F)c(-c2c(F)c(F)c(*)c(F)c2F)c(F)c1F]

In another embodiment of Formula I, Ia, and Ib, $L^1$ is covalently-linked to the side chain of a terminal cysteine on $P^1$ and $P^2$ to form the structure:

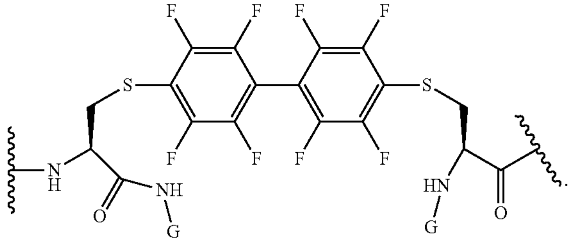

In another embodiment of Formula I, Ia, and Ib, G is selected from H, $C(O)CH_3$, benzoyl, and stearoyl.

In still another embodiment of Formula I, Ia, and Ib, G is H or $—C(O)CH_3$.

In yet another embodiment of Formula I, Ia, and Ib, G is H.

In yet another embodiment of Formula I, Ia, and Ib, G is $—C(O)CH_3$.

In yet another embodiment of Formula I, Ia, and Ib, the oligonucleotide-peptide conjugate demonstrates at least a 40-fold improvement in uptake as compared to unconjugated oligonucleotide.

In a further embodiment of Formula I, Ia, and Ib, the oligonucleotide-peptide conjugate demonstrates at least a 5-fold improvement in uptake as compared to unconjugated oligonucleotide.

In an embodiment, the oligonucleotide-peptide conjugate is non-toxic.

In another embodiment, the oligonucleotide-peptide conjugate is nonimmunogenic.

In another aspect, provided herein is a peptide-oligonucleotide conjugate of Formula II:

(II)

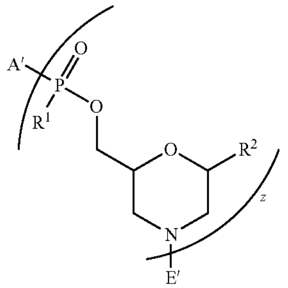

or a pharmaceutically acceptable salt thereof, wherein:

A' is selected from $—N(H)CH_2C(O)NH_2$, $—N(C_{1-6}\text{-alkyl})CH_2C(O)NH_2$,

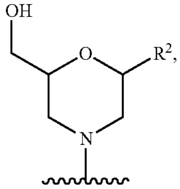 and 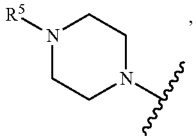, wherein $R^5$ is $—C(O)(O\text{-alkyl})_x\text{-OH}$, wherein x is 3-10 and each alkyl group is, independently at each occurrence, $C_{2-6}$-alkyl, or $R^5$ is selected from $—C(O)C_{1-6}$-alkyl, trityl, monomethoxytrityl, $—(C_{1-6}\text{-alkyl})\text{-}R^6$, $—(C_{1-6}\text{-heteroalkyl})\text{-}R^6$, aryl-$R^6$, heteroaryl-$R^6$, $—C(O)O—(C_{1-6}\text{-alkyl})\text{-}R^6$, $—C(O)O\text{-aryl-}R^6$, $—C(O)O—$ heteroaryl-$R^6$, and

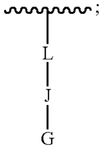;

wherein $R^6$ is selected from OH, SH, and $NH_2$, or $R^6$ is O, S, or NH, each of which are covalently-linked to a solid support;

each $R^1$ is independently selected from OH and $—N(R^3)(R^4)$, wherein each $R^3$ and $R^4$ are, independently at each occurrence, $—C_{1-6}$-alkyl;

each $R^2$ is independently, at each occurrence, selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, —$C_{1-6}$-alkyl, —$C(O)C_{1-6}$-alkyl, benzoyl, stearoyl, trityl, monomethoxytrityl, dimethoxytrityl, trimethoxytrityl,

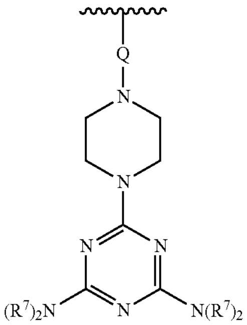

and

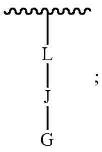

;

wherein

Q is —$C(O)(CH_2)_6C(O)$— or —$C(O)(CH_2)_2S_2(CH_2)_2C(O)$—;

$R^7$ is —$(CH_2)_2OC(O)N(R^8)_2$, wherein $R^8$ is —$(CH_2)_6NHC(=NH)NH_2$;

L is —$C(O)(CH_2)_{1-6}$—$C_{7-15}$-heteroaromatic-$(CH_2)_{1-6}C(O)$—, wherein L is covalently-linked by an amide bond to J;

J is a carrier peptide;

G is selected from H, —$C(O)C_{1-6}$-alkyl, benzoyl, and stearoyl, wherein G is covalently-linked to J;

wherein at least one of the following conditions is true:

1) A' is

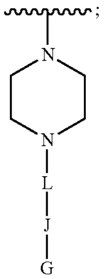

or 2) E' is

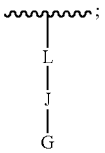

and wherein the carrier peptide J is selected from the following sequences:

| | |
|---|---|
| MACH 1 (SEQ ID NO: 57) | ALKBRSAAKAVRWPKKKIKQASKKVAKYALXXXRKKKAASKXWLQLHWPRW |
| MACH 2 (SEQ ID NO: 58) | PPLRNAKKKNLKNNLKMDPKFTKKVKQGALKLNRRKKNRGPKGPXKHWTT |
| MACH 3 (SEQ ID NO: 59) | QKKRKSKANKKNWPKGKLSIHAKDYKQGPKAKXRKQRXR |
| MACH 4 (SEQ ID NO: 60) | KKGKKQNKKKHRWPKKKVPQPKKMFKQGABXRX |
| MACH 5 (SEQ ID NO: 61) | AKKKIAKAKKHRGPNBGIHAPVSKIKDPLKXXX |
| MACH 6 (SEQ ID NO: 62) | ALKBRSAAKAVRWPKKAIKQASKKVAKYALKXXRKKKAASKXWLQLHWPRW |
| MACH 7 (SEQ ID NO: 63) | XKHPXAVQBAARAWKVPAAALWKKKRLKKSSKQKKKWLWKARSAXKYXRLI |
| MACH 8 (SEQ ID NO: 64) | BKGKNLLAKIRRGPNGGNBQGSQGYLLYLLXRXRRQRXXYPWWRXKHXRWXXRXRGHXRRRRQXLKPDRXRGGKGSVS |
| MACH 9 (SEQ ID NO: 65) | KKKKNLNBKSRRGPNGGALQPSQGYLQPLNXRXRRQRXXYPWWRXKHXRWRXRYHXRRRRQXLKPG |
| MACH 11 (SEQ ID NO: 66) | TSNLKLHLAPPVKKKALKKPLYKAKKKKKVVSPTWXTDQEW |
| MACH 12 (SEQ ID NO: 67) | KGGKNLAKKIRRGPNGGALQPSQGYLLYLBXRXRRQRXXGPXWRXKHXRWXXXXXRPTHXRRRRQXLCPGRXRPCRGSVS |

-continued

| | |
|---|---|
| MACH 13 (SEQ ID NO: 68) | AKKKKLGBKALRWPNGK**C**PQPKEK**C**PKYLLGRXRRKRXRYPWWRXK HRRW |
| P1 (MACH 14) (SEQ ID NO: 69) | KXKKQQGKKKHR |
| P2 (MACH 15) (SEQ ID NO: 70) | KKKKKQBKKKHRWPMG |
| P3 (MACH 16) (SEQ ID NO: 71) | KKKKNQBKKKHRWPMKXCPQ |
| P4 (MACH 17) (SEQ ID NO: 72) | HKKKKQBKKKHRWP |
| P5 (MACH 18) (SEQ ID NO: 73) | KXKHQQQXK |
| P6 (MACH 19) (SEQ ID NO: 74) | KXKXT |
| P7 (MACH 20) (SEQ ID NO: 75) | KKKKKQBKKKHRWPKXXC |
| P8 (SEQ ID NO: 76) | KKKKKCBKKKHRWPKXXQ |
| P9 (SEQ ID NO: 77) | KKKXKQBKKKHRWPKKXC |
| P10 (SEQ ID NO: 78) | KCHKXKWKKPKRXKQKBK |
| P11 (SEQ ID NO: 79) | KKKKKQCKKKHRWPKXXC |
| P12 (SEQ ID NO: 80) | KKKKKQBKKKHRWPKXXG |
| P13 (SEQ ID NO: 81) | KKKKKQBKKKHRWPMGKXXC |
| P14 (SEQ ID NO: 82) | HKKKKQBKKKHRWPKXXC |
| P15 (SEQ ID NO: 83) | KXKHQQQXKKXXC |
| P16 (SEQ ID NO: 84) | KXKXTKXXC |
| P17 (SEQ ID NO: 26) | ALWKTLLKKVLKAPKKKRKV |

-continued

| | |
|---|---|
| P18 (SEQ ID NO: 85) | ALWKTLLKKVLKAPKKKRKVKXXC |
| P19 (SEQ ID NO: 45) | RQIKIWFQNRRMKWKK |
| P20 (SEQ ID NO: 86) | RQIKIWFQNRRMKWKKKXXC |
| P21 (SEQ ID NO: 87) | KKKKKQBKKKHRWP |
| P22 (SEQ ID NO: 88) | KKKKKQBKKKHRWPKXXCCC |
| P23 (SEQ ID NO: 89) | KKKKKQBKKKHRWAKXXC |
| P24 (SEQ ID NO: 90) | KXKHQQGP |
| P25 (SEQ ID NO: 91) | KXKHQQGKKT |
| P26 (SEQ ID NO: 92) | HKKKQQGKKKHRW |
| P27 (SEQ ID NO: 93) | KKKKKQBKKKHRWPM |
| P28 (SEQ ID NO: 94) | KKKKKQGKKHRWPMGG |
| P29 (SEQ ID NO: 95) | KKKKNQBKKKHRWPMKXCP |
| P30 (SEQ ID NO: 96) | KKKKKQBKKKHRWPKXXA |
| P31 (SEQ ID NO: 97) | KKKKKQBKKKHRWPKXAC |
| P32 (SEQ ID NO: 98) | KKKKKQBKKKHRWPKAXC |
| P33 (SEQ ID NO: 99) | KKKKKQBKKKHRWPAXXC |
| P34 (SEQ ID NO: 100) | KAKKKQBKKKHRWPKXXC |
| P35 (SEQ ID NO: 101) | KKKKKQBKAKHRWPKXXC |
| P36 (SEQ ID NO: 102) | KKKAKQBKKKHRWPKXXC |

-continued

| | |
|---|---|
| P37 (SEQ ID NO: 103) | KKKAKQBKAKHRWPKXXC |
| P38 (SEQ ID NO: 104) | KAKAKQBKKKHRWPKXXC |
| P39 (SEQ ID NO: 105) | KAKAKQBKAKHRWPKXXC |
| P40 (SEQ ID NO: 87) | KKKKKQBKKKHRWP |

wherein X is 6-amino hexanoic acid, B is β-alanine, and C is covalently bound to another C by $L^1$;

wherein $L^1$ is

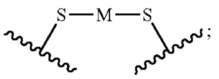;

M is

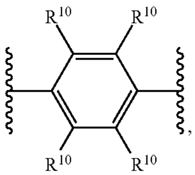, 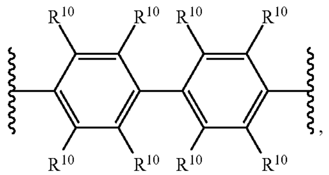, or

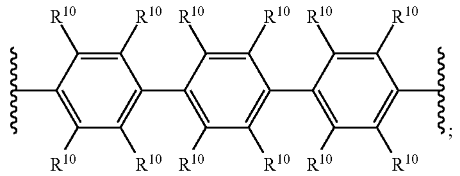;

and

In one embodiment, z is 8-30. In another embodiment, z is 10-30. In a further embodiment, z is 15-25. In another embodiment, z is 20-25. In an embodiment, z is 8, 9, 10, 11, 12, 13, 14, 15, 16, 17, 18, 19, 20, 21, 22, 23, 24, 25, 26, 27, 28, 29, or 30.

In yet another embodiment, E' is selected from H, —$C_{1-6}$-alkyl, —C(O)$C_{1-6}$-alkyl, benzoyl, stearoyl, trityl, monomethoxytrityl, dimethoxytrityl, trimethoxytrityl, and

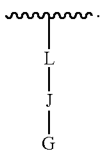.

In another embodiment, A' is selected from —N($C_{1-6}$-alkyl)$CH_2C(O)NH_2$,

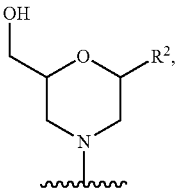, 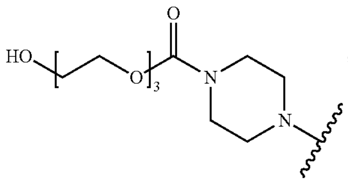, and 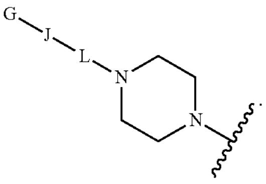.

In still another embodiment, E' is selected from H, —$C(O)CH_3$, benzoyl, stearoyl, trityl, 4-methoxytrityl, and

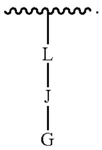.

In yet another embodiment, A' is selected from —N($C_{1-6}$-alkyl)$CH_2C(O)NH_2$,

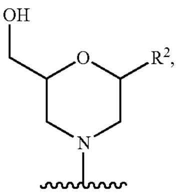, and

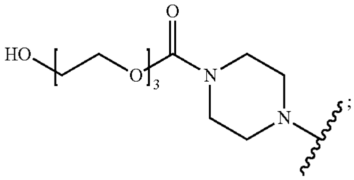; and E' is 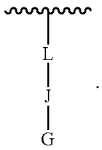.

In another embodiment, A' is

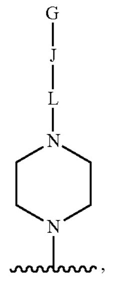

and

E' is selected from H, $-C(O)CH_3$, trityl, 4-methoxytrityl, benzoyl, and stearoyl.

In an embodiment, the peptide-oligonucleotide conjugate of Formula IA is a peptide-oligonucleotide conjugate of Formula Ia:

(Ia)

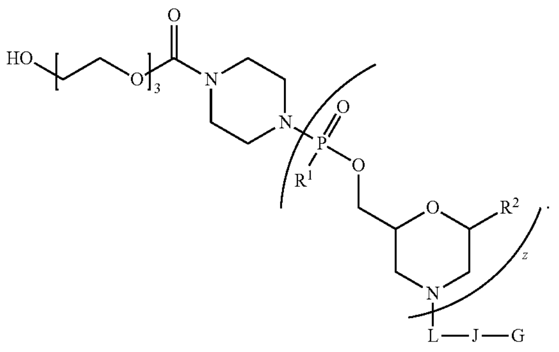

In an embodiment, the peptide-oligonucleotide conjugate of Formula IA is a peptide-oligonucleotide conjugate of Formula Ib:

(Ib)

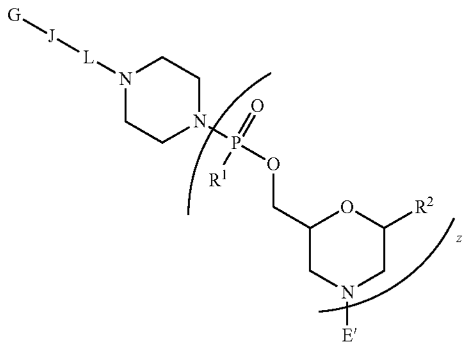

wherein E' is selected from H, $C_{1-6}$-alkyl, $-C(O)CH_3$, benzoyl, and stearoyl.

In an embodiment of Formula II, I, Ia, and Ib, each $R^1$ is $N(CH_3)_2$.

In yet another embodiment of Formula II, I, Ia, and Ib, each $R^2$ is a nucleobase, wherein the nucleobase independently at each occurrence comprises a $C_{4-6}$-heterocyclic ring selected from pyridine, pyrimidine, triazinane, purine, and deaza-purine.

In another embodiment of Formula II, I, Ia, and Ib, each $R^2$ is a nucleobase, wherein the nucleobase independently at each occurrence comprises a $C_{4-6}$-heterocyclic ring selected from pyrimidine, purine, and deaza-purine.

In still another embodiment of Formula II, I, Ia, and Ib, each $R^2$ is a nucleobase independently at each occurrence selected from adenine, 2,6-diaminopurine, 7-deaza-adenine, guanine, 7-deaza-guanine, hypoxanthine, cytosine, 5-methyl-cytosine, thymine, uracil, and hypoxanthine.

In yet another embodiment of Formula II, I, Ia, and Ib, each $R^2$ is a nucleobase independently at each occurrence selected from adenine, guanine, cytosine, 5-methyl-cytosine, thymine, uracil, and hypoxanthine.

In another embodiment of Formula II, I, Ia, and Ib, L is $-C(O)(CH_2)_{1-6}$-DBCO$-(CH_2)_{1-6}C(O)-$.

In another embodiment of Formula II, I, Ia, and Ib, L is

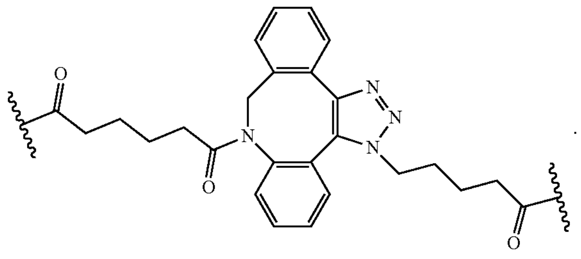 [SMILES: *C(=O)CCCCC(=O)N1Cc2ccccc2-c2nnn(CCCCC(*)=O)c2-c2ccccc21]

In another embodiment of Formula II, I, Ia, and Ib, M is

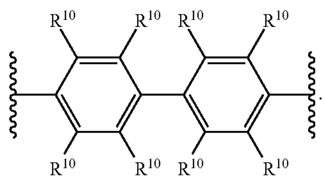

In yet another embodiment of Formula II, I, Ia, and Ib, M is

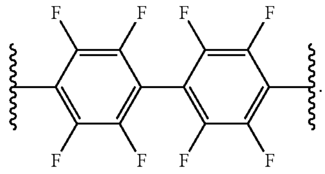

In another embodiment of Formula II, I, Ia, and Ib, $L^1$ is covalently-linked to the side chain of a terminal cysteine on $P^1$ and $P^2$ to form the structure:

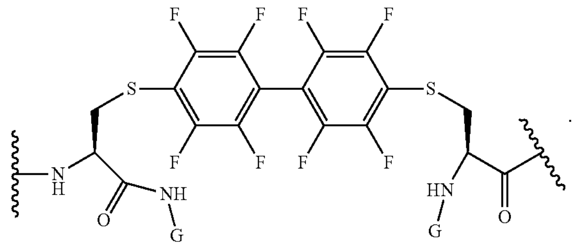

In another embodiment of Formula II, I, Ia, and Ib, G is selected from H, $C(O)CH_3$, benzoyl, and stearoyl.

In still another embodiment of Formula II, I, Ia, and Ib, G is H or —$C(O)CH_3$.

In yet another embodiment of Formula II, I, Ia, and Ib, G is H.

In yet another embodiment of Formula II, I, Ia, and Ib, G is —$C(O)CH_3$.

In yet another embodiment of Formula II, I, Ia, and Ib, the oligonucleotide-peptide conjugate demonstrates at least a 40-fold improvement in uptake as compared to unconjugated oligonucleotide.

In a further embodiment of Formula II, I, Ia, and Ib, the oligonucleotide-peptide conjugate demonstrates at least a 5-fold improvement in uptake as compared to unconjugated oligonucleotide.

In an embodiment, the oligonucleotide-peptide conjugate is non-toxic.

In another embodiment, the oligonucleotide-peptide conjugate is nonimmunogenic.

Trimeric Peptides

In particular embodiments, trimeric peptides are useful for creating a library of training oligonucleotide-cell-penetrating peptide conjugates.

A non-limiting representation of such a trimeric peptide is shown below:

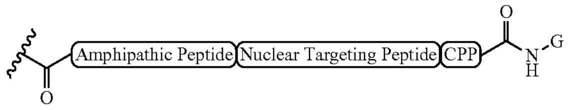

N-terminus C-terminus wherein the C-terminus is covalently attached to an oligonucleotide.

In an embodiment, each trimeric peptide is three covalently-linked cell-penetrating peptides, wherein the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In another embodiment, each trimeric peptide is three covalently-linked cell-penetrating peptides, wherein one of the cell-penetrating peptides is an amphipathic peptide, one of the cell-penetrating peptides is an nuclear targeting peptide, and one of the peptides is an additional cell-penetrating peptide.

In still another embodiment, each trimeric peptide is three covalently-linked cell-penetrating peptides, wherein the three cell-penetrating peptides comprise one amphipathic peptide, one nuclear targeting peptide, and one additional cell-penetrating peptide, and wherein the amphipathic peptide is the N-terminus of trimeric peptide, the nuclear targeting peptide is the middle peptides, and the addition cell-penetrating peptide is the C-terminus of trimeric peptide.

In still another embodiment, the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

In an embodiment, the hydrophophilic peptidyl segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

Provided in Table 2 are various, non-limiting, embodiments for the peptides of the trimeric peptide:

TABLE 2

Various embodiments of CPPs.

| Peptide Name | Sequence | SEQ ID NO. |
|---|---|---|
| DPV6 | GRPRESGKKRKRKRLKP | 1 |
| PPC5 | GRKAARAPGRRKQ | 3 |
| R12 | RRRRRRRRRRRR | 4 |
| R12 full cycle | CRRRRRRRRRRRRC | 5 |
| R12 N-cycle | CRRRRRRCRRRRRR | 6 |
| R12 C-cycle | RRRRRRCRRRRRRC | 7 |
| R12 benzyl bicycle | CRRRRRRCRRRRRRC | 8 |
| R12 double cycle | CRRRRRRCCRRRRRRC | 9 |
| Bpep | RXRRBRRXRRBR | 10 |
| Bpep full cycle | CRXRRBRRXRRBRC | 11 |
| Bpep C-cycle | RXRRBRCRXRRBRC | 12 |
| Penetratin (nle) | RQIKIWFQNRRMKWKK | 13 |
| Engrailed N-cycle | CQIKIWFCNKRAKIKK | 14 |

TABLE 2-continued

Various embodiments of CPPs.

| Peptide Name | Sequence | SEQ ID NO. |
|---|---|---|
| Engrailed C-cycle | SQIKIWFQ**C**KRAKIK**C** | 15 |
| Engrailed full cycle | **C**SQIKIWFQNKRAKIKK**C** | 16 |
| pVEC | LLIILRRRIRKQAHAHSK | 17 |
| pVEC-Bpep | LLIILRRRIRKQAHAHSKRXRRBRRXRRBR | 18 |
| AIP6 full cycle | Z**C**RLRWR**C** | 19 |
| Melittin-Bpep | GIGAVLKVLTTGLPALISWIKRKRQQRXRRBRRXRRBR | 20 |
| Bh3 helix | IWIAQELRRIGDEFNAYYARR | 21 |
| Bac7 | RRIRPRPPRLPRPRPRPLPFPRPG | 22 |
| Buforin 2 | TRSSRAGLQWPVGRVHRLLRK | 23 |
| Melittin | GIGAVLKVLTTGLPALISWIKRKRQQ | 24 |
| SynB1 | RGGRLSYSRRRFSTSTGR | 25 |
| S413-PVrev | ALWKTLLKKVLKAPKKKRKV | 26 |
| Ribotoxin2 L3 | KLIKGRTPIKFGKADCDRPPKHSQNGMGK | 27 |
| PreS2-TLM | PLSSIFSRIGDP | 28 |
| MAP | KLALKALKALKAALKLA | 29 |
| W/R | RRWWRRWRR | 30 |
| MAP12 | LKTLTETLKELTKTLTEL | 31 |
| SAP | VRLPPPVRLPPPVRLPPP | 32 |
| SVM1 | FKIYDKKVRTRVVKH | 33 |
| SVM3 | KGTYKKKLMRIPLKGT | 34 |
| SVM4 | LYKKGPAKKGRPPLRGWFH | 35 |
| YTA4 | IAWVKAFIRKLRKGPLG | 36 |
| 439a | GSPWGLQHHPPRT | 37 |
| HoxA 13 serine2 | RQVTIWSQNRRVKSKK | 38 |
| Bip | VSALK | 39 |
| PPR3 | PPRPPRPPR | 40 |
| PPR4 | PPRPPRPPRPPR | 41 |
| AIP6 | RLRWR | 42 |
| DPV15b | GAYDLRRRERQSRLRRRERQSR | 43 |
| TAT | RKKRRQRRR | 44 |
| Penetratin | RQIKIWFQNRRMKWKK | 45 |
| R9 | RRRRRRRRR | 46 |
| HoxA 13 serine1 | RSVTIWFQSRRVKEKK | 47 |
| KRVK TP10 | KRVKAGYLLGKINLKALAALAKKIL | 48 |
| TP10 KRVK | AGYLLGKINLKALAALAKKILKRVK | 49 |
| KRVK | KRVK | 50 |
| SV40 TP10 | PKKKRKVAGYLLGKINLKALAALAKKIL | 51 |

TABLE 2-continued

Various embodiments of CPPs.

| Peptide Name | Sequence | SEQ ID NO. |
|---|---|---|
| TP10 | AGYLLGKINLKALAALAKKIL | 52 |
| SV40 | PKKKRKV | 53 |
| AAV-PHP.eB | SDGTLAVPFKA | 54 |
| PPC3 | KKYRGRKRHPR | 55 |

Bolded cysteines are linked with decafluorobiphenyl. Italic cysteines are linked with 1,3,5-trisbromomethylbenzene.

Representative peptide-oligonucleotide-conjugates of the disclosure include, amongst others, trimeric peptide-oligonucleotide-conjugates of the following structure:

(IV)

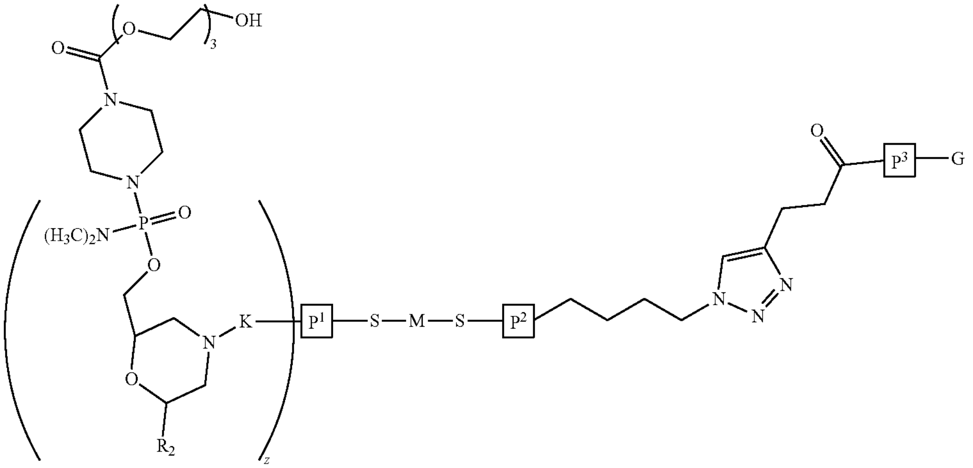

or a pharmaceutically acceptable salt thereof, wherein

G is H or —C(O)$CH_3$;

$R^2$ is a nucleobase, independently at each occurrence, selected from adenine, guanine, cytosine, 5-methylcytosine, thymine, uracil, and hypoxanthine; K is —C(O)$(CH_2)_{1-6}$—$C_{7-15}$-heteroaromatic-$(CH_2)_{1-6}$C(O)—;

M is

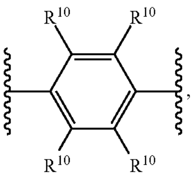

,

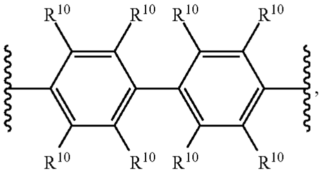

, or

-continued

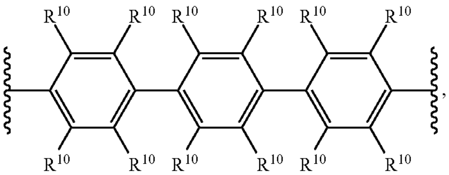

, and $R^{10}$ is independently at each occurrence H or a halogen, wherein $L^1$ is covalently-linked to the side chain of a terminal or internal cysteine on $P^1$ and $P^2$; z is 8-40; and $P^1$, $P^2$, and $P^3$ are each independently a cell-penetrating peptide, wherein $P^1$ and $P^2$ each comprise at least one cysteine amino acid residue, and wherein each of the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In an embodiment, the structure of Formula (IV) is Formula (IVa):

(IVa)

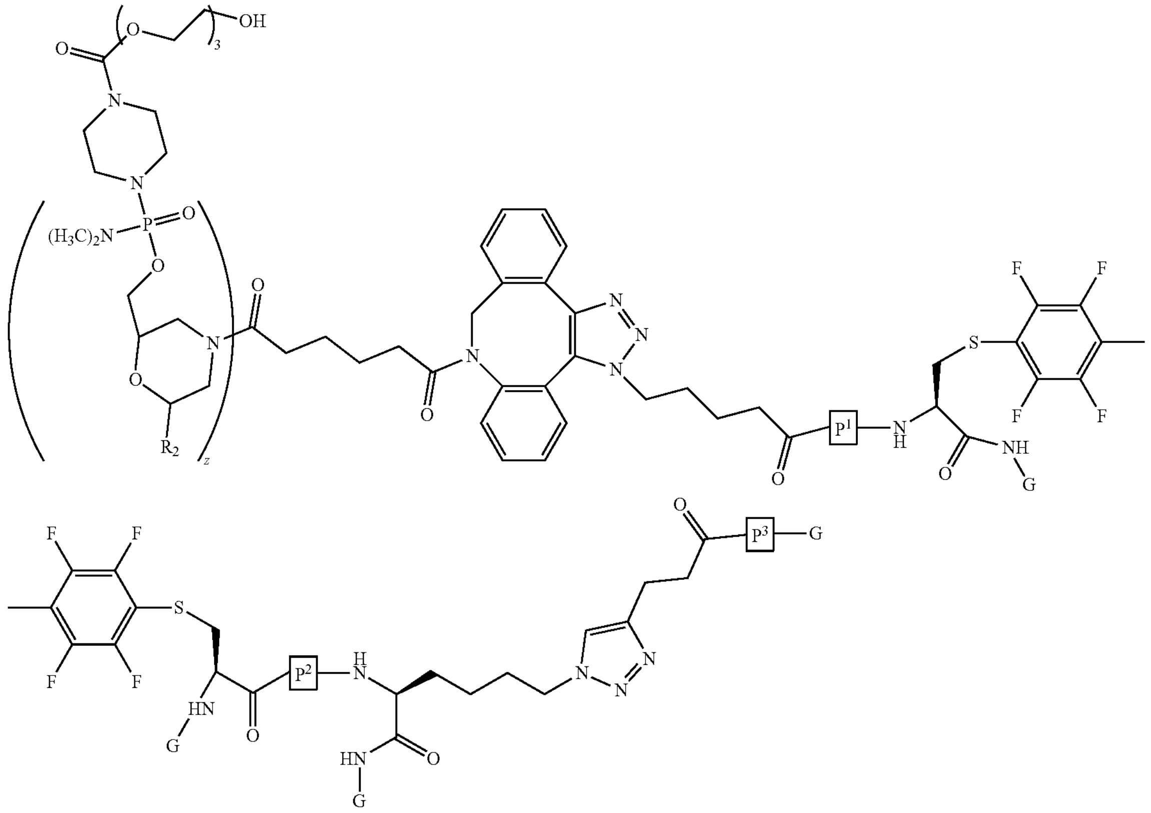

In one embodiment of the trimeric peptide-oligonucleotide-conjugates of the disclosure, G is H.

In another embodiment of the trimeric peptide-oligonucleotide-conjugates of the disclosure, G is —C(O)$CH_3$.

In some embodiments, the trimeric peptide-oligonucleotide-conjugates described herein are unsolvated. In other embodiments, one or more of the trimeric peptide-oligonucleotide-conjugates are in solvated form. As known in the art, the solvate can be any of pharmaceutically acceptable solvent, such as water, ethanol, and the like.

Although the peptide-oligonucleotide-conjugates of Formulae I, II, Ia, Ib, IV, and Va are depicted in their neutral forms, in some embodiments, these peptide-oligonucleotide-conjugates are used in a pharmaceutically acceptable salt form.

Oligonucleotides

Important properties of morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA, $T_M$ values above about 45° C. in relatively short oligonucleotides (e.g., 10-15 bases); 3) the ability of the oligonucleotide to be actively or passively transported into mammalian cells; and 4) the ability of the oligonucleotide and oligonucleotide:RNA heteroduplex to resist RNAse and RNase H degradation, respectively.

The stability of the duplex formed between an oligomer and a target sequence is a function of the binding $T_M$ and the susceptibility of the duplex to cellular enzymatic cleavage. The $T_M$ of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding $T_M$, with respect to a complementary-sequence RNA, of greater than body temperature and, in some embodiments greater than about 45° C. or 50° C. TMs in the range 60-80° C. or greater are also included. According to well-known principles, the $T_M$ of an oligomer, with respect to a complementary-based RNA hybrid, can be increased by increasing the ratio of C:G paired bases in the duplex, or by increasing the length (in base pairs) of the heteroduplex, or both. At the same time, for purposes of optimizing cellular uptake, it may be advantageous to limit the size of the oligomer. For this reason, compounds of the disclosure include compounds that show a high $T_M$ (45-50° C. or greater) at a length of 25 bases or less.

The length of an oligonucleotide may vary so long as it is capable of binding selectively to the intended location within the pre-mRNA molecule. The length of such sequences can be determined in accordance with selection procedures described herein.

Generally, the oligonucleotide will be from about 8 nucleotides in length up to about 50 nucleotides in length. For example, the length of the oligonucleotide (z) can be 8-38, 8-25, 15-25, 17-21, or about 18. It will be appreciated however that any length of nucleotides within this range may be used in the methods described herein.

In some embodiments, the antisense oligonucleotides contain base modifications or substitutions. For example, certain nucleo-bases may be selected to increase the binding affinity of the antisense oligonucleotides described herein. These include 5-substituted pyrimidines, 6-azapyrimidines and N-2, N-6 and 0-6 substituted purines, including 2-aminopropyladenine, 5-propynyluracil, 5-propynylcytosine and 2,6-diaminopurine. 5-methylcytosine substitutions have been shown to increase nucleic acid duplex stability by 0.6-1.2° C., and may be incorporated into the antisense oligonucleotides described herein. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2, 6-diaminopurine.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

In an embodiment of Formula I, II, Ia, Ib, IV, and IVa, $R^2$ is independently at each occurrence adenine, 2,6-diaminopurine, guanine, hypoxanthine, cytosine, 5-methylcytosine, thymine, uracil, and hypoxanthine; and each $R^1$ is $—N(CH_3)_2$.

Provided in Table 1 are various embodiments of nucleotide moieties as described herein.

TABLE 1

| Various embodiments of nucleotide moieties. | |
|---|---|
| A = | 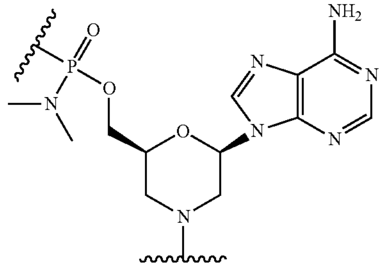 [SMILES: *N1C[C@@H](COP(*)(=O)N(C)C)O[C@@H](n2cnc3c(N)ncnc32)C1] |
| G = | 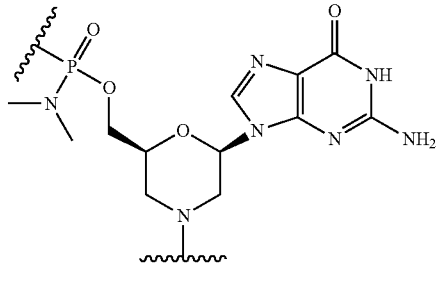 [SMILES: *N1C[C@@H](COP(*)(=O)N(C)C)O[C@@H](n2cnc3c(=O)[nH]c(N)nc32)C1] |

TABLE 1-continued

| Various embodiments of nucleotide moieties. | |
|---|---|
| C = | 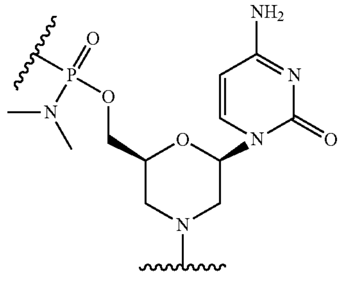 [SMILES: *N1C[C@@H](COP(*)(=O)N(C)C)O[C@@H](n2ccc(N)nc2=O)C1] |
| T = | 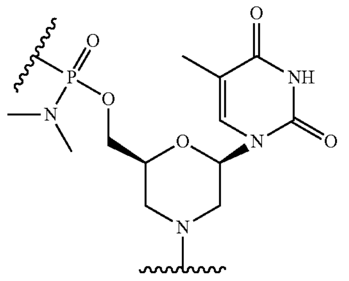 [SMILES: *N1C[C@@H](COP(*)(=O)N(C)C)O[C@@H](n2cc(C)c(=O)[nH]c2=O)C1] |
| 5-Me-C = | 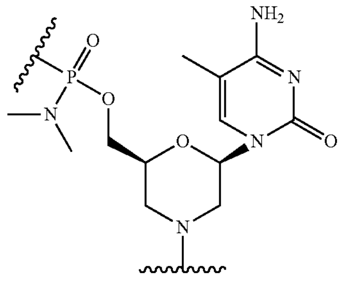 [SMILES: *N1C[C@@H](COP(*)(=O)N(C)C)O[C@@H](n2cc(C)c(N)nc2=O)C1] |
| I = | 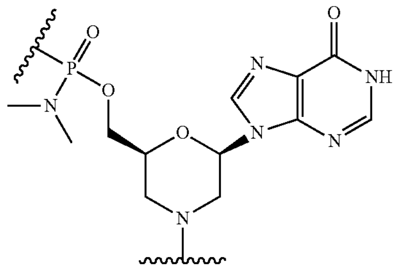 [SMILES: *N1C[C@@H](COP(*)(=O)N(C)C)O[C@@H](n2cnc3c(=O)[nH]cnc32)C1] |
| U = | 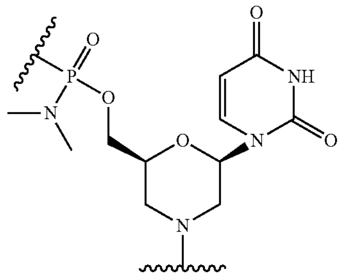 [SMILES: *N1C[C@@H](COP(*)(=O)N(C)C)O[C@@H](n2ccc(=O)[nH]c2=O)C1] |

In a particular embodiment, the sequence listing for the oligonucleotide is GCTATTACCTTAACCCAG (SEQ ID NO. 56).

In an embodiment, provided herein is a compound having the following structure:

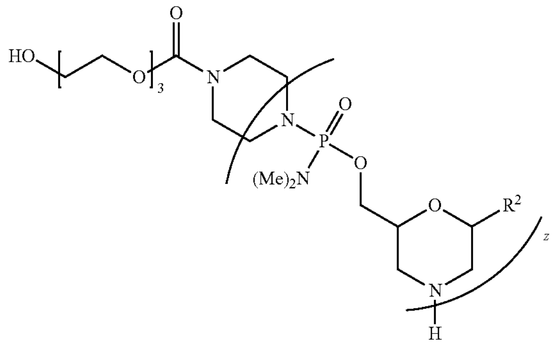

wherein z is 18 and $R^2$ is a sequence of nucleobases having the sequence of GCTATTACCTTAACCCAG (SEQ ID NO. 56). This compound is also referred to herein as "PMO IVS2-654."

In some embodiments, the oligonucleotides described herein are unsolvated. In other embodiments, one or more of the oligonucleotides are in solvated form. As known in the art, the solvate can be any of pharmaceutically acceptable solvent, such as water, ethanol, and the like.

Another aspect of the present invention relates to fluorescent dye, spin label, heavy metal or radio-labeled compounds of the invention that would be useful not only in imaging but also in assays, both in vitro and in vivo, for localizing and quantitating the target in tissue samples, including human, and for identifying target regions by inhibition binding of a labeled compound.

The present invention further includes isotopically-labeled peptides of the conjugates of the invention. An "isotopically" or "radio-labeled" conjugate is a conjugate of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to 2H (also written as D for deuterium), 3H (also written as T for tritium), 11C, 13C, 14C, 13N, 15N, 15O, 17O, 18O, 18F, 35S, 36Cl, 82Br, 75Br, 76Br, 77Br, 123I, 124I, 125I and 131I. The radionuclide that is incorporated in the instant radio-labeled compounds will depend on the specific application of that radio-labeled compound. For example, for in vitro IDO enzyme labeling and competition assays, compounds that incorporate 3H, 14C, 82Br, 125I, 131I, 35S or will generally be most useful. For radio-imaging applications 11C, 18F, 125I, 123I, 124I, 131I, 75Br, 76Br or 77Br will generally be most useful.

It is understood that a "radio-labeled" or "labeled compound" is a compound that has incorporated at least one radionuclide. In some embodiments the radionuclide is selected from the group consisting of 3H, 14C, 125I, 35S and 82Br.

Synthetic methods for incorporating radio-isotopes into organic compounds are applicable to compounds of the invention and are well known in the art.

A radio-labeled compound of the invention can be used in a screening assay to identify/evaluate compounds. Accordingly, the ability of a test compound to compete with the radio-labeled compound for binding directly correlates to its binding affinity.

Although the oligonucleotides of Formulas I, II, Ia, Ib, IV, and IVa are depicted in their neutral forms, in some embodiments, these oligonucleotides are used in a pharmaceutically acceptable salt form.

Method of Machine Learning

In an aspect, provided herein is a system and method for identifying one or more cell-penetrating peptides having optimal activity using machine learning, the method comprising:

a.) synthesizing a library of training oligonucleotide-cell-penetrating peptide conjugates;
b.) generating seed peptide sequences by training a nested long short-term memory (LSTM) recurrent neural network model using the synthesized library;
c.) predicting which peptide sequences from the generated seed peptide sequences have predetermined structure-activity relationships of amino acid residues; and
d.) identifying one or more optimal ones of the predicted peptide sequences using an activity predictor-genetic algorithm optimizer loop.

A functional system embodying this method is shown in FIG. 26 and comprises a library synthesizer module 2602, a generator network module 2604, a predictor network module 2606, and an optimization tool module 2608, each performing the respective function as described herein.

The output gate in LSTMs encodes the intuition that memories which are not relevant at the present time-step may still be worth remembering. Nested LSTMs use this intuition to create a temporal hierarchy of memories. Access to the inner memories is gated in exactly the same way, so that longer-term information which is only situationally relevant can be accessed selectively. In alternative aspects, the step of generating may be performed by alternate recurrent neural network (RNN) structures having other feedback connections for making predictions based upon time-series data, such as stacked LSTM and Gated Recurrent Unit (GRU) architectures.

In an embodiment, the predicting comprises comparing the seed sequences to chemical fingerprints of amino acid residues.

In a further embodiment, the predicting comprises representing an activity of the topological fingerprints as Conv1D, Conv2D, Conv2D Macrocycle, and DeConv2D convolutions.

In another embodiment, the activity is mean fluorescence intensity.

In an embodiment, the Conv1D convolution is trained on a one-dimensional representation of peptide sequences with a row matrix of amino acid fingerprints.

In a further embodiment, the Conv2D convolution is trained with an OR operation between individual fingerprints in a two-dimensional representation of peptide sequences.

In another embodiment, the Conv2D Macrocycle convolution is trained on a two-dimensional representation of peptide sequences with an explicit linker fingerprint in off-diagonal indices.

In a further embodiment, the DeConv2D convolution is trained on a two-dimensional variational representation with off-diagonal interaction weights determined by functionality for each off-diagonal index.

In another embodiment, the predicting comprises training the seed peptide sequences against mean fluorescence intensity using a convolutional neural network model.

In yet another embodiment, the identifying comprises the objective function of the activity predictor-genetic algorithm optimizer loop maximizing mean fluorescence intensity as predicted by the convolutional neural network model.

In an embodiment, the identifying comprises the objective function of the activity predictor-genetic algorithm optimizer loop minimizing sequence length and arginine content.

In a particular embodiment, the minimized arginine content is a single arginine residue.

In another particular embodiment, the minimized sequence length of the peptide is 20 or less residues.

In another embodiment, the genetic algorithm comprises single residue mutation with insertion or deletion and swapping or multi-residue mutation with insertion and/or deletion and swapping.

In an embodiment, the genetic algorithm implements an objective function:

$$\frac{1}{2}\text{Intensity} + \frac{1}{2}\left(-\frac{1}{2}Rcount - \frac{1}{5}\text{Length} + \frac{1}{10}\text{Net Charge}\right);$$

where

Intensity=Mean Fluorescence Intensity $R_{count}$=number of arginine residues

Length=sequence length

Net Charge=net charge of the subject sequence.

In an embodiment, the library of training oligonucleotide-cell-penetrating peptide conjugates is comprised of:

(a) contacting a compound of Formula (III)

(III)

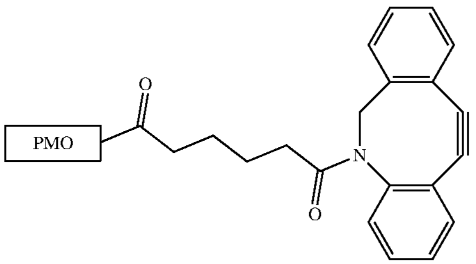

with a compound of Formula (IV)

(IV)

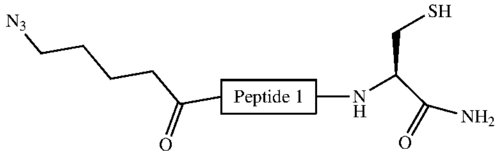

to form a compound of Formula (V)

(V)

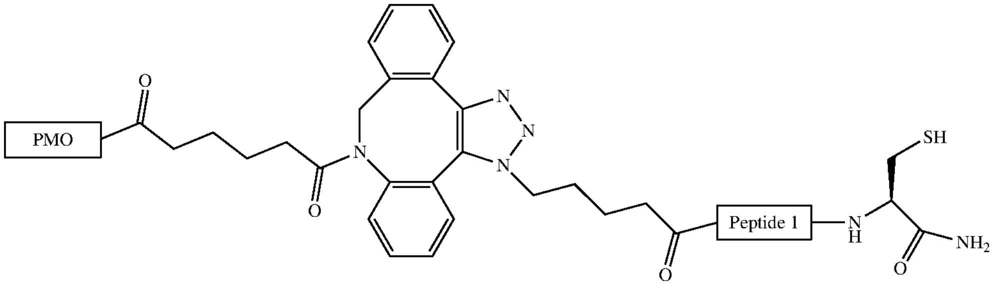

(b) contacting a compound of Formula (VI)

(VI)

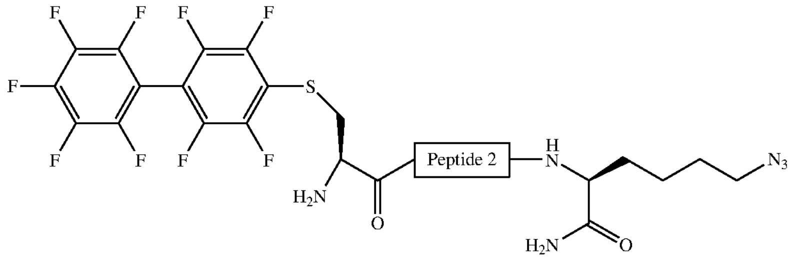

with a compound of Formula (VII)
(VII)
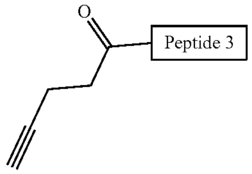
in the presence of a copper catalyst to form a compound of Formula (VIII)
(VIII)
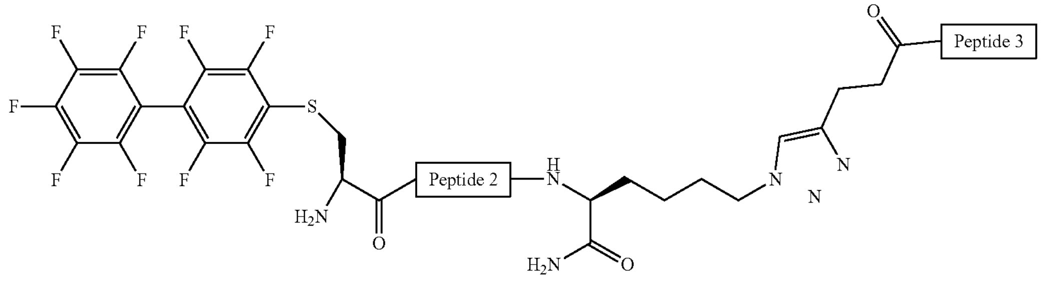
(c) contacting a compound of Formula (V)
(V)
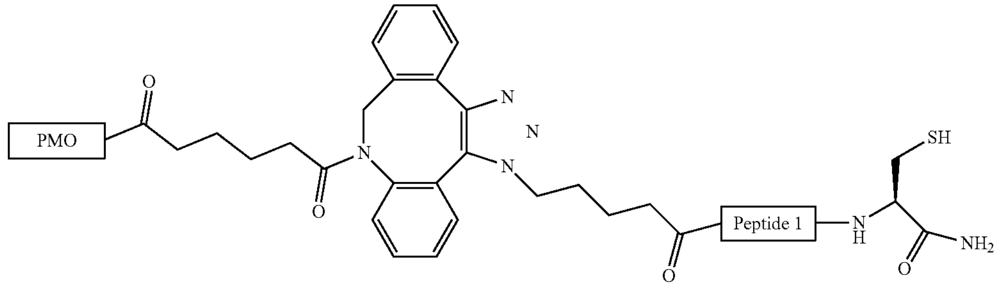
with a compound of Formula (VIII)
(VIII)
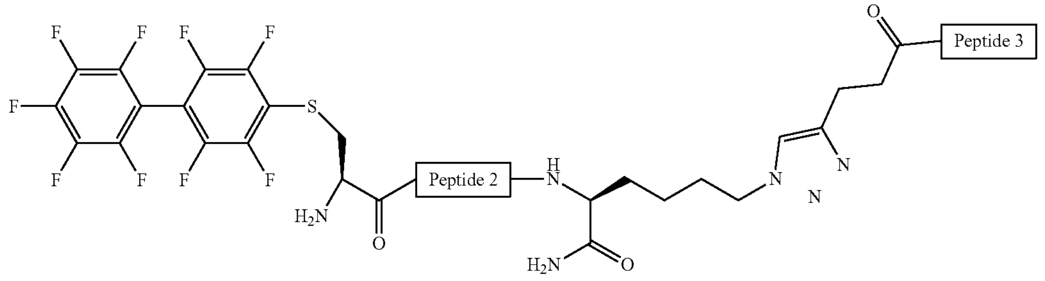
in the presence of a coupling reagent to form a compound of Formula (II)

(II)

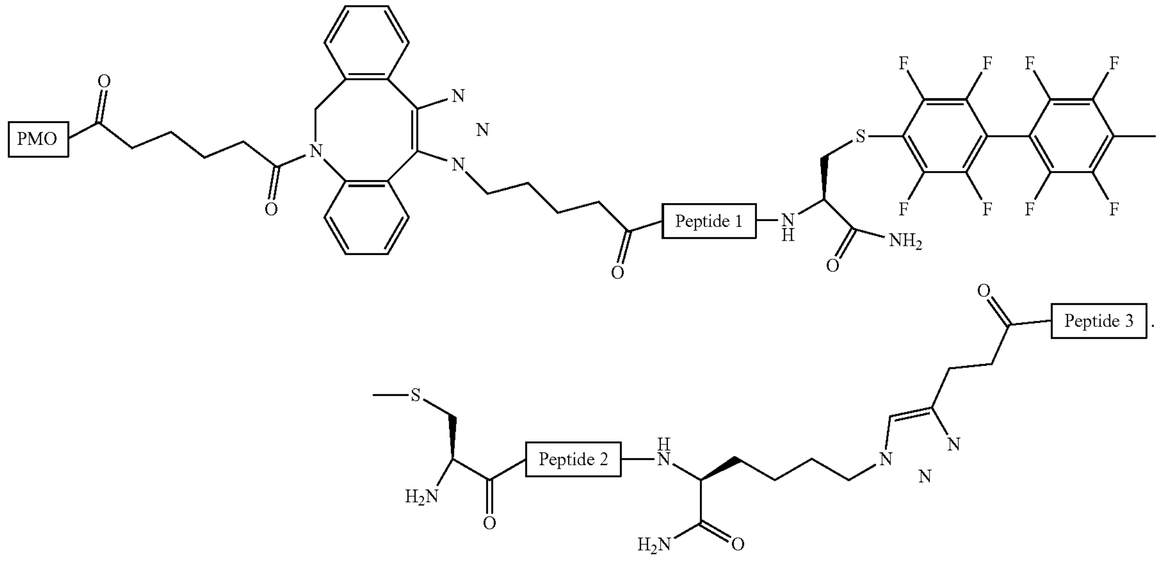

In an embodiment, peptide 1 ($P^1$), peptide 2 ($P^2$), and peptide 3 ($P^3$) are each, independently, a cell-penetrating peptide.

In another embodiment, $P^1$, $P^2$, and $P^3$ are cell-penetrating peptides, and the cell-penetrating peptides are independently an amphipathic peptide, a nuclear targeting peptide, an endosomal disrupting peptide, a chimeric peptide, a cyclic peptide, a bicyclic peptide, a cysteine-linked macrocyclic peptide, peptide containing at least one unnatural amino acid residue, or an oligoarginine peptide.

In an embodiment, the acid of step (a) is trifluoroacetic acid.

In another embodiment, the copper catalyst of step (b) is copper (I) bromide.

In yet another embodiment, the coupling reagent of step (c) is Tris(2-carboxyethyl)phosphine hydrochloride (TCEP).

In a further embodiment, the solvent for step (a) is water, the solvent for step (b) is water/DMSO, and the solvent for step (c) is water/DMSO.

In another embodiment, the products of steps (a) and (b) are inert to the reaction conditions of step (c).

In another embodiment, the products of steps (a) and (b) can be used in step (c) without any purification.

In a further embodiment, the final product is useful for immediate in vitro testing.

Shown in FIG. 25 is an example of a generalized computing device 2500 that can be used to implement the machine learning methodologies described herein. The generalized computing device 2500 is intended to represent various forms of digital computers, such as laptops, desktops, workstations, servers, mainframes, and other appropriate computers. The components shown here, their connections and relationships, and their functions, are meant to be examples only, and are not meant to be limiting.

Included within the computing device 2500 is a processor 2502, a memory 2504, a storage device 2506, a high-speed interface 2508 connecting to the memory 2504 and multiple high-speed expansion ports 2510, and a low-speed interface 2512 connecting to a low-speed expansion port 2514 and the storage device 2506, interconnected using various buses. The processor 2502 can process instructions for execution within the computing device 2500, including instructions stored in the memory 2504 or on the storage device 2506 to display graphical information for a graphical user interface (GUI) on an external input/output device, such as a display (not shown) coupled to the high-speed interface 2508. In other implementations, multiple processors and/or multiple buses may be used, as appropriate, along with multiple memories and types of memory. Further, multiple computing devices may be connected, with each device providing portions of the necessary operations (e.g., as a server bank or a multi-processor system).

The memory 2504 may be a volatile memory unit or units, and may be comprised of a non-volatile memory unit or units. The storage device 2506 may be capable of providing mass storage for the computing device 2500. For example, the storage device 2506 may be or contain a computer-readable medium, such as a hard disk device, an optical disk device, a flash memory or other similar solid-state memory device, or an array of devices, including devices in a storage area network or other configurations. Instructions stored within the storage device 2506, when executed by one or more processing devices, such as the processor 2502, perform one or more methods, such as those described herein. The instructions can also be stored by the memory 2504, the storage device 2506, or memory associated with the processor 2502.

The high-speed interface 2508 manages bandwidth-intensive operations for the computing device 2500, while the low-speed interface 2512 manages lower bandwidth-intensive operations. The high-speed interface 2508 may be coupled to the memory 2504, a display (not shown), and to the high-speed expansion ports 2510, which may accept various expansion cards (not shown). The low-speed interface 2512 may be coupled to the storage device 2506 and the low-speed expansion port 2514. The latter may include various communication ports, such as USB, Bluetooth, and/or Ethernet, which may be coupled to one or more input/output devices.

The computing device 2500 may be implemented in a number of different forms, such as a standard server or group of such servers. In addition, it may be implemented in a personal computer such as a laptop computer or as part of a rack server system. Alternatively, components from the computing device 2500 may be combined with other components in a mobile device (not shown), such as a mobile computing device.

Methods

Provided herein are methods of treating a neuromuscular disease, a muscle disease, a viral infection, or a bacterial infection in a subject in need thereof, comprising administering to the subject a peptide-oligonucleotide-conjugate of Formulae I, II, Ia, Ib, IV, or IVa.

Accordingly, in one aspect, provided herein is a method of treating a muscle disease, a viral infection, a neuromuscular disease or a bacterial infection in a subject in need thereof, comprising administering to the subject a chimeric peptide-oligonucleotide-conjugate of the present disclosure.

In one embodiment, the neuromuscle disease is Duchenne Muscular Dystrophy.

In another embodiment, the viral infection is caused by a virus selected from the group consisting of marburg virus, ebola virus, influenza virus, and dengue virus.

In another embodiment, the bacterial infection is caused by *Mycobacterium tuberculosis.*

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 μg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 μg to 100 g/kg of body weight, once or more daily, to once every 20 years.

In some embodiments, the conjugate of Formulae I, II, Ia, Ib, IV, or Va is administered alone.

In some embodiments, the conjugate of Formulae I, II, Ia, Ib, IV, or IVa is administered in a therapeutically effective amount or dosage. A "therapeutically effective amount" is an amount of the conjugate of Formulae I, II, Ia, Ib, IV, or Va that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the oligonucleotide that corresponds to a therapeutically effective amount is strongly dependent on the type of disease, stage of the disease, the age of the patient being treated, and other facts.

In different embodiments, depending on the conjugate of Formulae I, II, Ia, Ib, IV, or Va and the effective amounts used, the oligonucleotides can modulate the expression of a gene involved in a muscle disease, a viral infection, or a bacterial infection.

While the amounts of the conjugate of Formulae I, II, Ia, Ib, IV, or Va should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

The conjugate of Formulae I, II, Ia, Ib, IV, or IVa, or their pharmaceutically acceptable salts or solvate forms, in pure form or in an appropriate pharmaceutical composition, can be administered via any of the accepted modes of administration or agents known in the art. The oligonucleotides can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. In one embodiment, the oligomer is a phosphorodiamidate morpholino oligomer, contained in a pharmaceutically acceptable carrier, and is delivered orally. In another embodiment, the oligomer is a peptide-conjugated phosphorodiamidate morpholino oligomer, contained in a pharmaceutically acceptable carrier, and is delivered orally.

In another embodiment, the oligomer is a phosphorodiamidate morpholino oligomer, contained in a pharmaceutically acceptable carrier, and is delivered intravenously (i.v.). In another embodiment, the oligomer is a peptide-conjugated phosphorodiamidate morpholino oligomer, contained in a pharmaceutically acceptable carrier, and is delivered intravenously.

Additional routes of administration, e.g., subcutaneous, intraperitoneal, and pulmonary, are also contemplated by the instant disclosure.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active oligonucleotide or oligonucleotides in a certain part of the intestinal tract in a delayed manner. Examples of embedded compositions that can be used are polymeric substances and waxes. The active oligonucleotides also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the conjugates described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the oligonucleotides described herein, or a pharmaceutically acceptable salt thereof, and 99% to 1% by weight of a pharmaceutically acceptable excipient. In one example, the composition will be between about 5% and about 75% by weight of an oligonucleotide described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising oligonucleotides, peptides, peptide-oligonucleotide-conjugates, or compositions of the disclosure. In some embodiments, kits comprise a peptide-oligonucleotide-conjugate according to Formulae I, II, Ia, Ib, IV, or IVa, or a pharmaceutically acceptable salt thereof.

The phrase "package" means any vessel containing oligonucleotides or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering oligonucleotides or compositions of the disclosure to a patient. Kits also can comprise instructions for approved uses of oligonucleotides herein by regulatory agencies, such as the United States Food and Drug Administration. Kits can also contain labeling or product inserts for the oligonucleotides. The package(s) or any product insert(s), or both, may themselves be approved by regulatory agencies. The kits can include oligonucleotides in the solid phase or in a liquid phase (such as buffers provided) in a package. The kits can also include buffers for preparing solutions for conducting the methods, and pipettes for transferring liquids from one container to another.

Examples

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Library Synthesis

Figure 1:
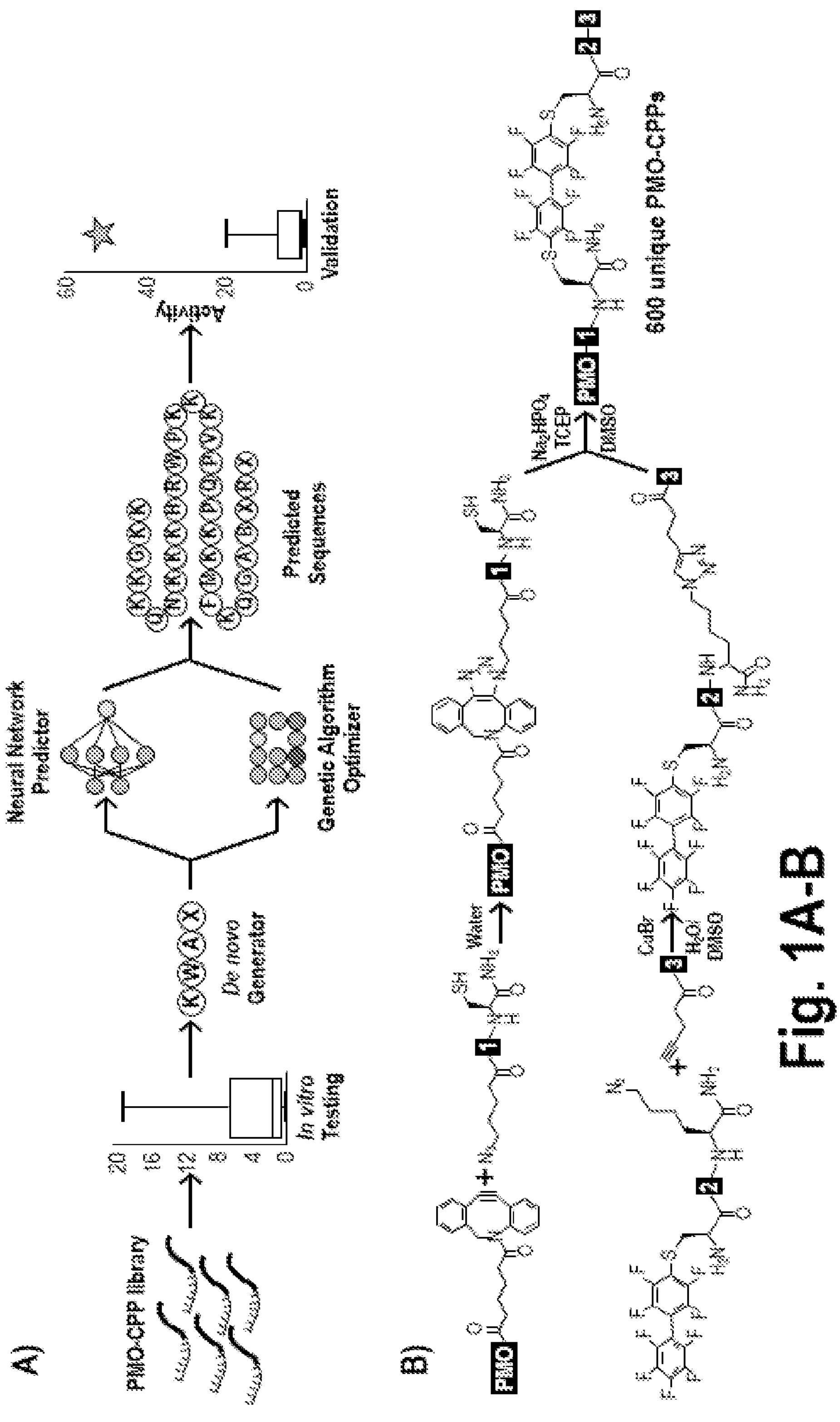
FIG. 1 A) shows the inverse design model. A modular PMO-CPP library that was tested for activity and used to train a machine learning algorithm to design novel highly active CPPs, which were then evaluated for activity and toxicity in vitro and in vivo. B) shows four modules that were combined using orthogonal bioconjugation.

With respect to FIG. 26, element 2602 and FIG. 27A, focus was placed on constructs containing four modules: one for the oligonucleotide and three for distinct peptide sequences. It was envisioned that it would be necessary for the modules to contain a variety of functional peptides, such as nuclear targeting peptides or endosomal disrupting peptides. To synthesize the constructs, a convergent approach was chosen, in which the Module 1 was linked to Module 2 and separately Module 3 was linked to Module 4. Then, the two dimers could be conjugated to provide a four-module construct (FIG. 1*b* and FIG. 27A, step 2700).

The choice of bioconjugation reactions was critical, as each reaction needed to be optimized to be tolerant of certain functional groups, compatible with common solvents and conditions, and suitable for peptide substrates. Several reactions were explored in the context of peptide conjugation and various limitations for certain reactions were encountered.

TABLE 3

List of functional groups used for common bioconjugation reactions, and the potential constraints on their use.

| Functional Group | Conjugation Constraints |
|---|---|
| Thiol | Can require reducing agent to prevent disulfide formation<br>Can react with DBCO |
| Maleimide | Reacts with azides<br>Linkage is reversible |

TABLE 3-continued

List of functional groups used for common bioconjugation reactions, and the potential constraints on their use.

| Functional Group | Conjugation Constraints |
|---|---|
| Alkyl Halide | Slow rate of reaction with thiols |
| Perfluoroarene | Unstable linkage above pH 10<br>Hydrophobic |
| Tetrazine | Reduces rapidly in presence of thiol or TIPS<br>Reacts with DBCO |
| Norbornene | Reacts with thiols during peptide cleavage<br>Reacts with azides |
| DBCO | Reacts with tetrazine, can react with thiols<br>Linker hydrolyzed in the presence of trifluoroacetic acid |
| Aldehyde | Intrinsically reversible |
| Alkyne | Reacts with palladium (e.g. during alloc removal) |
| Azide | Reduced by TCEP |

For example, it was found that tetrazines can be incorporated into a peptide on resin but are reduced during peptide cleavage and side-chain deprotection. Similarly, the tertiary amide present on commercially available DBCO reagents is cleaved in trifluoroacetic acid, requiring the incorporation of DBCO to substrates off-resin. Additionally, maleimides and azides will react when present on the same peptide.

After investigating several potential reactions, the final synthetic scheme combines two azide-alkyne cycloadditions with one $S_NAr$ reaction (FIG. 1*b*). In reaction 1, a PMO-DBCO will couple with an azido peptide to link modules 1 and 2. The azido peptide will also contain a free thiol, which under neutral conditions, will not react with DBCO. Separately, for reaction 2, a copper-catalyzed azide-alkyne cycloaddition will link modules 3 and 4. Module 3 will contain N-terminal cysteine residue linked to decafluorobiphenyl and a C-terminal azido-lysine. The perfluoroarene enables reaction 3 and also serves to prevent a free thiol from interfering with the azide/alkyne cycloaddition. Module 4 only contains an alkyne, which is stable towards most reactions, such as peptide macrocyclization. Lastly, in reaction 3, module 1-2 and 3-4 can be conjugated through a thiol-perfluoroarene $S_NAr$ reaction. Because the azides have already reacted with the alkynes, TCEP can be used to prevent disulfide formation without worrying about unintentional azide reduction.

The chosen synthetic scheme has numerous benefits for the synthesis of a combinatorial library. First, all reactions have been used in biological assays before to generate stable, irreversible linkages. Second, the reactions do not generate side-products and are theoretically quantitative, which reduces the need for purification. Third, all of the reagents are relatively benign and should not affect cell culture experiments. Although copper will be present, it was found that low micromolar concentrations of copper did not affect cell viability for the purposes of this screen. Lastly, the reactions can all be conducted at very small scale (e.g. volumes less than 5 μL). Notably, the combination of high yield and small volume suggests that the reactions can be performed at high concentrations and immediately diluted into media for cell culture treatment, without the need to purify each reaction individually.

After optimizing the individual reaction conditions, a set of 36 proof-of-concept constructs were synthesized for a modular library. For the oligonucleotide, module 1, PMO IVS2-654 (SEQ ID NO. 56), which upon successful delivery to the nucleus in a modified HeLa cell line, induces eGFP fluorescence was used. Module 2 included a set of four different CPPs: penetratin, pVEC, TP10, and DPV6. Module 3 included the KRVK (SEQ ID NO: 50) and SV40 nuclear localization sequences (NLS) and the peptide PHP.eB, a sequence recently reported to improve viral delivery into the brain. Module 4 included three CPPs: Bpep, DPV6, and PPC3 (FIG. 5).

The synthesis began with the conjugation of modules 1 and 2 using an azide-strained-alkyne cycloaddition. In water, 5 mM PMO-DBCO was incubated with 5 mM azide-module 2 peptide-cys. After one hour, the reaction was flash frozen in liquid nitrogen and the solvent was removed by lyophilization. For each reaction, LC-MS analysis showed nearly complete conversion to the product and indicated that the reaction proceeded cleanly with no need for purification.

Modules 3 and 4 were conjugated using copper-catalyzed azide-alkyne cycloaddition. The decafluorobiphenyl-module 3 peptide-azide and alkyne-module 4 peptide were dissolved in water to make a 10 mM stock solution of each module. Separately, copper (I) bromide was dissolved in DMSO under an inert atmosphere. The peptides were combined (final concentration of 3.3 mM each) and the reaction was initiated with the addition of copper bromide solution (final concentration 6.7 mM). After 2 hours, the reaction was quenched with the addition of 100 mM disodium phosphate in water. In preparation for reaction 3, the solvent was removed under vacuum.

Lastly, modules 1-2 and 3-4 were combined. Module 1-2 (final concentration 0.63 mM) was mixed with Module 3-4 (final concentration 1.25 mM, 2 equivalents) in DMSO containing 5 mM TCEP. Because Module 1 is the active component for cellular assays, it was used as the limiting reagent. After 2 hours, the reaction was flash frozen and stored at −80° C. until dilution and cell treatment. Testing the reaction components individually suggests that the presence of copper interferes with the reaction, and despite substantial attempts at optimization, reaction conversion never exceeded approximately 70%.

With the 36 constructs synthesized, the ability to modulate PMO activity using the modified HeLa cell assay was tested. The HeLa-654 cells were stably transfected to express a nonfluorescent eGFP protein. The eGFP gene is interrupted by a mutant intron from the human β-globin gene (IVS2-654). The insertion alters pre-mRNA splicing to cause retention of a fragment in the mature mRNA that results in a nonfluorescent protein. PMO IVS2-654 base-pairs with the β-globin insertion, modifies mRNA splicing, and thereby leads to expression of fluorescent eGFP.

For treatment, the crude reaction mixture was diluted to 5 μM in media. The concentration of the modular construct was calculated based on the original concentration of the module 1-2 conjugate mixed in the reaction. Using media containing 10% fetal bovine serum (FBS), the cells were treated with each construct for 22 hours, after which the cellular fluorescence was measured by flow cytometry.

Figure 6:
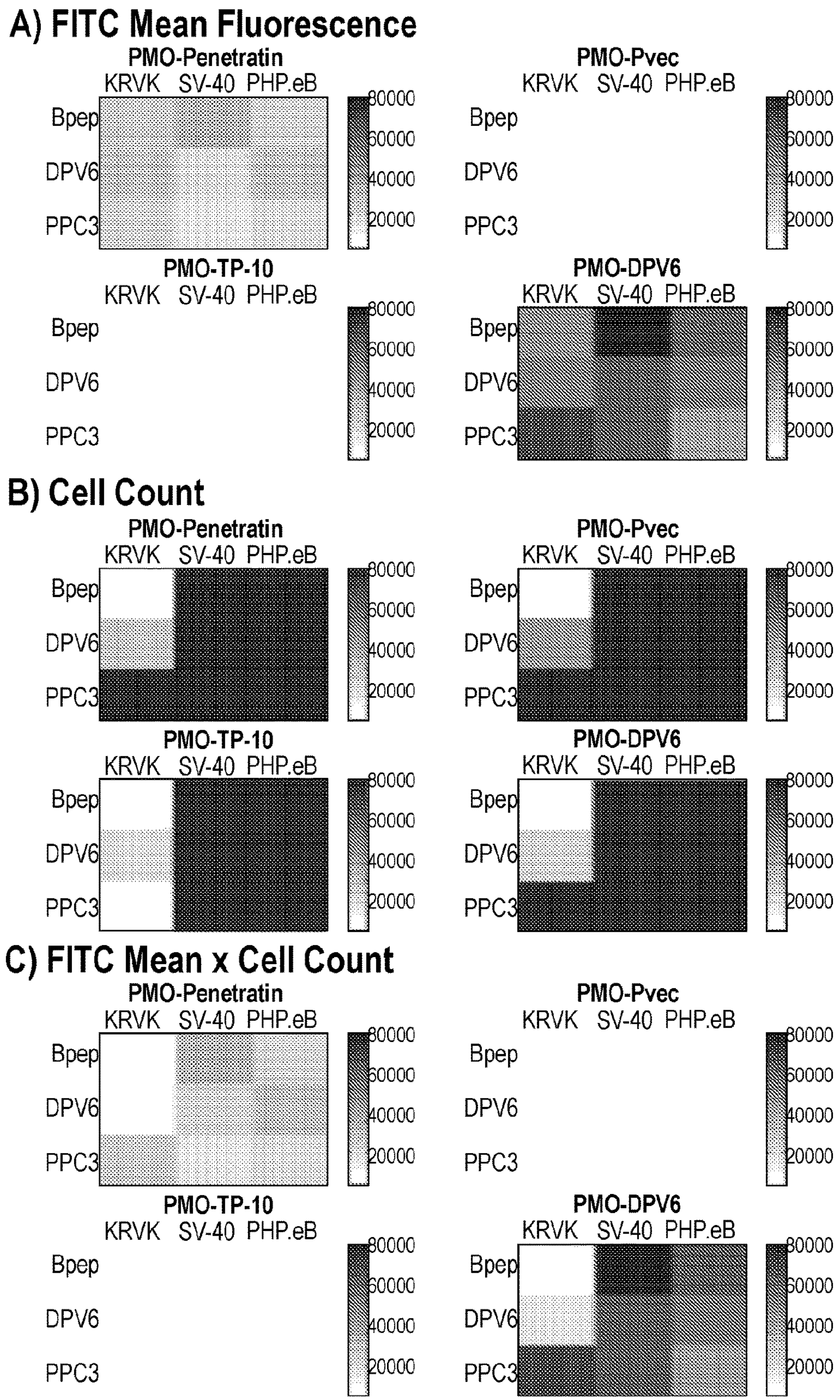
FIG. 6 A) shows heat maps disclosing the mean cellular fluorescence of HeLa-654 cells treated with each modular construct (n=3 replicate wells). B) Shows heat maps disclosing the total cell count of HeLa-654 cells after treatment with each modular construct. Each experiment was capped at 5000 cells. Low cell counts suggest cytotoxicity. C)

The different modules led to several noticeable trends in the level of cellular fluorescence (FIG. 6). When module 2 was DPV6, the overall construct consistently led to high fluorescence, regardless of which peptides were placed in module 3 and 4. However, when either pVEC or TP10 was placed in module 2, minor cellular fluorescence was observed. A gated cell count was used during flow cytometry as an indirect read-out to control for the toxicity of the compounds. Highly toxic compounds led to a reduction in overall cell count and non-viable cells were gated out based upon propidium iodide staining. In this experiment, it was observed that when the module 3 peptide was the nuclear localization sequence KRVK (SEQ ID NO: 50), lower cell counts were consistently observed. Since preferred compounds are both highly active and nontoxic, the cell fluorescence and cell count readings were multiplied together to obtain a measure of overall compound efficacy (FxC).

Given the success of the proof-of-concept experiment, a library of 600 conjugates for testing in the HeLa-654 cells was synthesized. It was chosen to increase the number of peptides in module 4 from 3 to 50. To increase the diversity of the types of peptides in the library and highlight the feasibility of incorporating modified peptides and unusual functional groups, a mixture of chimeric peptides, cyclic peptides, and bicyclic peptides were included. The cyclic peptides included R12, Bpep, and Engrailed variants in which two cysteine residues were linked to form a stable peptide macrocycle that are compatible with the modular reactions. The bicyclic variants included a double macrocyclic R12 and another R12 sequence where three side-chains were linked with 1,3,5-trisbromomethylbenzene. The other peptides included several previous reported CPPs, peptides computationally predicted to be effective PMO carriers (PPCs), and peptides with an appended NLS sequence (see Table 2.) With the additional compounds, reactions 1 and 2 were carried out as previously described, except reaction 2 now involved 150 distinct products. For reaction 3, to handle the large number of compounds, the synthesis was carried out over two days in 384 well plates, using the previously-described conditions. After synthesis, the compounds were diluted to 100 μM in PBS, and then to 5 μM in media containing 10% FBS. Again, HeLa-654 cells were treated with the construct for 22 hours and the cellular fluorescence was analyzed by flow cytometry (FIG. 7).

Machine Learning Model

Using the sequence and activity information from the modular library, as defined with respect to step 2700 of FIG. 27A, a series of interpretable machine learning models in order to predict novel, more effective sequences, were trained. The models may be implemented by a generalized computer system, such as shown in FIG. 25, or in a custom configured computing platform. A critical consideration for machine learning is the appropriate representation of input features and output parameters. Given the lack of any defined quantitative sequence-activity relationship that correlates amino acid chemical structure and sequence position with cell penetration, previous heuristic studies in the field have achieved limited success. Additionally, limitations in computational approaches often derive from the use of non-standardized datasets and physicochemical descriptors of peptides as features for machine learning over unrelated functional parameters. To overcome these limitations, an inverse design model using topological representations of peptide sequences to extract information from a uniform dataset, such as proposed above, was developed.

This inverse design model may also be referred to as a generator-predictor-optimizer machine learning model. A generator network produced realistic peptides, a predictor network addressed sequence-activity relationships using topological representations of molecules, and an optimization tool maximized activity while minimizing length and arginine content. Such a machine learning model is summarized in functional block form in FIG. 26.

This combination of addressing biological activity along with other design constraints resulted in optimized synthetic peptides that are non-toxic and non-immunogenic and that improved delivery of the PMO significantly.

Figure 2:
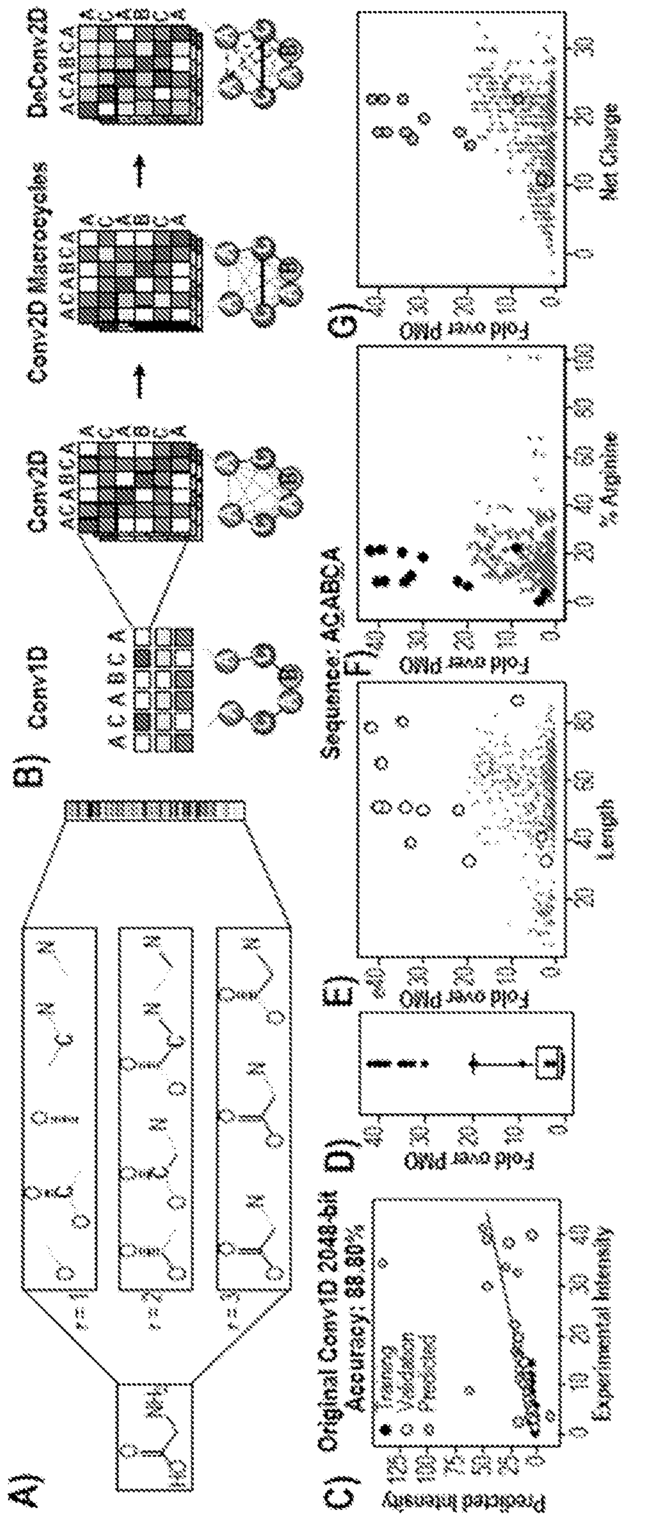
FIG. 2 A) shows amino acid residues that are represented as topological fingerprints. B) shows series of sequence representations: Conv1D (linear arrangement of fingerprints, representative of covalently bonded residues and local interactions), Conv2D (pairwise contact map of fingerprints, representative of a fully connected molecular graph), Conv2D Macrocycles (pairwise contact map of fingerprints with explicit information about cyclic covalent linkages, representative of a fully connected molecular graph with additional information), and DeConv2D (pairwise variational contact map with learned weights, representative of 3D interactions captured by learning over functionality values). C) shows comparison of predicted and experimentally observed MFI values for Original Conv1D model. D) shows fold improvement over PMO for sequences in training dataset (box plot) and validated (dots). E-G) shows key properties that were optimized over—length, percentage of arginine residues in the sequence, net charge of the sequence—compared with training and validated sequences against MFI.

In order to extract chemical information from each peptide, the atom connectivity of each amino acid sequence was characterized, rather than placing the peptides into bins of various physicochemical properties. First, with reference to FIG. 2*a*, amino acids and their modular linkers were represented as fingerprints encoding a topological exploration of neighboring atoms and bonds. Next, a series of 1D and 2D peptide sequence representations that treat sequences as linear (1D) and complete graphs (2D) was developed. The 1D representation captured the covalent, linear interactions along the peptide backbone, while the 2D representation introduced off-diagonal elements to represent folding, through-space interactions, and covalent linkages in macrocyclic sequences. The training data set, developed as discussed in the Library Synthesis section above, was composed of a modular library containing 600 peptides as well as other sequences previously tested in the eGFP assay. Sequences that resulted in low cell count due to toxicity were eliminated. The output from this assay was mean fluorescence intensity (MFI), linked to its respective graph representation.

For inverse design, a machine learning-based generator-predictor-optimizer loop was developed, as introduced above. The generator was based on a recurrent neural network, using a nested long short-term memory (RNN-Nested LSTM) architecture, capturing the grammatical intuitions of writing cell-penetrating peptide sequences (FIG. 27A, step 2702). This enabled the generation of novel similar-looking cell-penetrating peptide sequences. For the predictor, sequence representations were trained against MFI using convolutional neural network (CNN) models (FIG. 27B, step 2704). Finally, the optimization was done using genetic algorithms (GA) where the objective function involved maximization of MFI as predicted by the CNN model, and minimization of length and arginine content, while retaining water solubility (FIG. 27C, step 2706). These algorithm designs have evolved through several iterations, ultimately incorporating variational pixel maps and weighted, through-space interactions, including cysteine linkages (DeConv2D). Optimized predicted peptide sequences are provided (FIG. 27C, step 2708).

The original machine learning model based on Conv1D architecture was able to predict MFI with an accuracy of 89%, if the predicted value fell within the range of training values (0.32-19.5). After hyperparameter optimization and development of the model, the accuracy was increased to 92%.

To predict new sequences, seed sequences were generated using the trained Nested LSTM model, and optimized them in an activity predictor-genetic algorithm optimizer loop over an objective function to maximize MFI and minimize sequence length and arginine content. In addition, in order to observe the model's ability to predict peptides of certain activity sequences with poor activity for validation of a negative control were intentionally predicted, resulting in a class of synthetic peptides referred to as "Mach11."

It was determined that the predicted sequences shared no significant sequence similarity with any previously reported CPPs or any naturally occurring peptides and proteins, as determined by a protein-protein Basic Local Alignment Search Tool (BLASTp) homology search. Finally, an online tool (IEDB) was used to predict the probability of the predicted sequences to be immunogenic T cell epitopes and found predicted immunogenicity to be low according to set probability scores.

In order to interpret the design principles discovered by the algorithm, the chemical features that activated the learning of the Conv1D predictor were examined. To accomplish this, the positive gradient activations were examined for the input feature (sequence) with respect to the output (MFI) for the first convolution layer. Regions of higher activation in a layer indicate the specific features that led the neural network to make a particular prediction. It was observed that the predictor was mostly triggered by the amino acids towards the C-terminus of the peptide, and a preference for cationic residues was also noted. A detailed analysis of a highly active predicted sequence, Mach3, revealed a preference for the guanidinium-substructure within arginine. These motifs are consistent with previous empirical findings regarding cell penetration.

Figure 3:
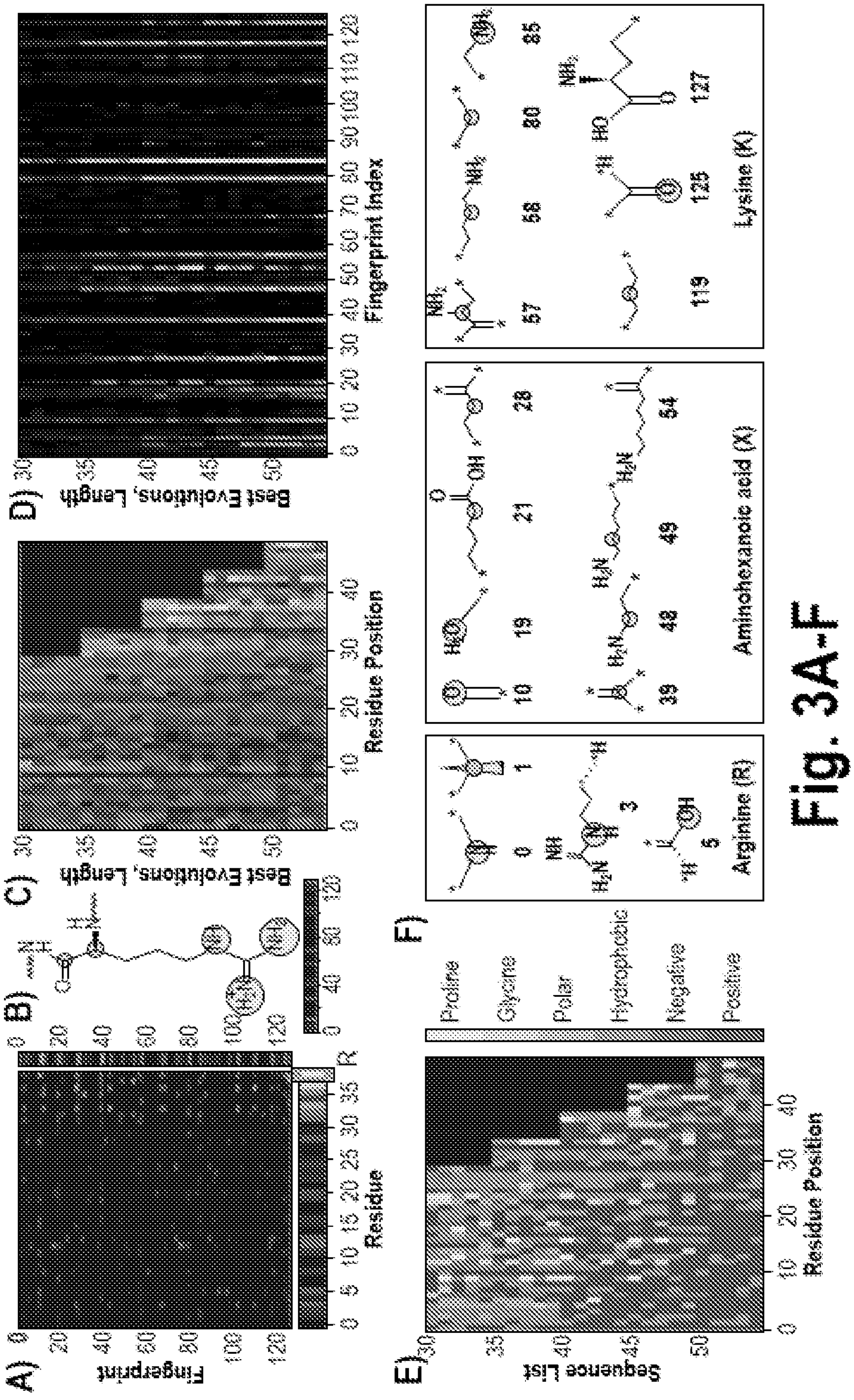
FIG. 3 A) shows a positive gradient map for Mach 3. B) shows positive substructures in the most positive residue in Mach3. Positive gradient activations for best sequences of particular length (30, 35, 40, 45, 50) averaged over C) residue position and D) Fingerprint Index. E) shows clustering of amino acids in the best performing sequences based on residue position. F) shows substructures for most activated fingerprint indices.

To better understand how the model was generating predictions, five random sequences were chosen of different lengths, seeded them in the optimizer, and visualized the best predictions. Positive activations were averaged over residue position (FIG. 3*c*) and chemical fingerprints (FIG. 3*d*). Further, the type of amino acid was analyzed based on residue position in the sequence (FIG. 3*e*) and the substructures highlighted in the fingerprints across residues (FIG. 30. A similar trend as Mach3 was observed for the higher performing training sequences.

Mach Peptides Enhance PMO Delivery

From the lists of hundreds of predicted peptide sequences, twenty candidates were selected that varied in length, charge, and predicted activity to synthesize and test. Just as with the PMO-peptide library, the PMO-Mach constructs were first tested for PMO delivery in the HeLa 654 assay at 5 μM in complete media for 22 hours and analyzed by flow cytometry (FIG. 14). Experiments were conducted using three technical triplicates and two or three biological replicates. Comparing the resulting activity to the training dataset and found that nearly all sequences surpassed the highest performing library peptide (FIG. 2*d*).

Predicted peptides diverse in length, charge, and structure were intentionally selected. Mach1 through Mach11 were linear PMO-peptide constructs. Mach12 and Mach13 contained two cysteines linked by decafluorobiphenyl to form an internal macrocycle. Sequences ranged from 33 to 80 amino acids in length, and +11 to +22 net charge. In addition, to confirm that the algorithm grasped design principles, it was made to predict sequences that would perform poorly. To this end, high-performing peptide, Mach1 had the algorithm rearrange the sequence such that the predicted activity decreased, resulting in Mach7. However, the experimental activities of the two constructs were nearly identical. Next, the algorithm designed a unique peptide predicted to have poor activity, resulting in Mach11. Indeed, Mach11 did not significantly improve PMO delivery. Notably, Mach5 did not significantly increase PMO activity although it was predicted to have similar activity as Mach 2 through 4.

Figure 4:
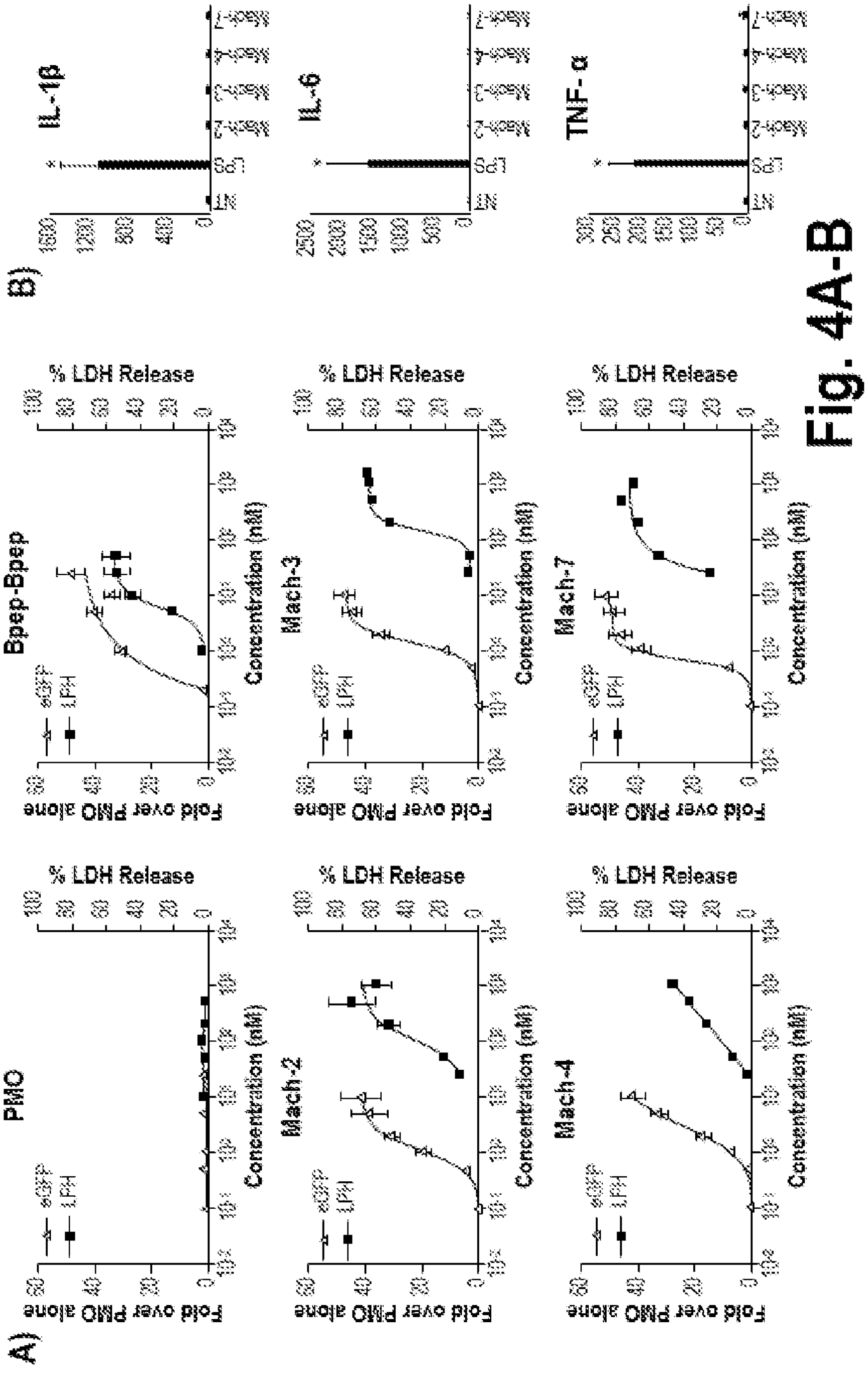
FIG. 4 A) shows dose-response curves for activity (corrective splicing in eGFP 654 HeLa cells) and toxicity (LDH release in RIPTEC cells) is shown for PMO alone, a known active peptide Bpep-Bpep, and four Mach peptides. Activity was determined using the eGFP assay: HeLa 654 cells were incubated with PMO-Mach constructs for 22 h before analysis by flow cytometry. Results are shown as fold increase relative to PMO alone, and was performed in as duplicate of technical triplicates. Toxicity was determined using renal epithelial cells (RPTEC TH1) treated in the same fashion and analyzed using LDH release assay. (*p<0.01, student's two-tailed t-test) B) shows Mach PMO-peptides do not trigger the release of pro-inflammatory cytokines as determined by an inflammatory cytokine panel in human macrophages. Human monocyte-derived macrophages were treated with each PMO-peptide at various concentrations for 3 h, washed, and incubated for 12 h. Released cytokines were detected via a bead-based immunoassay and flow cytometry.

Dose-response experiments with several highly active Mach peptides were performed (FIG. 4*a*). In the same format as described above, HeLa 654 cells were treated with varying concentrations of Mach 2, 3, 4, and 7 for 22 hours and analyzed by flow cytometry. Each construct had an $EC_{50}$ value near 1 μM and displayed no cytotoxicity at the concentrations tested, as determined by cell count and PI staining.

Example 1: General Method for Peptide Preparation and Purification

Fast-Flow Peptide Synthesis

Peptides were synthesized on a 0.1-mmol scale using an automated flow peptide synthesizer. A 200 mg portion of ChemMatrix Rink Amide HYR resin was loaded into a reactor maintained at 90° C. All reagents were flowed at 80 mL/min with HPLC pumps through a stainless-steel loop maintained at 90° C. before introduction into the reactor. For each coupling, 10 mL of a solution containing 0.2 M amino acid and 0.17 M HATU in DMF were mixed with 200 μL diisopropylethylamine and delivered to the reactor. Fmoc removal was accomplished using 10.4 mL of 20% (v/v) piperidine. Between each step, DMF (15 mL) was used to wash out the reactor. Special coupling conditions were used for arginine, in which the flow rate was reduced to 40 mL/min and 10 mL of a solution containing 0.2 M Fmoc-L-Arg(Pbf)-OH and 0.17 M PyAOP in DMF were mixed with 200 μL diisopropylethylamine and delivered to the reactor. To couple unnatural amino acids or to cap the peptide (e.g. with 4-pentynoic acid), the resin was incubated for 30 min at room temperature with 4-pentynoic acid (1 mmol) dissolved in 2.5 mL 0.4 M HATU in DMF with 500 μL diisopropylethylamine. After completion of the synthesis, the resin was washed 3 times with DCM and dried under vacuum.

Peptide Cleavage and Deprotection

Each peptide was subjected to simultaneous global side-chain deprotection and cleavage from resin by treatment with 5 mL of 94% trifluoroacetic acid (TFA), 2.5% 1,2-ethanedithiol (EDT), 2.5% water, and 1% triisopropylsilane (TIPS) (v/v) for 7 min at 60° C. For arginine-rich sequences, the resin was treated with a cleavage cocktail consisting of 82.5% TFA, 5% phenol, 5% thioanisole, 5% water, and 2.5% EDT (v/v) for 14 hours at room temperature. The TFA was evaporated by bubbling N2 through the mixture. Then −40 mL of cold ether (chilled at −80° C.) was added to precipitate and wash the peptide. The crude product was pelleted through centrifugation for three minutes at 4,000 rpm and the ether decanted. The ether precipitation and centrifugation were repeated two more times. After the third wash, the pellet was redissolved in 50% water and 50% acetonitrile containing 0.1% TFA, filtered through a fritted syringe to remove the resin and lyophilized.

Peptide Purification

The peptides were redissolved in water and acetonitrile containing 0.1% TFA, filtered through a 0.22 μm nylon filter and purified by mass-directed semi-preparative reversed-phase HPLC. Solvent A was water with 0.1% TFA additive and Solvent B was acetonitrile with 0.1% TFA additive. A linear gradient that changed at a rate of 0.5%/min was used. Most of the peptides were purified on an Agilent Zorbax SB C3 column: 9.4×250 mm, 5 μm. Extremely hydrophilic peptides, such as the arginine-rich sequences were purified on an Agilent Zorbax SB C18 column: 9.4×250 mm, 5 μm. Using mass data about each fraction from the instrument, only pure fractions were pooled and lyophilized. The purity of the fraction pool was confirmed by LC-MS.

Using the protocol of Example 1, the peptides of Table 2 were synthesized.

Example 2: PMO-DBCO Synthesis

PMO IVS-654 (50 mg, 8 μmol) was dissolved in 150 μL DMSO. To the solution was added a solution containing 2 equivalents of Dibenzocyclooctyne acid (5.3 mg, 16 μmol) activated with HBTU (37.5 μL of 0.4 M HBTU in DMF, 15 μmol) and DIEA (2.8 μL, 16 μmol) in 40 μL DMF (Final reaction volume=0.23 mL). The reaction proceeded for 25 min before being quenched with 1 mL of water and 2 mL of ammonium hydroxide. The ammonium hydroxide will hydrolyze any ester formed during the course of the reaction. After 1 hour, the solution was diluted to 40 mL and purified using reversed-phase HPLC (Agilent Zorbax SB C3 column:

21.2×100 mm, 5 μm) and a linear gradient from 2 to 60% B (solvent A: water; solvent B: acetonitrile) over 58 min (1% B/min). Using mass data about each fraction from the instrument, only pure fractions were pooled and lyophilized. The purity of the fraction pool was confirmed by LC-MS.

Example 3: Library Synthesis Conditions

Reaction 1

PMO-DBCO was dissolved in water at 10 mM concentration (determined gravimetrically). The module 2 peptides were dissolved in water containing 0.1% trifluoroacetic acid at 10 mM concentration (determined gravimetrically; the molecular weight was calculated to include 0.5 trifluoroacetate counter ions per lysine, arginine, and histidine residue). In a microcentrifuge tube, 50 μL of PMO-DBCO solution was mixed with 50 μL of module 2 peptide. The solution was mixed and the reaction was allowed to proceed for one hour. Then, the product was analyzed by LC-MS and the solvent was removed by lyophilization. Lastly, the product was resuspended in 100 μL of DMSO to provide a 5 mM solution and stored at −20° C.

Reaction 2

Stock solutions were prepared by dissolving module 3 peptides and module 4 peptides in water at 10 mM concentration (determined gravimetrically). For each reaction, 4 μL of module 3 peptide was mixed with 4 μL of module 4 peptide in a PCR tube. Separately, the copper bromide solution was prepared by mixing 1 mL of degassed DMSO with 2.8 mg copper (1) bromide under $N_2$ to afford a 20 mM solution. Under ambient conditions, 4 μL of the CuBr solution was added to the mixture of module peptides 3 and 4. The reaction was capped and the reaction was allowed to proceed for 2 hours; the small amount of $O_2$ present during reaction setup does not substantially impede reaction progress. After 2 hours, 2 μL of a 100 mM solution of $Na_2HPO_4$ was added. The PCR tube was then sonicated, vortexed, and centrifuged. To remove the solvent, the PCR tube was centrifuged under vacuum using a Savant SPD121P SpeedVac set at 35° C. for 2 hours. Lastly, the product was resuspended in 16 μL of DMSO to provide a 5 mM solution and stored at −80° C. The product was analyzed by LC-MS.

Reaction 3

The final modular construct was synthesized through the combination of module 1-2 and module 3-4. First, 1.6 μL of reaction 2 was added to a 384-well plate. Separately, 30 μL of reaction 1 was mixed with 15 μL of TCEP solution (100 mM TCEP-HCl in 50/50 water/DMSO containing 400 mM NaOH) and 75 μL DMSO. Then, 1.6 μL of the reaction 1 solution was added to reaction 2 in the 384 well plate. Each individual reaction ultimately contained 0.4 μL of reaction 1 (at 5 mM in DMSO), 1.6 μL of reaction 2 (at 5 mM in DMSO), 0.2 μL TCEP solution (at 100 mM in water/DMSO), and 1 μL DMSO. Excess reaction 2 was used to force the reaction to go to completion; the presence of copper hinders the efficiency of this conjugation. Reaction 1 was used as a limiting reagent to avoid excess PMO, which is the active component for the cell culture assays. The reaction was allowed to proceed for 2 hours, and then the plate was stored at −80° C. The reaction was analyzed by LC-MS.

Example 4: HeLa-654 eGFP Assay

HeLa 654 cells were maintained in MEM supplemented with 10% (v/v) fetal bovine serum (FBS) and 1% (v/v) penicillin-streptomycin at 37° C. and 5% $CO_2$. Eighteen hours prior to treatment, the cells were plated at a density of 5,000 cells per well in a 96-well plate in MEM supplemented with 10% FBS and 1% penicillin-streptomycin. The day of the experiment, the 384 well plate containing the crude reaction mixtures in DMSO was diluted to 100 μM by the addition of 16.8 μL of PBS to the 3.2 μL reaction mixture. Then, each construct was diluted to 5 μM in MEM supplemented with 10% FBS and 1% penicillin-streptomycin. Cells were incubated with each conjugate at a concentration of 5 μM for 22 hours at 37° C. and 5% $CO_2$. Next, the treatment media was aspirated the cells were incubated with Trypsin-EDTA 0.25% for 15 min at 37° C. and 5% $CO_2$, washed 1× with PBS, and resuspended in PBS with 2% FBS and 2 μg/mL propidium iodide. Flow cytometry analysis was carried out on a BD LSRII flow cytometer. Gates were applied to the data to ensure that cells that were highly positive for propidium iodide or had forward/side scatter readings that were sufficiently different from the main cell population were excluded. Each sample was capped at 5,000 gated events.

Analysis was conducted using Graphpad Prism 7. For each sample, the mean fluorescence intensity and the number of gated cells was measured (FIGS. 8 and 9) and the intensity multiplied by the cell number was calculated (FIG. 7).

In addition, analysis of the exon skipping activity of PMO-P1 through PMO-P7 measured in the eGFP assay performed with three different biological replicates (FIG. 18) indicated that PMO-P7 is the conjugate that displays the highest activity, with a 14-fold increase with respect to unconjugated PMO, which is comparable to the activity of PMO-Bpep. The second and third best performers among the conjugates of PMO with these 7 predicted peptides were PMO-P2 and PMO-P4 with a 9-fold and a 7-fold increase in activity respectively in comparison with unconjugated PMO. The rest of the conjugates, PMO-P1, PMO-P3, PMO-P5 and PMO-P6 showed a 4-fold increase or even lower activity. PMO-P7 showed superior activity to analogs PMO-P8 through PMO-P12 (FIG. 19). The KXXC motif at the C-terminus of a peptide does not lead to increase in PMO delivery (FIG. 20). PMO-P21 through PMO-P23 were also tested (FIG. 21) as well as P30 through P40 (FIG. 23).

Example 5: MTT Assay

Cell viability after treatment was determined using MTT (see FIG. 15*b*). HeLa 654 cells were treated with varying concentrations of PMO-peptide constructs for 22 hours at 37° C. and 5% $CO_2$. Two wells containing media only was used as a blank, two wells containing untreated cells was used as a negative control, and two wells containing cells treated with SDS was used as a positive control. The supernatant was transferred to a new 96-well plate and replaced with complete media lacking phenol red. 10 μL of MTT stock solution was added to each well and incubated for 4 hours. 100 μL of SDS-HCl was added to each well, mixed thoroughly, and incubated for 4 hours. Each sample was mixed again and its absorbance was read at 570 nm. The blank measurement was subtracted from each measurement, and cell viability was calculated as: % viability=100×Experimental (OD570)/No Treatment (OD570).

Example 6: LDH Release Assay

Cytotoxicity assays were performed in both HeLa 654 cells and human RPTEC (Human Renal Proximal Tubule Epithelial cells, ECH001, Kerafast, see FIG. 4*a* and FIG.

15*a*). RPTEC were maintained in high glucose DMEM supplemented with 10% (v/v) fetal bovine serum (FBS) and 1% (v/v) penicillin-streptomycin at 37° C. and 5% $CO_2$. Treatment of RPTEC was performed as with the HeLa 654 cells. After treatment, supernatant was transferred to a new 96-well plate.

To each well of the 96-well plate containing supernatant, described above, was added CytoTox 96 Reagent (Promega). The plate was shielded from light and incubated at room temperature for 30 minutes. Equal volume of Stop Solution was added to each well, mixed, and the absorbance of each well was measured at 490 nm. The blank measurement was subtracted from each measurement, and % LDH release was calculated as % cytotoxicity=100×Experimental LDH Release (OD490)/Maximum LDH Release (OD490).

Example 7: Inflammation Panel Assay

The inflammatory response triggered by the PMO-peptide conjugates was assayed by profiling inflammatory cytokine release after treatment of THP-1-derived macrophages (see FIG. 4*b* and FIG. 16). THP-1 cells (ATCC TIB-202) were grown in RPMI 1640 media supplemented with 10% (v/v) FBS, 1% (v/v) penicillin-streptomycin, L-glutamine, non-essential amino acids, sodium pyruvate at 37° C. and 5% $CO_2$. Two days before the experiment, THP-1 cells (450 k/mL) were treated with 25 nM phorbol 12-myristate 13-acetate (PMA) at 37° C. and 5% $CO_2$ for 24 hours to trigger differentiation into macrophages. Then, media was replaced with fresh RPMI media and the cells were incubated for another 24 hours. At this time the phenotype changed from suspension cells to strongly adherent cells. In the morning of the experiment, the supernatant was removed and macrophages were lifted by incubating in enzyme-free cell dissociation buffer (Thermo) for 5 minutes. Cells were then collected, spun down, and brought up in complete RPMI media to a cell density of 500 k/mL. 100 k cells were plated in each well of a 96-well plate, leaving the first two columns empty. Cells were allowed to re-adhere before treatment. Duplicate wells were treated with varying concentrations of the PMO-peptide conjugates at 37° C. and 5% $CO_2$ for 2 hours. Media-only and no treatment wells were used as negative controls, and 10 μg/mL bacterial lipopolysaccharide (LPS) treatment was used as a positive control. Following treatment, each well was washed three times, given fresh media, and incubated for 12 hours. Supernatant was transferred to a V-bottom plate and spun down at 4000 rcf to remove debris. Inflammatory cytokines in the supernatant were assayed using LEGENDplex Human Inflammation panel (BioLegend), a fluorescent bead-based assay. Cytokines assayed were: IL-1beta, IFN-alpha2, IFN-gamma, TFN-alpha, MCP-1, IL-6, IL-8, IL-10, IL-12p70, IL-17A, IL-18, IL-23, and IL-33. Analysis was carried out on a BD LSRII flow cytometer and data was analyzed using BioLegend's accompanying software.

Example 8: Recombinant Expression $His_6$-SUMO-$G_5$-DTA(C186S) was overexpressed in *E. coli* BL21 (DE3) cells (see FIG. 17). Approximately 10 g of cell pellet was lysed by sonication in 50 mL of 20 mM Tris, 150 mM NaCl, pH 7.5 buffer containing 30 mg lysozyme, 2 mg DNAase I, and 1 tablet of complete Protease Inhibitor Cocktail. The suspension was centrifuged at 16,000 rpm for 30 mins to remove cell debris. The supernatant was loaded onto a 5 mL HisTrap FF Ni-NTA column (GE Healthcare, UK) and washed with 30 mL of 100 mM imidazole in 20 mM Tris, 150 mM NaCl, pH 8.5. Protein was eluted from the column with buffer containing 300 mM imidazole in 20 mM Tris, 150 mM NaCl, pH 8.5. Imidazole was removed from protein via centrifugation in Millipore centrifugal filter unit (10K). The $His_6$-SUMO tag was then cleaved from the protein with SUMO protease (previously recombinantly expressed) by incubating a 1:1000 protease:protein ratio in 20 mM Tris, 150 mM NaCl, pH 7.5 overnight at 4° C. Desired protein was separated from $His_6$-SUMO tag by flowing the mixture through a 5 mL HisTrap FF Ni-NTA column. Finally purified protein was isolated by size exclusion chromatography using HiLoad 26/600 Superdex 200 prep grade size exclusion chromatography column (GE Healthcare, UK) in 20 mM Tris, 150 mM NaCl, pH 7.5 buffer.

Proteins were analyzed using an SDS-PAGE gel. In addition, proteins were analyzed by ESI-QTOF LCMS to confirm molecular weight and purity. The protein charge-state envelope was deconvoluted using Agilent Mass Hunter Bioconfirm using maximum entropy (Agilent Zorbax 300SB C3 column: 150×2.1 mm ID, 5 uM, 1% B 0-2 min, linearly ramp from 1% to 91% B 2 to 11 min, 91% to 9%% B 11 to 12 min, flow rate: 0.8 mL/min).

Example 9: Immunogenicity

Immunogenicity of the sequences (see FIG. 12) was calculated using an online server. The score is an arbitrary number, where a higher positive value indicates a higher probability of the peptide to be immunogenic and vice-versa. For the unnatural residues, B (3-alanine) and X (6-aminohexanoic acid) were replaced by a (alanine) and L (leucine) respectively for the search operation. It was seen that none of the peptides were expected to trigger an immune response.

Example 10: Inverse Design Model

Generator—Recurrent Neural Network. The generator is a data-driven tool to generate new peptide sequences that follow the 'ontology of cell penetrating peptides. To capture the basic rules, a Recurrent Neural Network was trained—Nested LSTM based model (see FIG. 1*a* and FIG. 10). The training dataset was comprised of 1150 sequences, including unique (non-modular) sequences used in the creation of the library and sequences from CPPSite2.0. (See also FIG. 26, element 2604 and FIG. 27A, step 2702).

Predictor—Convolutional Neural Network. The predictor estimates the fluorescence intensity from PMO delivery by a given peptide sequence, as measured in the HeLa 654 assay. The initial model (Original: Conv1D) was trained on a 1D representation of peptide sequences with a row matrix of amino acid fingerprints (see FIG. 2, FIG. 3, and FIG. 13). Next, a series of 2D representations to capture the long-range interactions was developed: (i) Conv2D—2D representation based on OR operation between individual fingerprints; (ii) Conv2D Macrocycle—2D representation with explicit linker fingerprint in off-diagonal indices; (iii) DeConv2D—2D variational representation with off-diagonal interaction weights determined by functionality for each off-diagonal index (see FIG. 11). All fingerprints were generated using RDKit. By combining the CPP library from this work as well as the collection of CPPs from previous work, 640 PMO-peptides sequences for training were compiled. (See also FIG. 26, element 2606 and FIG. 27B, step 2704).

Optimizer. The optimization was done using genetic algorithm (GA), where single residue mutations involved insertion, deletion and swapping, and multi-residue mutation was done using hybridization. Single residue mutation involved choosing the index of the residue, and deleting, or in the case of insertion/swapping, adding another residue, with all the processes being random. For hybridization, the sequence length and position to be hybridized, and the hybridized sequence (from the list of all CPPs) were all chosen randomly. The GA was implemented for the following objective function for all LSTM generated sequences for 1000 evolution steps:

$$\text{GA Score} = \frac{1}{2}\text{Intensity} + \frac{1}{2}\left(-\frac{1}{2}R_{count} - \frac{1}{5}\text{Length} + \frac{1}{10}\text{Net Charge}\right)$$

(See FIG. 26, element 2608 and FIG. 27C, step 2708).

Benchmark Models. Fingerprints and one-hot encodings were used to train benchmark models: support vector regression, Gaussian process regression, kernel ridge regression, k-nearest neighbors regression and XGBoost regression.

Hyperparameter Optimization. All hyperparameters for the generator and predictor models were optimized using SigOpt.

Using this model, a list of 13 peptides were prepared.

TABLE 4

List of synthesized predicted peptides.

| | | FOLD OVER PMO | FOLD OVER PMO* | % ARG | PPMO MW | NET CHARGE |
|---|---|---|---|---|---|---|
| MACH 1 (SEQ ID NO: 57) | ALKBRSAAKAVRWPKKKIK QASKKVAKYALXXXRKKK AASKXWLQLHWPRW | 45 | — | 8 | 12,645 | 18 |
| MACH 2 (SEQ ID NO: 58) | PPLRNAKKKNLKNNLKMD PKFTKKVKQGALKLNRRK KNRGPKGPXKHWTT | 27 | — | 8 | 12,499 | 18 |
| MACH 3 (SEQ ID NO: 59) | QKKRKSKANKKNWPKGKL SIHAKDYKQGPKAKXRKQ RXR | 38 | — | 10 | 11,324 | 17 |
| MACH 4 (SEQ ID NO: 60) | KKGKKQNKKKHRWPKKK VPQPKKMFKQGABXRX | 25 | — | 6 | 10,622 | 16 |
| MACH 5 (SEQ ID NO: 61) | AKKKIAKAKKHRGPNBGIH APVSKIKDPLKXXX | 3 | — | 8 | 11,590 | 11 |
| MACH 6 (SEQ ID NO: 62) | ALKBRSAAKAVRWPKKAIK QASKKVAKYALKXXRKKK AASKXWLQLHWPRW | 43 | — | 8 | 12,603 | 18 |
| MACH 7 (SEQ ID NO: 63) | XKHPXAVQBAARAWKVPA AALWKKKRLKKSSKQKKK WLWKARSAXKYXRLI | 36 | — | 8 | 12,645 | 18 |
| MACH 8 (SEQ ID NO: 64) | BKGKNLLAKIRRGPNGGN BQGSQGYLLYLLXRXRRQ RXXYPWWRXKHXRWXXR XRGHXRRRRQXLKPDRXR GGKGSVS | 39 | — | 21 | 15,929 | 22 |
| MACH 9 (SEQ ID NO: 65) | KKKKNLNBKSRRGPNGGA LQPSQGYLQPLNXRXRRQ RXXYPWWRXKHXRWRXR YHXRRRRQXLKPG | 38 | — | 21 | 14,845 | 22 |
| MACH 11 (SEQ ID NO: 66) | TSNLKLHLAPPVKKKALKK PLYKAKKKKKVVSPTWXT DQEW | 4 | — | 0 | 11,423 | 11 |
| MACH 12 (SEQ ID NO: 67) | KGGKNLAKKIRRGPNGGA LQPSQGYLLYLBXRXRRQ RXXGPXWRXKHXRWXXX XXRPTHXRRRRQXLCPGR XRPCRGSVS | 40 | — | 20 | 16,285 | 22 |
| MACH 13 (SEQ ID NO: 68) | AKKKKLGBKALRWPNGKC PQPKEKCPKYLLGRXRRK RXRYPWWRXKHRRW | 30 | — | 18 | 13,228 | 20 |

TABLE 4-continued

| List of synthesized predicted peptides. | | | | | | |
|---|---|---|---|---|---|---|
| | | FOLD OVER PMO | FOLD OVER PMO* | % ARG | PPMO MW | NET CHARGE |
| P1 (MACH 14) (SEQ ID NO: 69) | KXKKQQGKKKHR | 2.9 | 9 | 8 | 8,159 | 8 |
| P2 (MACH 15) (SEQ ID NO: 70) | KKKKKQBKKKHRWPMG | 8.2 | 10 | 6 | 8,660 | 10 |
| P3 (MACH 16) (SEQ ID NO: 71) | KKKKNQBKKKHRWPMKX CPQ | 3.7 | 13 | 5 | 9,158 | 10 |
| P4 (MACH 17) (SEQ ID NO: 72) | HKKKKQBKKKHRWP | 6.5 | 10 | 7 | 8,480 | 10 |
| P5 (MACH 18) (SEQ ID NO: 73) | KXKHQQQXK | 1.4 | 6 | 0 | 7,803 | 4 |
| P6 (MACH 19) (SEQ ID NO: 74) | KXKXT | 1.1 | 5 | 0 | 7,254 | 2 |
| P7 (MACH 20) (SEQ ID NO: 75) | KKKKKQBKKKHRWPKXXC | 17.7 | 11 | 6 | 8,929 | 11 |
| P8 (SEQ ID NO: 76) | KKKKKCBKKKHRWPKXXQ | 6.3 | — | 6 | 8,929 | 11 |
| P9 (SEQ ID NO: 77) | KKKXKQBKKKHRWPKKXC | 11.0 | — | 6 | 8,929 | 11 |
| P10 (SEQ ID NO: 78) | KCHKXKWKKPKRXKQKBK | 14.9 | — | 6 | 8,929 | 11 |
| P11 (SEQ ID NO: 79) | KKKKKQCKKKHRWPKXXC | 12.9 | — | 6 | 8,961 | 11 |
| P12 (SEQ ID NO: 80) | KKKKKQBKKKHRWPKXXG | 13.3 | | 6 | 8,883 | 11 |
| P13 (SEQ ID NO: 81) | KKKKKQBKKKHRWPMGK XXC | 8.9 | | 5 | 9,117 | 11 |
| P14 (SEQ ID NO: 82) | HKKKKQBKKKHRWPKXXC | 6.2 | | 6 | 8,938 | 11 |
| P15 (SEQ ID NO: 83) | KXKHQQQXKKXXC | 1.2 | | 0 | 8,260 | 5 |
| P16 (SEQ ID NO: 84) | KXKXTKXXC | 1.1 | | 0 | 7,712 | 3 |
| P17 (SEQ ID NO: 26) | ALWKTLLKKVLKAPKKKRK V | 15.3 | | 5 | 9,029 | 9 |

TABLE 4-continued

List of synthesized predicted peptides.

| | | FOLD OVER PMO | FOLD OVER PMO* | % ARG | PPMO MW | NET CHARGE |
|---|---|---|---|---|---|---|
| P18 (SEQ ID NO: 85) | ALWKTLLKKVLKAPKKKRK VKXXC | 6.0 | | 4 | 9,487 | 10 |
| P19 (SEQ ID NO: 45) | RQIKIWFQNRRMKWKK | 8.2 | — | 19 | 8,899 | 7 |
| P20 (SEQ ID NO: 86) | RQIKIWFQNRRMKWKKKX XC | 10.5 | — | 15 | 9,357 | 8 |
| P21 (SEQ ID NO: 87) | KKKKKQBKKKHRWP | 14.0 | | 7 | 8,471 | 10 |
| P22 (SEQ ID NO: 88) | KKKKKQBKKKHRWPKXXC CC | 5.6 | | 5 | 9,135 | 11 |
| P23 (SEQ ID NO: 89) | KKKKKQBKKKHRWAKXXC | 12.7 | | 6 | 8,903 | 11 |
| P24 (SEQ ID NO: 90) | KXKHQQGP | — | 6 | 0 | | 2 |
| P25 (SEQ ID NO: 91) | KXKHQQGKKT | — | 6 | 0 | | 5 |
| P26 (SEQ ID NO: 92) | HKKKQQGKKKHRW | — | 9 | 8 | | 9 |
| P27 (SEQ ID NO: 93) | KKKKKQBKKKHRWPM | — | 10 | 7 | | 10 |
| P28 (SEQ ID NO: 94) | KKKKKQGKKHRWPMGG | — | 10 | 6 | | 9 |
| P29 (SEQ ID NO: 95) | KKKKNQBKKKHRWPMKX CP | — | 12 | 5 | | 10 |
| P30 (SEQ ID NO: 96) | KKKKKQBKKKHRWPKXXA | 17.0 | | 6 | | 10 |
| P31 (SEQ ID NO: 97) | KKKKKQBKKKHRWPKXAC | 16.8 | — | 6 | | 10 |
| P32 (SEQ ID NO: 98) | KKKKKQBKKKHRWPKAXC | 16.8 | — | 6 | — | 10 |
| P33 (SEQ ID NO: 99) | KKKKKQBKKKHRWPAXXC | 16.9 | — | 6 | — | 9 |
| P34 (SEQ ID NO: 100) | KAKKKQBKKKHRWPKXXC | 17.2 | — | 6 | — | 9 |
| P35 (SEQ ID NO: 101) | KKKKKQBKAKHRWPKXXC | 17.1 | | 6 | — | 9 |

TABLE 4-continued

List of synthesized predicted peptides.

| | | FOLD OVER PMO | FOLD OVER PMO* | % ARG | PPMO MW | NET CHARGE |
|---|---|---|---|---|---|---|
| P36 (SEQ ID NO: 102) | KKKAKQBKKKHRWPKXXC | 17.3 | | 6 | — | 9 |
| P37 (SEQ ID NO: 103) | KKKAKQBKAKHRWPKXXC | 17.5 | | 6 | — | 8 |
| P38 (SEQ ID NO: 104) | KAKAKQBKKKHRWPKXXC | 17.5 | | 6 | — | 8 |
| P39 (SEQ ID NO: 105) | KAKAKQBKAKHRWPKXXC | 17.6 | | 6 | — | 7 |
| P40 (SEQ ID NO: 87) | KKKKKQBKKKHRWP | 17.2 | | 7 | — | 9 |

*Predicted activity by machine learning method. **P8-P23 were designed or chosen for SAR studies.

wherein X is 6-amino hexanoic acid, B is β-alanine, and C is covalently bound to another C by $L^1$; wherein $L^1$ is

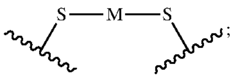

M is

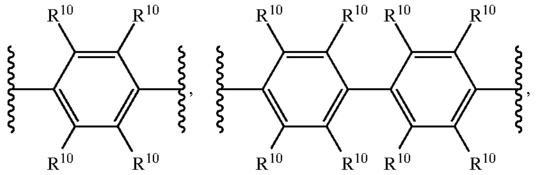

or

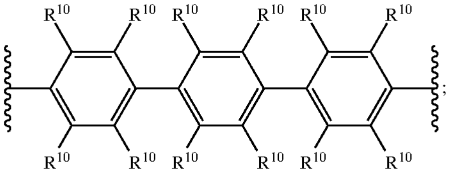

and $R^{10}$ is independently at each occurrence H or a halogen.

Example 11: Activity and Toxicity of PMO-P7, Dose-Response Curves

The half maximal effective concentration (EC50) of PMO-P7 was calculated by measuring the eGFP fluorescence (using HeLa654 cells) of this conjugate over PMO along a range of concentrations (between 0.1 and 100 μM). The resulting EC50 had a value of 4 M and the maximal effective concentration showed a 45-fold increase with respect to unconjugated PMO.

For the LDH assay, TH1 cells were maintained in DMEM-high glucose supplemented with 10% (v/v) FBS and 1% (v/v) Pen Strep at 37° C. and 5% $CO_2$. Eighteen hours before treatment, TH1 cells were plated at a density of 8,000 cells per well in a 96-well plate. The next day, fresh 10 mM stocks of each of PMO-peptide conjugate were prepared in PBS (1×). The concentration of the stocks was determined by measuring the absorbance at 260 nm and using an extinction coefficient of 168,700 L $mol^{-1}$ $cm^{-1}$. The growth media was aspirated from the cells and treatment media was added with each respective conjugate at different concentrations (between 1 and 200 M) in DMEM-high glucose supplemented with 10% FBS and 1% Pen Strep. The cells were incubated with treatment-containing media for 22 hours at 37° C. and 5% $CO_2$. Next, the supernatant treatment media was transferred to another clear-bottom 96-well plate for the assay. The assay was performed using the CytoTox 96® Non-Radioactive Cytotoxicity Assay (Promega) according to the included technical bulletin with the only difference of using half of the specified amounts (25 L of each supernatant, 25 μL of the LDH Reagent and 25 μL of the stop solution). The absorbance was measured on a BioTek Epoch Microplate Spectrophotometer at 490 nm. The positive and the negative controls correspond to the maximum cell lysis and to the untreated cells respectively. The data were worked up by subtracting the absorbance of untreated cells from all of the treatment conditions, including the cell lysis, and then dividing by the corrected lysis value. The % of cytotoxicity was calculated as:

$$\%\ \text{Cytotoxicity} = 100 \times \frac{(\text{Experimental LDH Release} - \text{Medium Background})}{(\text{Maximum LDH Release Control} - \text{Medium Background})}$$

Cell viability was assessed by measuring the amount of lactate dehydrogenase (LDH) released into the cell culture supernatant by damaged cells. Conversion of lactate to pyruvate produces NADH which in turns reduces a yellow tetrazolium salt (iodonitrotetrazolium violet; INT) into a red formazan dye that absorbs at 490 and 492 nm. As a consequence, the amount of LDH in the supernatant is proportional to the amount of formazan and it informs about the number or lysed cells (dead or damaged).

The LDH release was evaluated using TH1 cells and measured between 1 and 200 μM of PMO-P7, PMO-P21, and PMO-P23 (FIG. 22).

Example 12: Endotoxin Assay

The amount of endotoxin in PMO-P7 was measured. A chromogenic LAL (Limulus Amebocyte Lysate) assay for the detection and quantification of bacterial endotoxins was used. LAL is an extract of blood cells (amoebocytes) from the Atlantic horseshoe crab. This assay is based on the reaction of LAL with bacterial endotoxin lipopolysaccharide (LPS), which is a membrane component of gram-negative bacteria. In this method the LAL reagent is mixed with a chromogenic reagent (a peptide connected to p-nitroaniline, a yellow colorant) to produce a synthetic chromogenic substrate. The sample was added to this chromogenic substrate prior incubation. The presence of endotoxins in the sample produces a series of enzymatic reactions in the LAL reagent resulting in the breaking of the peptide bonds releasing p-nitroaniline molecules and therefore producing a yellow color. The concentration of endotoxin is quantitated by measuring the absorbance at 405-410 nm. Using the lot of PMO-P7 for animal studies, PMO-P7 solution was prepared using 0.5 mg of PMO-P7 as acetate salt dissolved in 1 mL of PBS (1×). The cartridge used was the 0.01 of the Charles River Endosafe nexgen-PTS. 25 μL of the sample were placed into each of the four sample reservoirs of the cartridge. The reader mixed the sample with the LAL (Limulus Amebocyte Lysate) reagent. The sample was combined with the chromogenic substrate and then incubated. After mixing, the optical density of the wells was measured and analyzed against an internal archived standard curve. The reading was 0.0471 EU/mg (EU: endotoxin units).

The molecular weight of PMO-P7 as its trifluoroacetic salt is 10,069 g/mol and as its acetate salt is 9,529 g/mol.

Example 13: Animal Studies

The mice used in the study contain a similar transgene as the HeLa654 cells from Example 4. This mouse model ubiquitously expresses EGFP-654 transgene throughout the body under chicken β-actin promoter. A mutated nucleotide 654 at intron 2 of human β-globin gene is contained in the EGFP-654 sequence which interrupts EGFP-654 coding sequence and prevents proper translation of EGFP protein. The antisense activity of PMO blocks aberrant splicing and resulted in EGFP expression, the same as in the HeLa 654 assay. In this study, 6- to 8-week-old male EGFP-654 mice bred at Charles River Laboratory were used. These mice were group housed with ad libitum access to food and water.

Before injection, the PMO-peptide was confirmed to have minimal endotoxin levels. For the endotoxin assay measurement using the PMO-P7 lot that was used for animal studies, 0.5 mg of PMO-P7 as acetate salt were dissolved in 1 mL of PBS (1×). The cartridge used was the 0.01 of the Charles River Endosafe nexgen-PTS. 25 μL of the sample were placed into each of the four sample reservoirs of the cartridge. The lot of PMO-P7 (63 mg as acetate salt) used for animal studies showed 0.0471 EU/mg (EU refers to Endotoxin Units).

After 3-days of acclimation, mice were randomized into groups to receive a single i.v. tail vein injection of either saline or PMO-P7 at the indicated doses; 5, 10 and 30 mg/kg. Seven days after the injection, the mice were euthanized for serum and tissue sample collection. Quadriceps, diaphragm, heart were rapidly dissected, snap-frozen in liquid nitrogen and stored at −80° C. until analysis.

Serum from all groups were collected 7-days post-injection and tested for kidney injury markers using a Vet Axcel Clinical Chemistry System (Alfa Wassermann Diagnostic Technologies, LLC). Specifically, serum BUN, creatinine, and cystatin C levels were measured using ACE® Creatinine Reagent (Alfa Wassermann, Cat #SA1012), ACE® Blood Urea Nitrogen Reagent (Alfa Wassermann, Cat #SA2024) and Diazyme Cystatin C immunoassay (Diazyme Laboratories, Cat #DX133C-K), respectively, per manufacturer's recommendation (See, FIGS. 24 A-C).

20-25 mg of mouse tissue was homogenized in RIPA buffer (Thermo Fisher, Cat #89900) with protease inhibitor cocktail (Roche, 04693124001) using a Fast Prep 24-5G instrument (MP Biomedical). Homogenates were centrifuged at 12,000 g for 10 min at 4° C.

The resultant supernatant lysates were quantified by Pierce BCA Protein Assay Kit (Thermo Fisher, Cat #23225) and saved for EGFP expression measurement. Specifically, 80 μg of lysates were aliquoted in each well in a black-wall clear-bottom 96-well microplate (Corning). EGFP fluorescent intensity of each sample was measured in duplicates using a SpectraMAx i3x microplate reader (Molecular devices) by default setting. The average EGFP fluorescent intensity of each sample was then plotted against a standard curve constructed by recombinant EGFP protein (Origen, Cat #TP790050) to quantify EGFP protein level per μg protein lysate (See FIGS. 24 D-F).

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

The invention claimed is:

1. A peptide-oligonucleotide conjugate of Formula II:

(II)

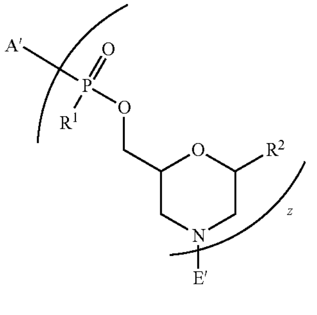

or a pharmaceutically acceptable salt thereof, wherein:

A' is selected from —N(H)$CH_2C(O)NH_2$, —N($C_{1-6}$-alkyl)$CH_2C(O)NH_2$,

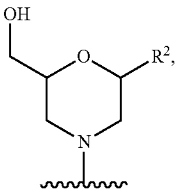

and

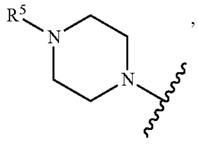

, wherein $R^5$ is —C(O)(O-alkyl)$_x$-OH, wherein x is 3-10 and each alkyl group is, independently at each occurrence, $C_{2-6}$-alkyl, or $R^5$ is selected from —C(O)$C_{1-6}$-alkyl, trityl, monomethoxytrityl, —($C_{1-6}$-alkyl)-$R^6$, —($C_{1-6}$-heteroalkyl)-$R^6$, aryl-$R^6$, heteroaryl-$R^6$, —C(O)O—($C_{1-6}$-alkyl)-$R^6$, —C(O)O-aryl-$R^6$, —C(O)O-heteroaryl-$R^6$, and

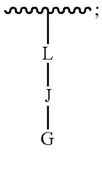

;

wherein $R^6$ is selected from OH, SH, and $NH_2$, or $R^6$ is O, S, or NH, each of which are covalently-linked to a solid support;

each $R^1$ is independently selected from OH and —N($R^3$)($R^4$), wherein each $R^3$ and $R^4$ are, independently at each occurrence, —$C_{1-6}$-alkyl;

each $R^2$ is independently, at each occurrence, selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, —$C_{1-6}$-alkyl, —C(O)$C_{1-6}$-alkyl, benzoyl, stearoyl, trityl, monomethoxytrityl, dimethoxytrityl, trimethoxytrityl,

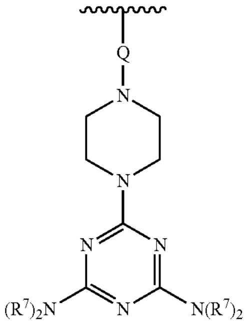

and

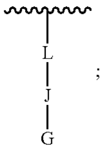

;

wherein

Q is —C(O)$(CH_2)_6$C(O)— or —C(O)$(CH_2)_2S_2(CH_2)_2$C(O)—;

$R^7$ is —$(CH_2)_2$OC(O)N$(R^8)_2$, wherein $R^8$ is —$(CH_2)_6$NHC(=NH)$NH_2$;

L is —C(O)$(CH_2)_{1-6}$—$C_{7-15}$-heteroaromatic-$(CH_2)_{1-6}$C(O)—, wherein L is covalently-linked by an amide bond to J;

J is a carrier peptide;

G is selected from H, —C(O)$C_{1-6}$-alkyl, benzoyl, and stearoyl, wherein G is covalently-linked to J;

wherein at least one of the following conditions is true:

1) A' is

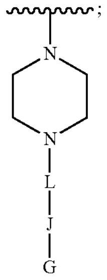

or 2) E' is

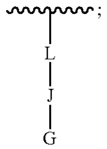

and wherein the carrier peptide J is selected from the following sequences:

| | |
|---|---|
| P1 (MACH 14) (SEQ ID NO: 69) | KXKKQQGKKKHR |
| P2 (MACH 15) (SEQ ID NO: 70) | KKKKKQBKKKHRWPMG |
| P3 (MACH 16) (SEQ ID NO: 71) | KKKKNQBKKKHRWPMKXCPQ |
| P4 (MACH 17) (SEQ ID NO: 72) | HKKKKQBKKKHRWP |
| P5 (MACH 18) (SEQ ID NO: 73) | KXKHQQQXK |
| P6 (MACH 19) (SEQ ID NO: 74) | KXKXT |
| P7 (MACH 20) (SEQ ID NO: 75) | KKKKKQBKKKHRWPKXXC |

-continued

| | |
|---|---|
| P8 (SEQ ID NO: 76) | KKKKKCBKKKHRWPKXXQ |
| P9 (SEQ ID NO: 77 | KKKXKQBKKKHRWPKKXC |
| P10 (SEQ ID NO: 78) | KCHKXKWKKPKRXKQKBK |
| P11 (SEQ ID NO: 79) | KKKKKQCKKKHRWPKXXC |
| P12 (SEQ ID NO: 80) | KKKKKQBKKKHRWPKXXG |
| P13 (SEQ ID NO: 81) | KKKKKQBKKKHRWPMGKXXC |
| P14 (SEQ ID NO: 82) | HKKKKQBKKKHRWPKXXC |
| P15 (SEQ ID NO: 83) | KXKHQQQXKKXXC |
| P16 (SEQ ID NO: 84) | KXKXTKXXC |
| P18 (SEQ ID NO: 85) | ALWKTLLKKVLKAPKKKRKVKXXC |
| P20 (SEQ ID NO: 86) | RQIKIWFQNRRMKWKKKXXC |
| P21 (SEQ ID NO: 87 | KKKKKQBKKKHRWP |
| P22 (SEQ ID NO: 88) | KKKKKQBKKKHRWPKXXCCC |
| P23 (SEQ ID NO: 89) | KKKKKQBKKKHRWAKXXC |
| P24 (SEQ ID NO: 90) | KXKHQQGP |
| P25 (SEQ ID NO: 91) | KXKHQQGKKT |
| P26 (SEQ ID NO: 92) | HKKKQQGKKKHRW |
| P27 (SEQ ID NO: 93) | KKKKKQBKKKHRWPM |
| P28 (SEQ ID NO: 94) | KKKKKQGKKHRWPMGG |
| P29 (SEQ ID NO: 95) | KKKKNQBKKKHRWPMKXCP |

-continued

| | |
|---|---|
| P30 (SEQ ID NO: 96) | KKKKKQBKKKHRWPKXXA |
| P31 (SEQ ID NO: 97) | KKKKKQBKKKHRWPKXAC |
| P32 (SEQ ID NO: 98) | KKKKKQBKKKHRWPKAXC |
| P33 (SEQ ID NO: 99) | KKKKKQBKKKHRWPAXXC |
| P34 (SEQ ID NO: 100) | KAKKKQBKKKHRWPKXXC |
| P35 (SEQ ID NO: 101) | KKKKKQBKAKHRWPKXXC |
| P36 (SEQ ID NO: 102) | KKKAKQBKKKHRWPKXXC |
| P37 (SEQ ID NO: 103) | KKKAKQBKAKHRWPKXXC |
| P38 (SEQ ID NO: 104) | KAKAKQBKKKHRWPKXXC; and |
| P39 (SEQ ID NO: 105) | KAKAKQBKAKHRWPKXXC |

wherein X is 6-amino hexanoic acid, and B is β-alanine.

2. The peptide-oligonucleotide conjugate of claim 1, wherein

A' is selected from —$N(C_{1-6}\text{-alkyl})CH_2C(O)NH_2$,

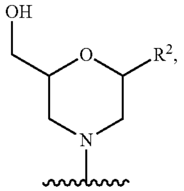

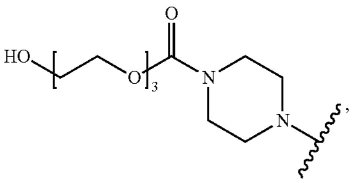

and

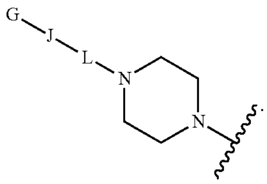

3. The conjugate of claim 1, wherein E' is selected from H, —$C(O)CH_3$, benzoyl, stearoyl, trityl, 4-methoxytrityl, and

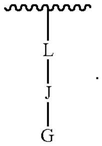

4. The conjugate of claim 1, wherein the peptide-oligonucleotide conjugate of Formula II is a peptide-oligonucleotide conjugate selected from:

(Ia)

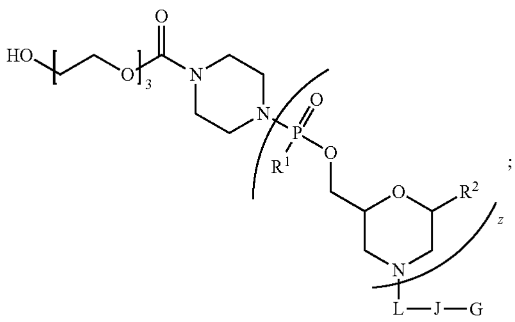

; and

-continued (Ib)

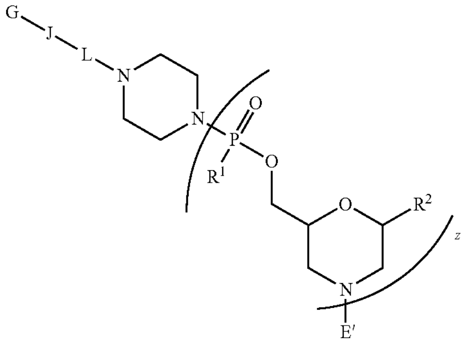

wherein E' is selected from H, $C_{1-6}$-alkyl, —C(O)$CH_3$, benzoyl, and stearoyl.

5. The conjugate of claim 1, wherein each $R^2$ is a nucleobase, independently at each occurrence, selected from adenine, guanine, cytosine, 5-methyl-cytosine, thymine, uracil, and hypoxanthine.

6. The conjugate of claim 1, wherein L is —C(O)$(CH_2)_{1-6}$-8,9-dihydro-3H-dibenzo[b,f][1,2,3]triazolo[4,5-d]azocine-$(CH_2)_{1-6}$C(O)—.

7. The conjugate of claim 1, wherein L is

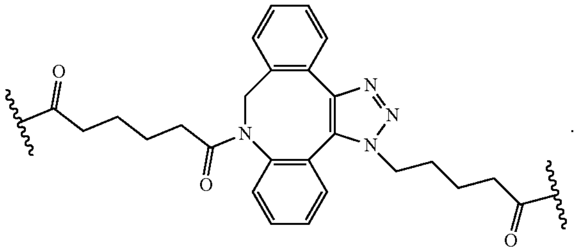 [SMILES: *C(=O)CCCCC(=O)N1Cc2ccccc2-c2nnn(CCCCC(*)=O)c2-c2ccccc21]

.

8. The conjugate of claim 1, wherein G is selected from H, C(O)$CH_3$, benzoyl, and stearoyl.

9. A pharmaceutical composition comprising the conjugate of claim 1, and at least one pharmaceutically acceptable carrier.

10. The conjugate of claim 1, wherein J is selected from the following sequences:

| | |
|---|---|
| P1 (MACH 14) (SEQ ID NO: 69) | KXKKQQGKKKHR |
| P2 (MACH 15) (SEQ ID NO: 70) | KKKKKQBKKKHRWPMG |
| P3 (MACH 16) (SEQ ID NO: 71) | KKKKNQBKKKHRWPMKXCPQ |
| P4 (MACH 17) (SEQ ID NO: 72) | HKKKKQBKKKHRWP |
| P5 (MACH 18) (SEQ ID NO: 73) | KXKHQQQXK |
| P6 (MACH 19) (SEQ ID NO: 74) | KXKXT |
| P7 (MACH 20) (SEQ ID NO: 75) | KKKKKQBKKKHRWPKXXC |

-continued

| | |
|---|---|
| P8 (SEQ ID NO: 76) | KKKKKCBKKKHRWPKXXQ |
| P9 (SEQ ID NO: 77) | KKKXKQBKKKHRWPKKXC |
| P10 (SEQ ID NO: 78) | KCHKXKWKKPKRXKQKBK |
| P11 (SEQ ID NO: 79) | KKKKKQCKKKHRWPKXXC |
| P12 (SEQ ID NO: 80) | KKKKKQBKKKHRWPKXXG |
| P13 (SEQ ID NO: 81) | KKKKKQBKKKHRWPMGKXXC |
| P14 (SEQ ID NO: 82) | HKKKKQBKKKHRWPKXXC |
| P15 (SEQ ID NO: 83) | KXKHQQQXKKXXC |
| P16 (SEQ ID NO: 84) | KXKXTKXXC |
| P18 (SEQ ID NO: 85) | ALWKTLLKKVLKAPKKKRKVKXXC |
| P20 (SEQ ID NO: 86) | RQIKIWFQNRRMKWKKKXXC |
| P21 (SEQ ID NO: 87) | KKKKKQBKKKHRWP |
| P22 (SEQ ID NO: 88) | KKKKKQBKKKHRWPKXXCCC; and |
| P23 (SEQ ID NO: 89) | KKKKKQBKKKHRWAKXXC. |

11. The conjugate of claim 1, wherein J is selected from the following sequences:

| | |
|---|---|
| P24 (SEQ ID NO: 90) | KXKHQQGP |
| P25 (SEQ ID NO: 91) | KXKHQQGKKT |
| P26 (SEQ ID NO: 92) | HKKKQQGKKKHRW |
| P27 (SEQ ID NO: 93) | KKKKKQBKKKHRWPM |
| P28 (SEQ ID NO: 94) | KKKKKQGKKHRWPMGG |
| P29 (SEQ ID NO: 95) | KKKKNQBKKKHRWPMKXCP |
| P30 (SEQ ID NO: 96) | KKKKKQBKKKHRWPKXXA |
| P31 (SEQ ID NO: 97) | KKKKKQBKKKHRWPKXAC |
| P32 (SEQ ID NO: 98) | KKKKKQBKKKHRWPKAXC |
| P33 (SEQ ID NO: 99) | KKKKKQBKKKHRWPAXXC |
| P34 (SEQ ID NO: 100) | KAKKKQBKKKHRWPKXXC |

-continued

| | |
|---|---|
| P35 (SEQ ID NO: 101) | KKKKKQBKAKHRWPKXXC |
| P36 (SEQ ID NO: 102) | KKKAKQBKKKHRWPKXXC |
| P37 (SEQ ID NO: 103) | KKKAKQBKAKHRWPKXXC |
| P38 (SEQ ID NO: 104) | KAKAKQBKKKHRWPKXXC; and |
| P39 (SEQ ID NO: 105) | KAKAKQBKAKHRWPKXXC. |

12. The peptide-oligonucleotide conjugate of claim 10, wherein A' is selected from —$N(C_{1-6}\text{-alkyl})CH_2C(O)NH_2$,

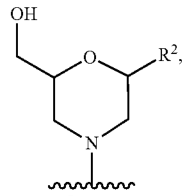

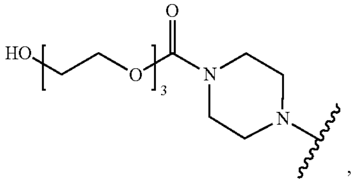

, and

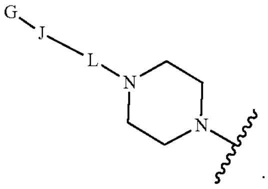

.

13. The conjugate of claim 10, wherein E' is selected from H, —$C(O)CH_3$, benzoyl, stearoyl, trityl, 4-methoxytrityl, and

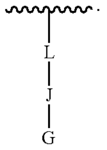

14. The conjugate of claim 10, wherein the peptide-oligonucleotide conjugate of Formula II is a peptide-oligonucleotide conjugate selected from:

(Ia)

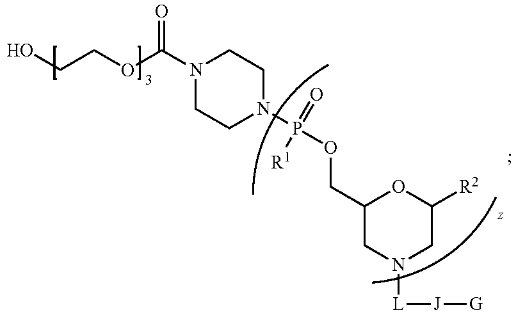

; and (Ib)

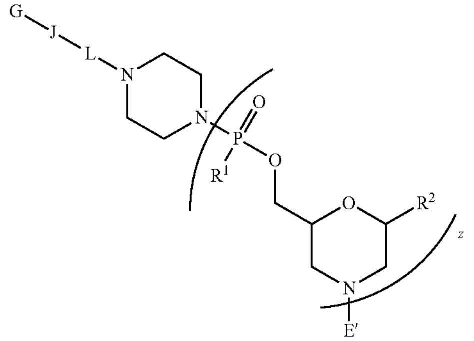

wherein E' is selected from H, $C_{1-6}$-alkyl, —$C(O)CH_3$, benzoyl, and stearoyl.

15. The conjugate of claim 10, wherein each $R^2$ is a nucleobase, independently at each occurrence, selected from adenine, guanine, cytosine, 5-methyl-cytosine, thymine, uracil, and hypoxanthine.

16. The conjugate of claim 10, wherein L is —$C(O)(CH_2)_{1-6}$-8,9-dihydro-3H-dibenzo[b,f][1,2,3]triazolo[4,5-d]azocine-$(CH_2)_{1-6}C(O)$—.

17. The conjugate of claim 10, wherein L is

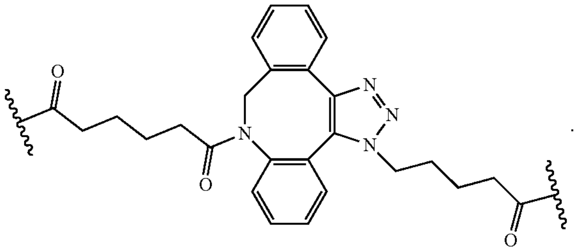 [SMILES: *C(=O)CCCCC(=O)N1Cc2ccccc2-c2nnn(CCCCC(*)=O)c2-c2ccccc21]

.

18. The conjugate of claim 5, wherein G is selected from H, $C(O)CH_3$, benzoyl, and stearoyl.

* * * * *